US 10,194,950 B2

(12) United States Patent
Felix et al.

(10) Patent No.: US 10,194,950 B2
(45) Date of Patent: Feb. 5, 2019

(54) RADIOLUCENT SCREW WITH RADIOPAQUE MARKER

(75) Inventors: Brent A. Felix, Sandy, UT (US); David N. McKean, Bountiful, UT (US); David A. Hershgold, Draper, UT (US)

(73) Assignee: Innovasis, Inc., Salt Lake City, UT (US)

( * ) Notice: Subject to any disclaimer, the term of this patent is extended or adjusted under 35 U.S.C. 154(b) by 790 days.

(21) Appl. No.: 13/063,605

(22) PCT Filed: Sep. 10, 2009

(86) PCT No.: PCT/US2009/056508
§ 371 (c)(1),
(2), (4) Date: Mar. 11, 2011

(87) PCT Pub. No.: WO2010/030774
PCT Pub. Date: Mar. 18, 2010

(65) Prior Publication Data
US 2011/0172718 A1    Jul. 14, 2011

Related U.S. Application Data

(63) Continuation-in-part of application No. 12/208,986, filed on Sep. 11, 2008, now Pat. No. 9,408,649.

(51) Int. Cl.
A61B 17/86    (2006.01)
A61B 17/70    (2006.01)
A61B 90/00    (2016.01)

(52) U.S. Cl.
CPC ...... *A61B 17/7032* (2013.01); *A61B 17/7037* (2013.01); *A61B 17/866* (2013.01);
(Continued)

(58) Field of Classification Search
CPC . A61B 17/866; A61B 17/864; A61B 17/8685; A61B 90/39; A61B 17/7032; A61B 17/7037
(Continued)

(56) References Cited

U.S. PATENT DOCUMENTS 1,828,287 A    10/1931    Macbean
2,405,909 A     8/1946    Smith
(Continued)

FOREIGN PATENT DOCUMENTS

DE    44 43 051 A1    10/1996
DE    100 65 799 C1    4/2002
(Continued)

OTHER PUBLICATIONS

Office Action dated Nov. 9, 2011, issued in U.S. Appl. No. 12/557,081, filed Sep. 10, 2009.
(Continued)

*Primary Examiner* — Pedro Philogene
(74) *Attorney, Agent, or Firm* — Workman Nydegger

(57) ABSTRACT

A bone screw includes an elongate shaft extending longitudinally between a proximal end and an opposing distal end The shaft bounds a first passageway at least partially extending between the proximal end and the distal end. The shaft is comprised of a radiolucent material. A core is disposed within the first passageway of the shaft. The core can be comprised of a radiolucent or radiopaque material. A head is either integrally formed with or secured to the proximal end of the shaft or the proximal end of the core. The head can also bound a second passageway that extends through the head and is aligned with the first passageway. The core can also be disposed within the second passageway.

18 Claims, 36 Drawing Sheets

(52) U.S. Cl.
CPC ........ *A61B 17/8685* (2013.01); *A61B 17/864* (2013.01); *A61B 90/39* (2016.02)

(58) Field of Classification Search
USPC .................. 606/76, 331, 300–328, 246–279
See application file for complete search history.

(56) References Cited

U.S. PATENT DOCUMENTS

| | | | |
|---|---|---|---|
| 3,455,360 A | 7/1969 | Simons | |
| 4,063,838 A | 12/1977 | Michael | |
| 4,265,981 A | 5/1981 | Campbell | |
| 4,307,979 A | 12/1981 | Killmeyer | |
| 4,329,743 A | 5/1982 | Alexander et al. | |
| 4,403,606 A | 9/1983 | Woo et al. | |
| 4,512,038 A | 4/1985 | Alexander et al. | |
| 4,623,290 A | 11/1986 | Kikuzawa et al. | |
| 4,778,637 A | 10/1988 | Adams et al. | |
| 4,863,330 A | 9/1989 | Olez et al. | |
| 4,863,470 A | 9/1989 | Carter | |
| 5,084,051 A | 1/1992 | Tormala et al. | |
| 5,127,783 A * | 7/1992 | Moghe et al. ................ | 411/411 |
| 5,209,888 A | 5/1993 | Shimada et al. | |
| 5,246,655 A | 9/1993 | Mitchell et al. | |
| 5,366,773 A | 11/1994 | Schroll et al. | |
| 5,466,237 A | 11/1995 | Byrd, III et al. | |
| 5,474,555 A | 12/1995 | Puno et al. | |
| 5,540,870 A | 7/1996 | Quigley | |
| 5,676,146 A | 10/1997 | Scarborough | |
| 5,807,051 A | 9/1998 | Heminger | |
| 5,951,556 A | 9/1999 | Faccioli et al. | |
| 6,059,769 A | 5/2000 | Lunn et al. | |
| 6,063,090 A | 5/2000 | Schlapfer | |
| 6,099,528 A | 8/2000 | Saurat | |
| 6,113,826 A | 9/2000 | Tajima et al. | |
| 6,117,173 A | 9/2000 | Taddia et al. | |
| 6,174,329 B1 | 1/2001 | Callol et al. | |
| 6,203,568 B1 | 3/2001 | Lombardi et al. | |
| 6,214,921 B1 | 4/2001 | Bluett et al. | |
| 6,248,105 B1 | 6/2001 | Schlapfer et al. | |
| 6,280,442 B1 | 8/2001 | Barker et al. | |
| 6,302,630 B1 | 10/2001 | Grant | |
| 6,340,367 B1 | 1/2002 | Stinson et al. | |
| 6,342,055 B1 | 1/2002 | Eisemann et al. | |
| 6,371,957 B1 | 4/2002 | Amrein et al. | |
| 6,423,067 B1 | 7/2002 | Eisermann | |
| 6,471,705 B1 | 10/2002 | Biedermann et al. | |
| 6,565,567 B1 | 5/2003 | Haider | |
| 6,575,975 B2 | 6/2003 | Brace et al. | |
| 6,599,290 B2 | 7/2003 | Bailey et al. | |
| 6,641,586 B2 | 11/2003 | Varieur | |
| 6,660,004 B2 | 12/2003 | Barker et al. | |
| 6,679,883 B2 | 1/2004 | Hawkes et al. | |
| 6,712,852 B1 | 3/2004 | Chung et al. | |
| 6,740,086 B2 | 5/2004 | Richelsoph | |
| 6,837,905 B1 | 1/2005 | Lieberman | |
| 6,955,513 B2 | 10/2005 | Niku | |
| 6,974,480 B2 | 12/2005 | Messerli et al. | |
| 7,150,594 B2 | 12/2006 | Keener | |
| 7,169,150 B2 | 1/2007 | Shipp et al. | |
| 7,192,447 B2 | 3/2007 | Rhoda | |
| 7,235,079 B2 | 6/2007 | Jensen et al. | |
| 7,235,290 B2 | 6/2007 | Vallittu et al. | |
| 7,273,481 B2 | 9/2007 | Lombardo et al. | |
| 7,318,825 B2 | 1/2008 | Butler et al. | |
| 7,524,190 B2 | 4/2009 | Levin | |
| 7,766,942 B2 | 8/2010 | Patterson et al. | |
| 7,966,711 B2 | 6/2011 | Keener | |
| 7,988,710 B2 | 8/2011 | Jahjng et al. | |
| 7,998,180 B2 | 8/2011 | Erickson et al. | |
| 8,267,978 B2 | 9/2012 | Lindemann et al. | |
| 8,475,505 B2 | 7/2013 | Nebosky et al. | |
| 2002/0123751 A1 | 9/2002 | Fallin | |
| 2002/0133158 A1 | 9/2002 | Saint Martin | |
| 2003/0078583 A1 | 4/2003 | Biedemann et al. | |
| 2004/0034430 A1 | 2/2004 | Faiahee | |
| 2004/0127904 A1 | 7/2004 | Konieczynski et al. | |
| 2004/0143265 A1 | 7/2004 | Landry et al. | |
| 2004/0199251 A1 | 10/2004 | McCombe et al. | |
| 2004/0210226 A1 | 10/2004 | Trieu | |
| 2004/0210316 A1 | 10/2004 | King et al. | |
| 2004/0215195 A1 | 10/2004 | Shipp et al. | |
| 2004/0243129 A1 | 12/2004 | Moumene et al. | |
| 2005/0187550 A1 | 8/2005 | Grusin | |
| 2005/0187555 A1 * | 8/2005 | Biedermann et al. .......... | 606/72 |
| 2005/0203516 A1 | 9/2005 | Biedermann et al. | |
| 2005/0203517 A1 | 9/2005 | Jahng et al. | |
| 2005/0203519 A1 | 9/2005 | Harms et al. | |
| 2005/0216081 A1 | 9/2005 | Taylor | |
| 2005/0228388 A1 | 10/2005 | Brodke et al. | |
| 2005/0228479 A1 | 10/2005 | Pavcnik et al. | |
| 2006/0041259 A1 | 2/2006 | Paul et al. | |
| 2006/0084986 A1 * | 4/2006 | Grinberg et al. ............... | 606/61 |
| 2006/0085072 A1 | 4/2006 | Funk et al. | |
| 2006/0089644 A1 | 4/2006 | Felix | |
| 2006/0142758 A1 | 6/2006 | Petit | |
| 2006/0149228 A1 | 7/2006 | Schlapher et al. | |
| 2006/0195093 A1 | 8/2006 | Jahng | |
| 2006/0200140 A1 | 9/2006 | Lange | |
| 2006/0235410 A1 | 10/2006 | Ralph et al. | |
| 2006/0247638 A1 | 11/2006 | Trieu et al. | |
| 2006/0276788 A1 | 12/2006 | Berry et al. | |
| 2007/0123879 A1 | 5/2007 | Songer et al. | |
| 2007/0156145 A1 | 7/2007 | Demakas et al. | |
| 2007/0190230 A1 | 8/2007 | Trieu et al. | |
| 2007/0233071 A1 * | 10/2007 | Dewey et al. ................... | 606/61 |
| 2007/0233073 A1 | 10/2007 | Wisnewski et al. | |
| 2007/0250167 A1 | 10/2007 | Bray et al. | |
| 2007/0270851 A1 | 11/2007 | Erickson et al. | |
| 2008/0033437 A1 | 2/2008 | Shipp et al. | |
| 2008/0065070 A1 | 3/2008 | Fried et al. | |
| 2008/0077133 A1 | 3/2008 | Schulze et al. | |
| 2008/0082103 A1 | 4/2008 | Hutton et al. | |
| 2008/0083613 A1 | 4/2008 | Oi et al. | |
| 2008/0086127 A1 | 4/2008 | Patterson et al. | |
| 2008/0086129 A1 * | 4/2008 | Lindemann et al. .......... | 606/61 |
| 2008/0091214 A1 | 4/2008 | Richelsoph | |
| 2008/0097432 A1 | 4/2008 | Schulze | |
| 2008/0125777 A1 | 5/2008 | Veldman et al. | |
| 2008/0154306 A1 * | 6/2008 | Heinz .......................... | 606/256 |
| 2008/0154367 A1 | 6/2008 | Justis et al. | |
| 2008/0243185 A1 | 10/2008 | Felix et al. | |
| 2009/0082810 A1 * | 3/2009 | Bhatnagar et al. ........... | 606/250 |
| 2009/0093819 A1 | 4/2009 | Joshi | |
| 2009/0093844 A1 | 4/2009 | Jackson | |
| 2009/0112265 A1 | 4/2009 | Hudgins et al. | |
| 2009/0118767 A1 | 5/2009 | Hestad et al. | |
| 2009/0163955 A1 | 6/2009 | Moumene et al. | |
| 2009/0234388 A1 | 9/2009 | Patterson et al. | |
| 2009/0240284 A1 | 9/2009 | Randol et al. | |
| 2009/0248083 A1 | 10/2009 | Patterson et al. | |
| 2009/0275983 A1 | 11/2009 | Veldman et al. | |
| 2009/0287251 A1 | 11/2009 | Bae et al. | |
| 2009/0326582 A1 | 12/2009 | Songer et al. | |
| 2010/0042215 A1 | 2/2010 | Stalcup et al. | |
| 2010/0063550 A1 | 3/2010 | Felix | |
| 2010/0082064 A1 | 4/2010 | Chun et al. | |
| 2010/0087863 A1 | 4/2010 | Biedermann et al. | |
| 2010/0114167 A1 | 5/2010 | Wilcox et al. | |
| 2010/0160967 A1 | 6/2010 | Capozzoli | |
| 2010/0211104 A1 | 8/2010 | Moumene et al. | |
| 2010/0211105 A1 | 8/2010 | Moumene et al. | |
| 2011/0054534 A1 | 3/2011 | Biedermann et al. | |
| 2012/0109207 A1 | 5/2012 | Trieu | |

FOREIGN PATENT DOCUMENTS

| | | |
|---|---|---|
| FR | 2 899 787 | 10/2007 |
| GB | 2 294 399 | 1/1996 |
| JP | 2005-270250 | 10/2005 |
| JP | 2006-187658 | 7/2006 |
| JP | 2007-307368 | 11/2007 |
| WO | WO 94/04095 A1 | 3/1994 |
| WO | WO 2007/127845 | 11/2007 |
| WO | WO 2011/112321 A1 | 9/2011 |

(56) References Cited

FOREIGN PATENT DOCUMENTS

OTHER PUBLICATIONS

Office Action dated Jan. 19, 2012, issued in U.S. Appl. No. 12/719,765, filed Mar. 8, 2010.
Final Office Action dated Jun. 6, 2012, issued in U.S. Appl. No. 12/577,081, filed Sep. 10, 2009.
Final Office Action dated May 9, 2012, issued in U.S. Appl. No. 12/719,765, filed Mar. 8, 2010.
Office Action dated Aug. 17, 2012, issued in U.S. Appl. No. 12/719,765, filed Mar. 8, 2010.
Office Action dated Jul. 10, 2012, issued in U.S. Appl. No. 12/208,986, filed Sep. 11, 2008.
Final Office Action dated Dec. 14, 2012, issued in U.S. Appl. No. 12/208,986, filed Sep. 11, 2008.
Office Action dated Feb. 16, 2013, issued in Chinese Application No. 200980144925.0, filed Sep. 11, 2011.
Office Action dated Sep. 14, 2011 issued in EP Application No. 09792417.9, filed Sep. 11, 2011.
International Search and Written Opinion dated May 23, 2011, issued in PCT/US2011/024935, filed Feb. 15, 2011.
International Search and Written Opinion dated Nov. 10, 2010, issued in PCT/US2010/048243, filed Sep. 9, 2010.
*VLS System Variable Locking Screw*, Interpore Cross International, 2001.
*EBI Spine Systems, EBI Ωmega21 Spinal Fixation System, Surgical Technique*, published at least as early as Sep. 1, 2006.
*Click'X Top Loading System, Technique Guide*, Synthes Spine 2003.
*Synergy IQ, Low Back Surgical Technique*, Interpore Cross International, 2003.
S. Kawahara et al., Summary of *Clinical Imaging Diagnosis of Implant Materials for Breast Augmentation*, Ann Plast Surg., Jul. 2006; 57(1), pp. 6-12 (1 page).
International Search Report and Written Opinion of PCT Publication No. WO 2010/030774, dated Dec. 3, 2009.
Office Action dated May 2, 2014, issued in U.S. Appl. No. 12/208,986, filed Sep. 11, 2008.
Notice of Allowance and Issue Fee dated Apr. 4, 2014, issued in U.S. Appl. No. 12/719,765, filed Mar. 8, 2010.
Office Action dated Nov. 18, 2014, issued in U.S. Appl. No. 12/208,986, filed Sep. 11, 2008.
Office Action dated Jan. 2, 2014, issued in U.S. Appl. No. 12/557,081, filed Sep. 10, 2009.
Office Action dated Feb. 20, 2015, issued in U.S. Appl. No. 12/557,081, filed Sep. 10, 2009.
Office Action dated May 29, 2015, issued in U.S. Appl. No. 12/208,986, filed Sep. 11, 2008.
Notice of Allowance dated Mar. 31, 2016, issued in U.S. Appl. No. 12/208,986, filed Sep. 11, 2008.

* cited by examiner

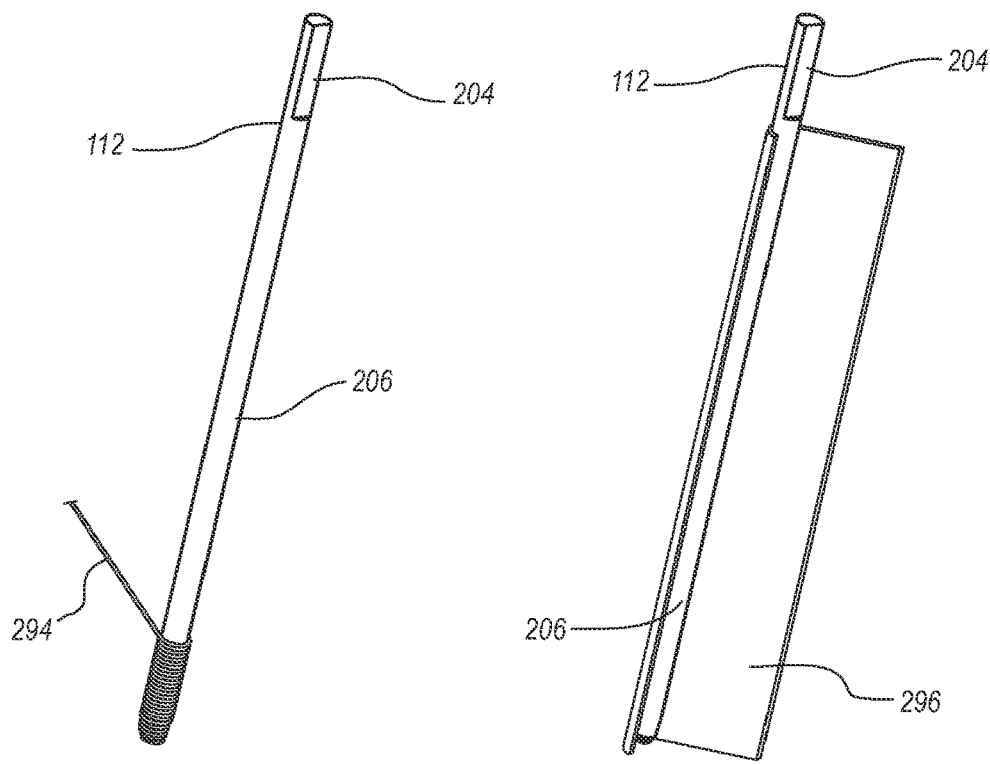
FIG. 14  FIG. 15
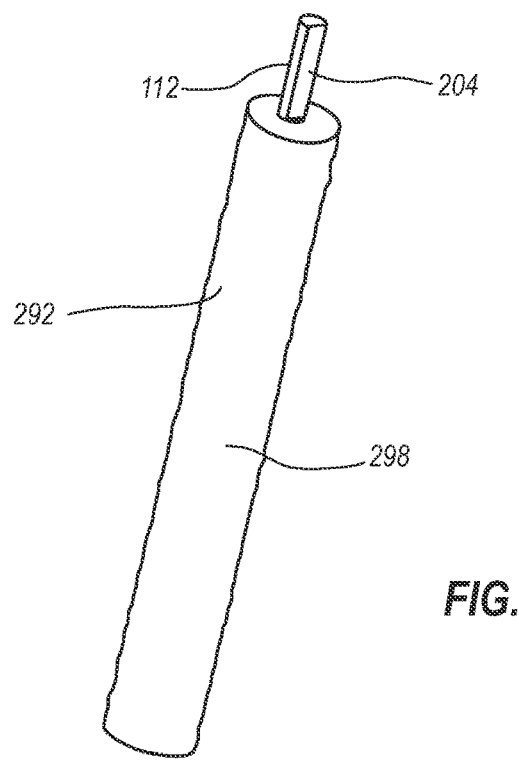
FIG. 16

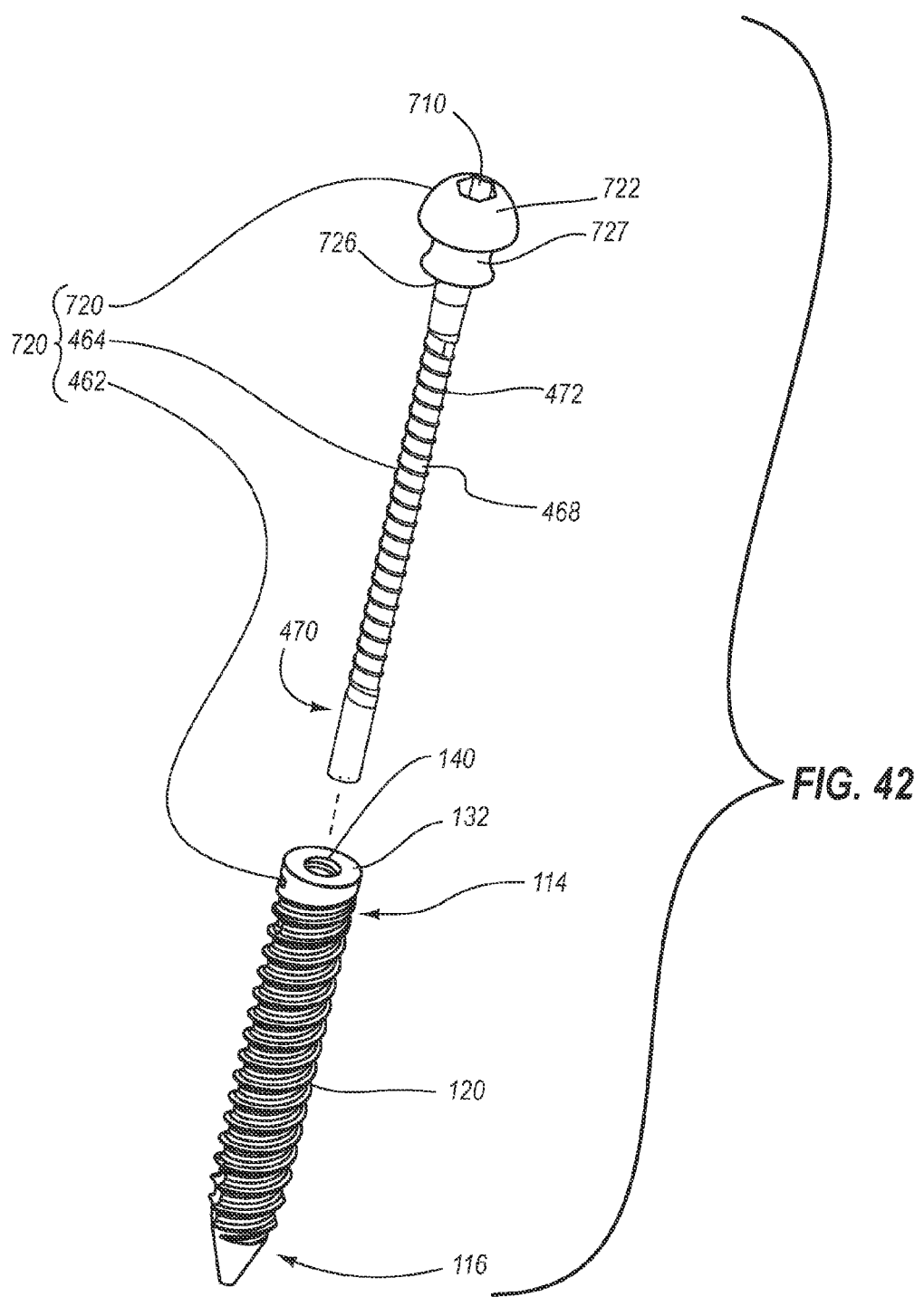

RADIOLUCENT SCREW WITH RADIOPAQUE MARKER

BACKGROUND OF THE INVENTION

1. The Field of the Invention

The present invention relates to polyaxial and fixed bone screws and components thereof that can be used for stabilizing adjacent vertebrae of the spine or otherwise fixing to bone.

2. The Relevant Technology

Polyaxial and fixed bone screws (often referred to as pedicle screws) are commonly used in spinal operations for adjusting or stabilizing adjacent vertebrae. For example, in one conventional procedure a first bone screw is screwed into a first vertebra while a second bone screw is screwed into an adjacent second vertebra. A stabilizing rod is then secured between the bone screws so as to fix the adjacent vertebrae relative to each other. Bone screws can be positioned on each side of each vertebra and can be positioned in any number of consecutive vertebrae with one or more stabilizing rods extending between the different bone screws.

A conventional bone screw comprises a threaded screw portion having a collar either fixedly or pivotably mounted on the end thereof. The screw portion is threaded into the bone and the stabilizing rod is received within the collar and secured therein. Other conventional bone screws are used for purposes such as securing a bone plate over a facture, fixing a cranial plate, attaching ligaments, mounting an implant and the like. To be strong enough to handle the stresses placed upon them, the bone screws are typically made of titanium or some other biocompatible metal. Being made of metal allows the doctor to view the bone screws using X-ray photographs during and after implantation.

However, because the bone screws are made of metal, the bone screws block X-rays passing through the body, in effect obscuring adjacent bone and other X-ray viewable internal structures surrounding the area and thereby preventing the surgeon from viewing those structures on an X-ray photograph. The metal bone screws can also disrupt MRI and other types of images. This can limit a surgeon's ability to ensure proper placement of the bone screws and diagnose and treat problems that arise near the location of the bone screws after the bone screws have been implanted.

Accordingly, what is needed are polyaxial and fixed bone screws that overcome some or all of the above disadvantages.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 14 is a perspective view of impregnated fibers being wound on the core shown in FIG. 2;

FIG. 15 is a perspective view of sheets of fibers being wound on the core shown in FIG. 2;

FIG. 16 is a perspective view of a blank that is formed during manufacture of the screw portion shown in FIG. 3 according to one embodiment;

FIG. 42 is an exploded perspective view of another bone screw having a modified head.

DETAILED DESCRIPTION OF THE PREFERRED EMBODIMENTS

Figure 1:
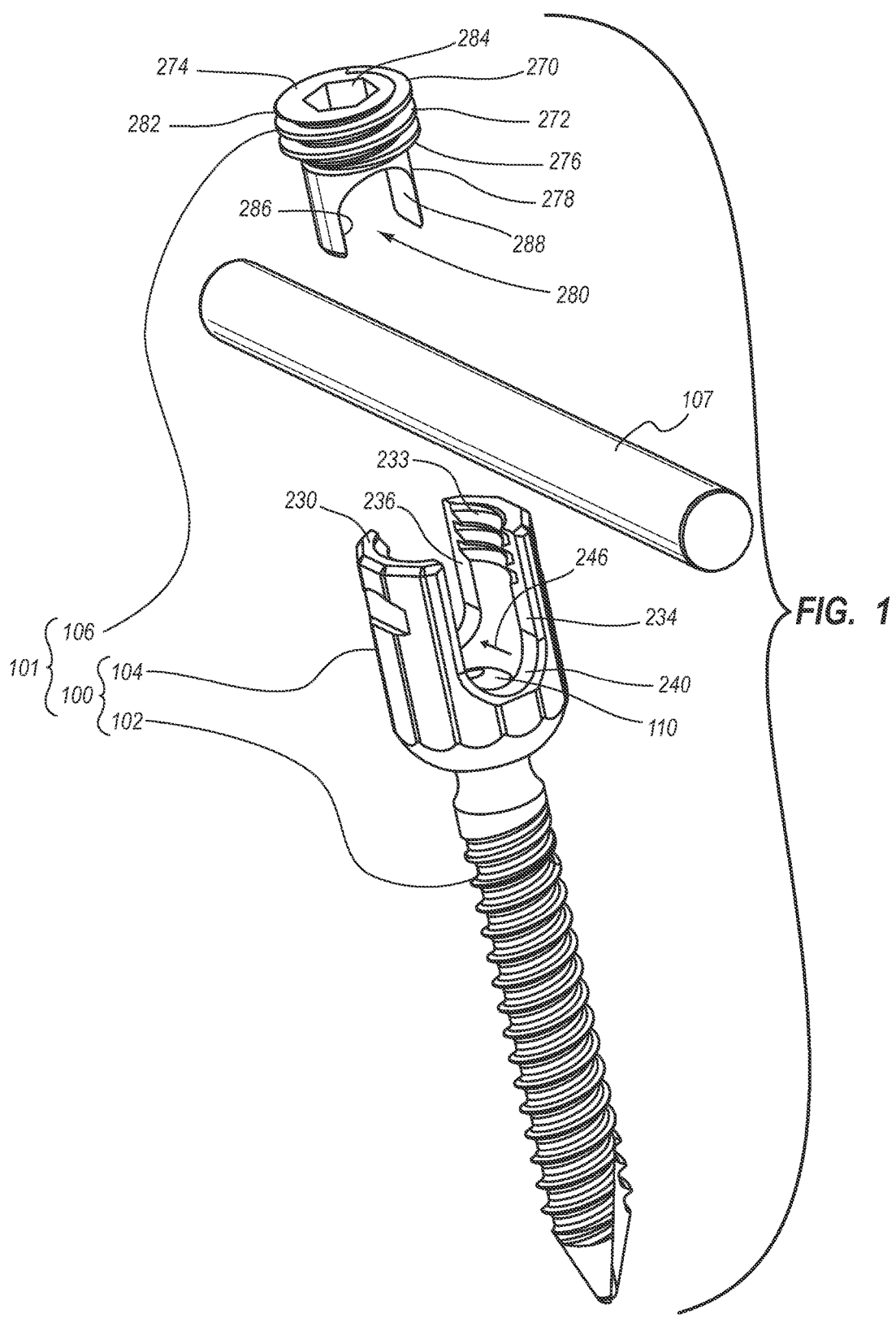
FIG. 1 is a perspective view of a spinal stabilizing system incorporating a polyaxial bone screw according to one embodiment of the present invention.

Depicted in FIG. 1 is a spinal stabilizing system 101 incorporating features of the present invention. Spinal stabilizing system 101 can be used for stabilizing adjacent vertebrae of a spine as part of a procedure for fusing together the adjacent vertebrae. Spinal stabilizing system 101 can also be used for stabilizing a series of consecutive vertebrae for manipulation of the spine to correct spinal deformities such as scoliosis. It is appreciated that spinal stabilizing system 101 and/or discrete elements thereof can also be used in other procedures for anchoring, manipulating, and/or stabilizing various bones.

As depicted in FIG. 1, stabilizing system 101 includes a polyaxial bone screw 100 comprising an elongated screw portion 102 and a collar 104 pivotally mounted thereon. Stabilizing system 101 also includes a fastener 106 that is selectively engageable with collar 104 to secure polyaxial bone screw 100 to a stabilizing rod 107. The above identified components of polyaxial screw 100 and their relative interaction will now be discussed in greater detail.

Figure 2:
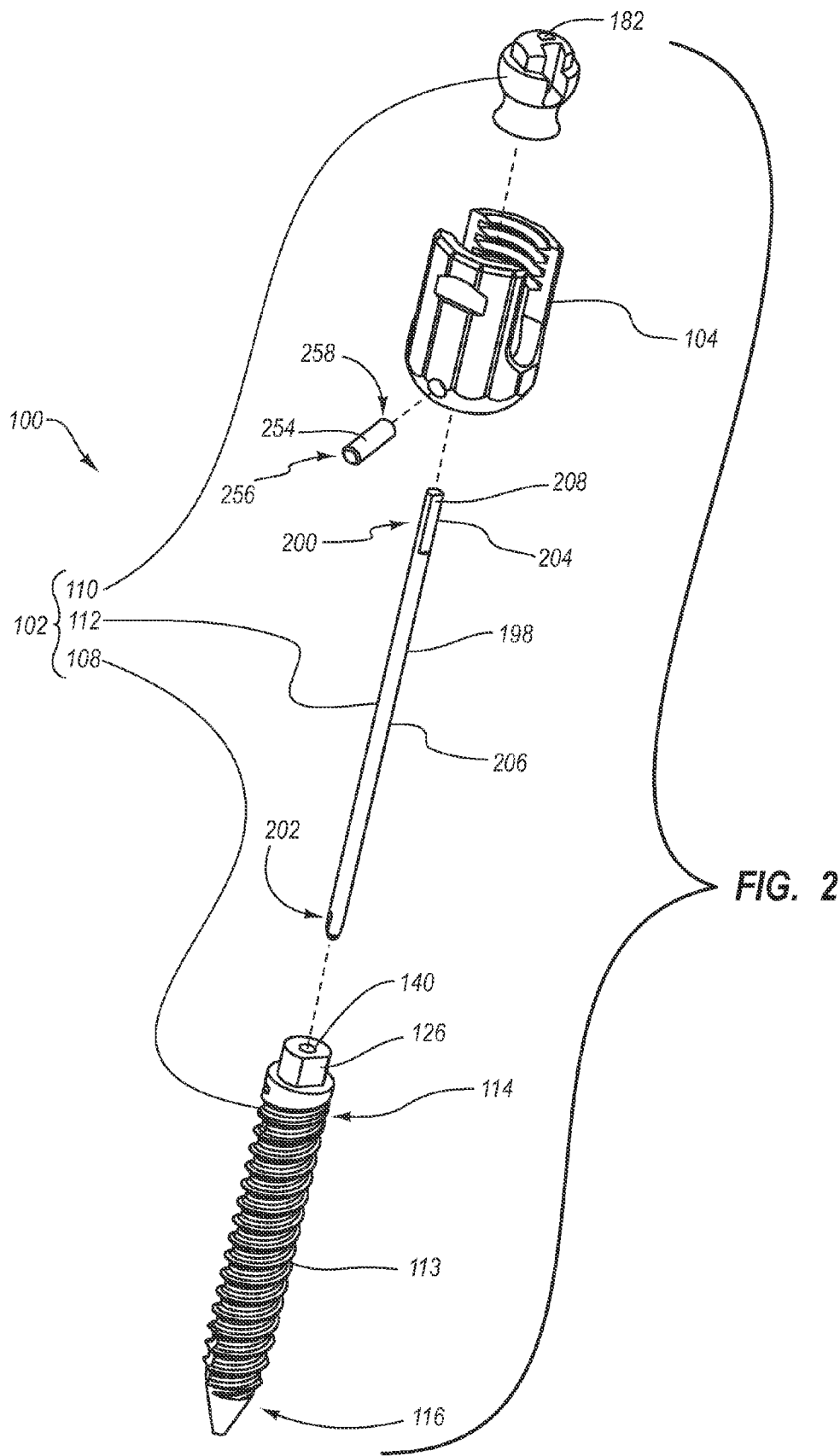
FIG. 2 is an exploded perspective view of the polyaxial bone screw shown in FIG. 1.
Figure 3:
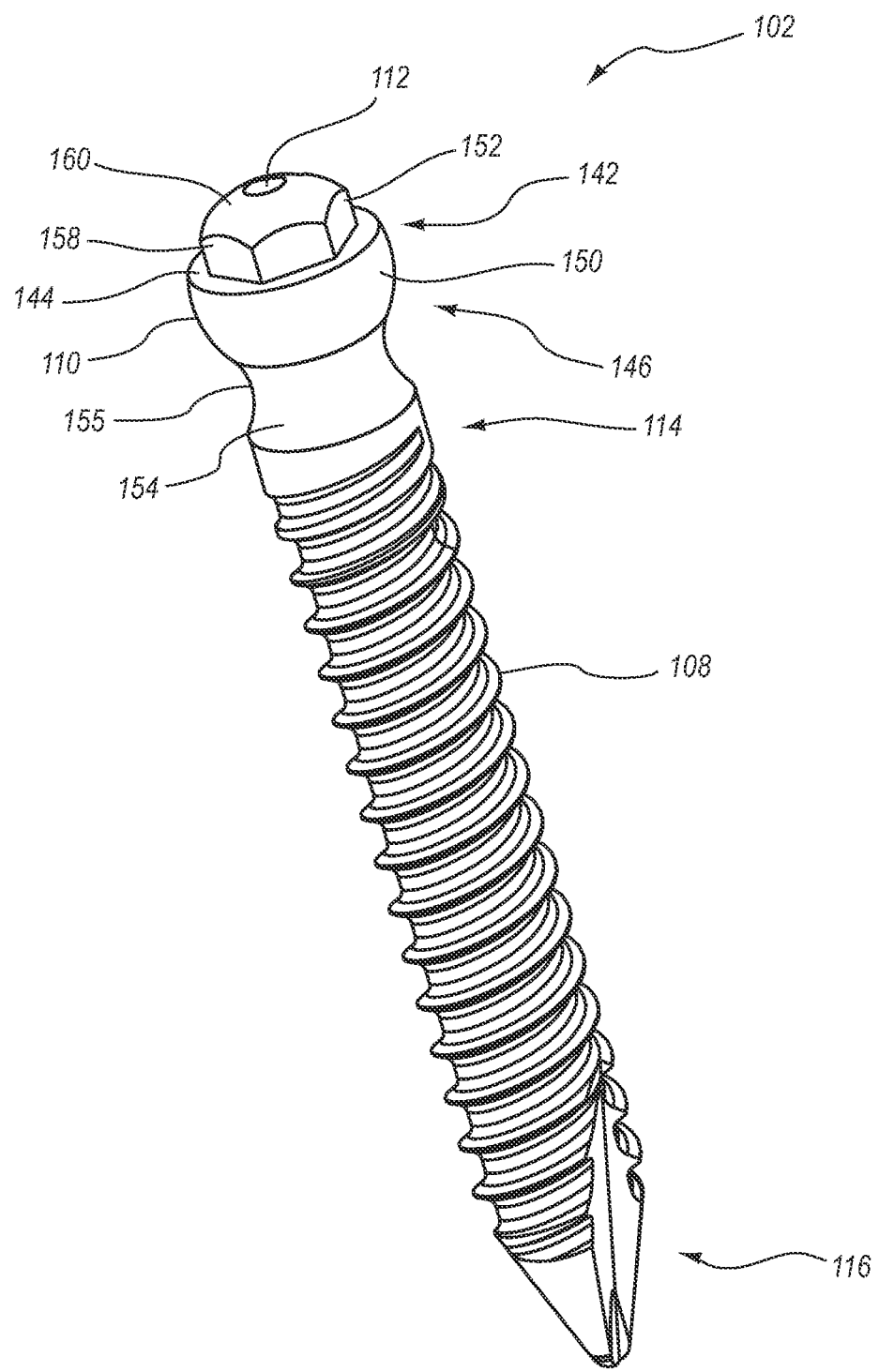
FIG. 3 is a perspective view of the assembled screw portion of the bone screw shown in FIG. 2.

As shown in FIGS. 2 and 3, screw portion 102 of bone screw 100 comprises an elongated shaft 108 having a head 110 disposed thereon with a core 112 extending longitudinally through shaft 108 and head 110.

Figure 4:
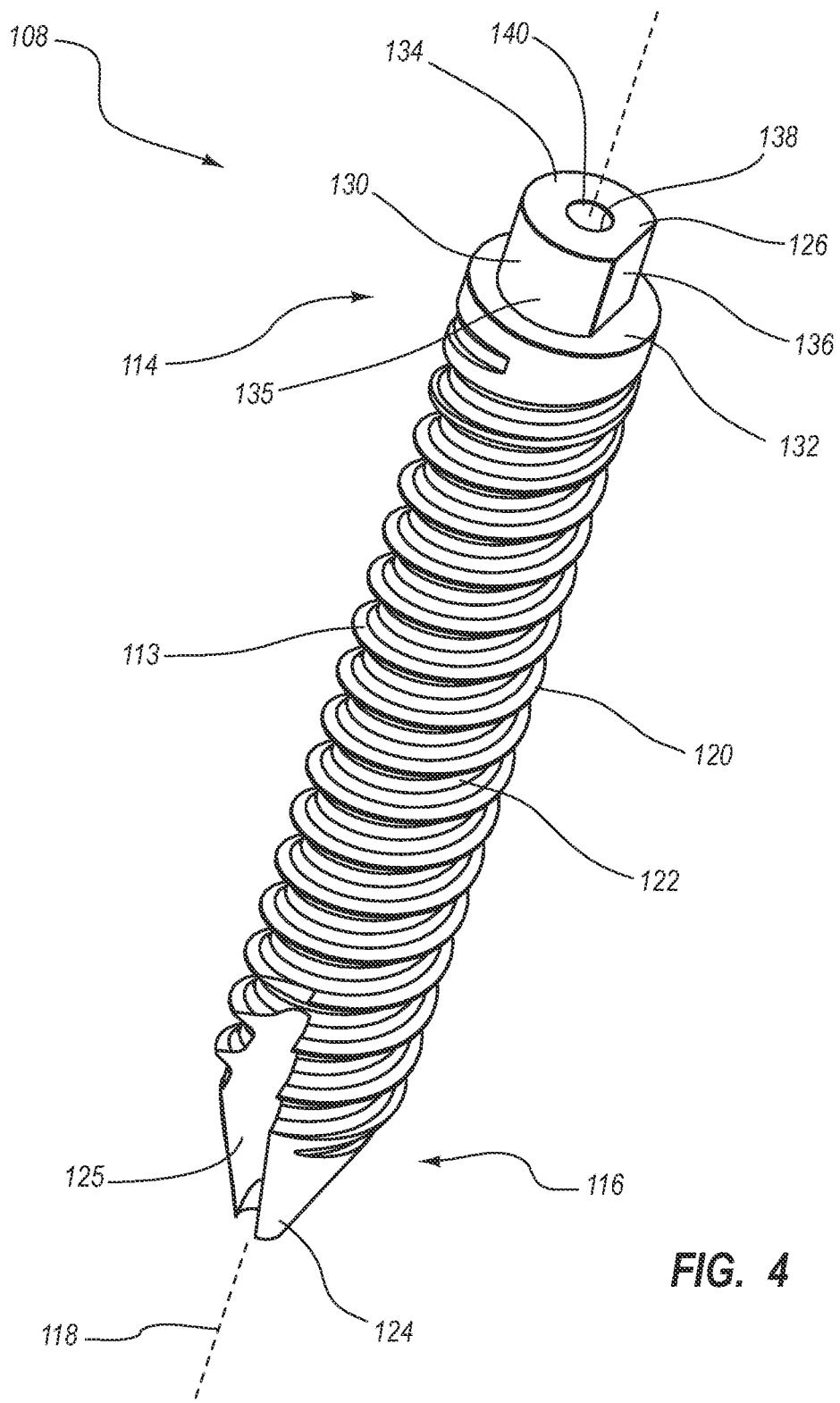
FIG. 4 is a perspective view of the shaft portion of the screw portion shown in FIG. 3.

Turning to FIG. 4, shaft 108 is elongated and has a proximal end 114 and a spaced apart distal end 116 with a central longitudinal axis 118 extending therebetween. Shaft 108 comprises an elongated shaft body 113 and an attachment member 126 formed at the proximal end thereof. Shaft body 113 has an exterior surface 122 that extends between proximal end 114 and distal end 116. One or more threads 120 helically encircle and radially outwardly project from exterior surface 122 of shaft body 113 along the length thereof. The one or more threads 120 can have a variety of different pitches and configurations, and, if desired, can be self-tapping. Proximal end 114 of shaft body 113 terminates at an end face 132 while distal end 116 of shaft body 113 terminates at a tapered tip 124. End face 132 is typically planar and disposed orthogonal to central longitudinal axis 118, although this is not required. Tapered tip 124 has a substantially conical configuration for ease in penetration into a bone or predrilled hole. A cutting edge 125 can also be disposed on the tapered portion of tip 124 to aid in cutting the bone in bone screw embodiments that are self-tapping.

Attachment member 126 centrally projects from end face 132 of shaft body 113. As discussed below in greater detail, attachment member 126 is used to engage and secure head 110 (FIG. 2) to shaft 108. As such, attachment member 126 is sized and shaped so as to fit within a complementary attachment recess 128 disposed on head 110 (see FIG. 6). In the embodiment depicted, attachment member 126 has an encircling side wall 130 that proximally extends from end face 132 of shaft body 113 to a terminal end face 134. End faces 132 and 134 are depicted as being substantially parallel with each other and orthogonal to longitudinal axis 118, although this is not required. Side wall 130 is depicted as being substantially parallel to longitudinal axis 118, but this is also not required.

In the depicted embodiment, side wall 130 of attachment member 126 comprises a substantially cylindrical portion 135 and a flat 136. Flat 136 in effect removes a portion of the rounded side of the cylinder portion 135. In an alternative embodiment side wall 130 is formed without a flat. Other cross sectional attachment shapes can alternatively be used. For example, side wall 130 of attachment member 126 can be oval, polygonal, star shaped, irregular, or the like. Other shapes are also possible.

Continuing with FIG. 4, shaft 108 includes an internal surface 138 that bounds a first passageway 140 extending longitudinally through shaft 108 between proximal end 114 and distal end 116. First passageway 140 extends along central longitudinal axis 118, through terminal end face 134 of attachment member 126 and through tapered tip 124. In the embodiment depicted, first passageway 140 has a substantially circular cross-sectional shape. Other cross-sectional shapes can alternatively be used for first passageway 140. For example, first passageway 140 can be oval shaped, star shaped, polygonal shaped, irregular or the like. First passageway 140 can also be symmetrically or non-symmetrically shaped. In alternative embodiments, first passageway 140 need not extend the full length of shaft 108. For example, first passageway 140 need not extend through tip 124.

Shaft 108 can be comprised of a radiolucent material that will allow viewing of adjacent bone or other internal structures on an X-ray photograph that are in the viewing path of shaft 108. Using radiolucent material for the shaft 108 will also minimize scattering caused by commonly used metallic or other radiopaque shafts in X-Rays, CAT scans, MRI's, and other types of imaging systems.

One example of a radiolucent material that can be used in shaft 108 is a radiolucent biocompatible fiber and adhesive matrix. In this embodiment, an adhesive is applied to one or more elongated biocompatible fibers that are then wound about core 112, a rod, or other object to form shaft 108. This is typically done by winding two or more layers of fibers about core 112 or other object. The fibers can be wound one fiber at a time or multiple fibers at a time in a fiber bundle or tow. The fibers are typically of indefinite length and are wound from a spool or other carrier and then cut when the winding is completed. Alternatively, the fibers can comprise one or more shorter fibers that are wound or otherwise disposed within shaft 108. In still other embodiments, the fibers can be included in a sheet or other structure and then wound about core 112 or other object in one or two or more layers. Various winding patterns and fiber orientation can also be used. Methods of manufacturing the shaft 108 are discussed in more detail below Many different types of biocompatible fibers and adhesives can be used to form radiolucent shaft 108. For example, the fibers can be comprised of carbon, fiberglass, poly paraphenylene terephthalamide (PPTA, more commonly known as Kevlar®), other aramids, and ceramics. Other radiolucent, biocompatible fibers having desired properties can also be used.

Although fibers having multiple different properties can be used, typical fibers have a diameter in a range between about 5 microns to about 18 microns with about 5 microns to about 7 microns being more common and a tensile strength in a range between about 300 ksi to about 1000 ksi with about 600 ksi to about 1000 ksi being more common. Other diameters and tensile strengths can be used. The fibers can be sized or unsized. By "unsized," it is meant that the fibers have not been coated with a material to improve adhesion of the resin or adhesive. If the fibers are sized, biocompatibility of the sizing needs to be considered. When bundles of fibers are used, the tow of the fibers (i.e., the number of fibers per bundle) can range from about 1 k to about 72 k with about 3 k to about 24 k being more common. Other tow ranges can also be used. In one specific embodiment, the fibers comprise a continuous high strength, PAN based carbon fiber, 34-700, 12 k (tow), "unsized". In another specific embodiment, the fibers comprise a continuous high strength, PAN based carbon fiber, 34-700, 3 k (tow), sized.

Examples of biocompatible adhesives that can be used with the fibers include thermoplastic materials, thermoset materials and ceramics. Examples of thermoplastic materials that can be used include polyester, vinylester, polycarbonate, polyetheretherketone (PEEK), polyaryletherketone (PAEK), polyethylene, polyurethane, and polyamide. Examples of thermoset materials that can be used include epoxies and polyimides. Exemplary biocompatible epoxies include the Master Bond Inc. epoxies EP42HT-2 and EP45HT MED and the Epotek epoxies 301-2 and 375. Examples of ceramics that can be used include alumina and zirconia. Other epoxies, ceramics, plastics and resins that are implantable, biocompatible, sterilizable, and have the desired strength properties can also be used. In an alternative embodiment, the radiolucent material used in shaft 108 can simply comprise the adhesive materials as discussed above without the fibers. If desired, other additives and fillers can be combined with the adhesive materials.

Returning to FIGS. 2 and 3, head 110 is disposed on proximal end 114 of shaft 108 so as to engage with attachment member 126. As shown in FIG. 3, head 110 comprises a rounded substantially semi-spherical bottom portion 150 that can bias and rotate against collar 104. Bottom portion 150 has a first end 142 on which a face 144 is formed and a second end 146. A top portion 152 centrally projects from face 144 and is shaped to allow a tool to engage and rotate screw portion 102. An annular neck 154 extends from the second end 146 of bottom portion 150 of head 110 to a bottom surface 156 (see FIG. 6). Neck 154 has an encircling exterior surface 155 having a substantially concave transverse cross section. In the depicted embodiment, top portion 152 has an encircling sidewall 158 that extends from face 144 to a top surface 160. Sidewall 158 typically has a polygonal shape so that it can mate with a driver or other tool for tightening and loosening bone screws. Other shapes, such as oval or irregular, can also be used. Alternatively, a socket can be formed within top surface 160 or on face 144 of bottom portion 150 for engaging a tool.

Figure 5:
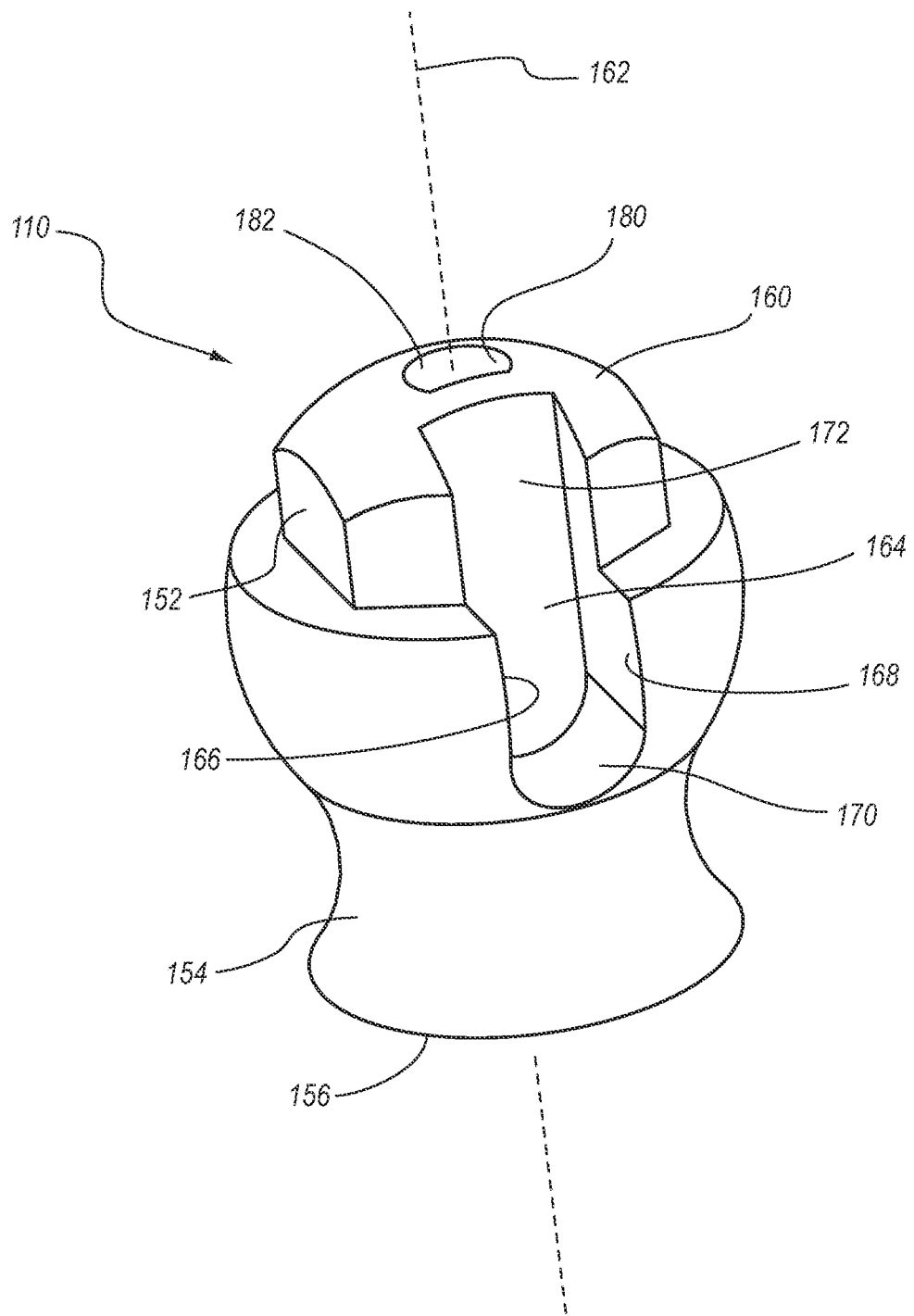
FIG. 5 is a top perspective view of the head of the screw portion shown in FIG. 3.

Turning to FIG. 5, head 110 includes a central longitudinal axis 162 extending through head 110 between top surface 160 of top portion 152 and bottom surface 156 of neck 154. When screw portion 102 is assembled, axis 118 of shaft 108 (see FIG. 4) and axis 162 of head 110 can be aligned with each other.

An engagement slot 164 is formed on head 110. Engagement slot 164 comprises a pair of opposing side walls 166 and 168 that are generally disposed in parallel planes and extend to a rounded floor 170 and a back wall 172. Back wall 172 typically intersects with floor 170 at a right angle while back wall 172 is disposed generally parallel to central longitudinal axis 162 at a distance spaced apart therefrom. In alternative embodiments, floor 170 need not be rounded but can be flat, V-shaped, or have other configurations. It is appreciated that engagement slot 164 can have a variety of different configurations and merely needs to be sized, shaped, and oriented to permit the desired pivoting of collar 104 and rotation of screw portion 102 as discussed below in greater detail.

Figure 6:
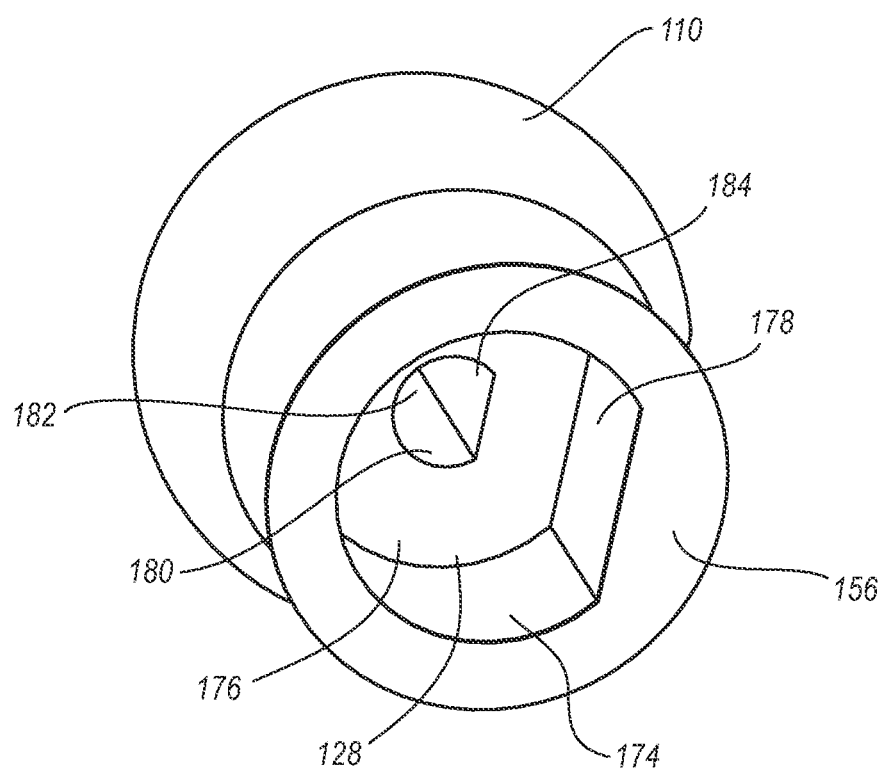
FIG. 6 is a bottom perspective view of the head of the screw portion shown in FIG. 3.

Turning to FIG. 6, attachment recess 128 is formed in bottom surface 156 of head 110 to mate with attachment member 126 of shaft 108 (FIG. 4). As such, attachment recess 128 is sized and shaped so as to receive attachment member 126. For example, in the depicted embodiment, attachment recess 128 is bounded by an encircling side wall 174 that extends from bottom surface 156 to a floor 176. Attachment recess 128 has a straight section 178 of side wall 174 corresponding to flat 136 of side wall 130 of attachment member 126. (FIG. 4) In an alternative embodiment, attachment member 126 is disposed on head 110 and attachment recess 128 is formed on shaft 108. It is appreciated that attachment member 126 and attachment recess 128 can have a variety of different configurations and merely need to be sized, shaped, and oriented to permit attachment member 126 and attachment recess 128 to selectively mate with each other when head 110 and shaft 108 are secured together, as discussed below in greater detail.

Returning to FIG. 5 in conjunction with FIG. 6, similar to shaft 108, head 110 includes an internal surface 180 bounding a second passageway 182 that extends through head 110. Second passageway 182 extends along central longitudinal axis 162, between top surface 160 and attachment recess 128 (or attachment member 126, if attachment member 126 is disposed on head 110). Second passageway 182 can be of the same cross-sectional shape as first passageway 140 or can be of a different shape. For example, in the depicted embodiment, second passageway 182 has a substantially circular cross sectional shape except for a straight portion 184 on one of the sides. Other shapes can also be used.

Head 110 can comprise a radiolucent material, such as any of those listed above for shaft 108. In one embodiment, head 110 comprises the same or different radiolucent material as shaft 108. Alternatively, head 110 can comprise a radiopaque material in place of or in addition to a radiolucent material. Examples of radiopaque metals that can be used in head 110 are titanium, stainless steel, tungsten, cobalt based alloys, cobalt chrome alloys, nickel titanium alloys such as Nitinol, platinum/iridium, gold, barium and alloys thereof. Other radiopaque materials that can be used include cortical bone and synthetic bone. The radiopaque material may also comprise the radiolucent materials discussed above having a radiopaque filler disposed therein. Other biocompatible metals and other radiopaque materials having desired properties can also be used.

Applicant notes that due to the electric potential between carbon and titanium, corrosion may occur between the two surfaces in the presence of an electrolyte. However, because the electron potential is small, the corrosion would be very small, if it occurs at all. Furthermore, the adhesive used in the matrix acts as an insulator. To combat any corrosion that may occur, anodization or passivation of the metals can be performed before assembly.

Returning to FIG. 2, core 112 comprises a slender rod having an encircling outer surface 198 that extends between a proximal end 200 and an opposing distal end 202. Core 112 is designed to be disposed within first and second passageways 140 and 182 of assembled shaft 108 and head 110, respectively. As discussed below, this can be accomplished by forming the shaft 108 about core 112 or by inserting core 112 into passageway 140 after the passageway 140 has been formed. It is appreciated that core 112 need not extend all the way through shaft 108 but can be disposed only along a portion thereof. Thus, both core 112 and first passageway 140 can extend only along a portion of shaft 108.

Figure 7:
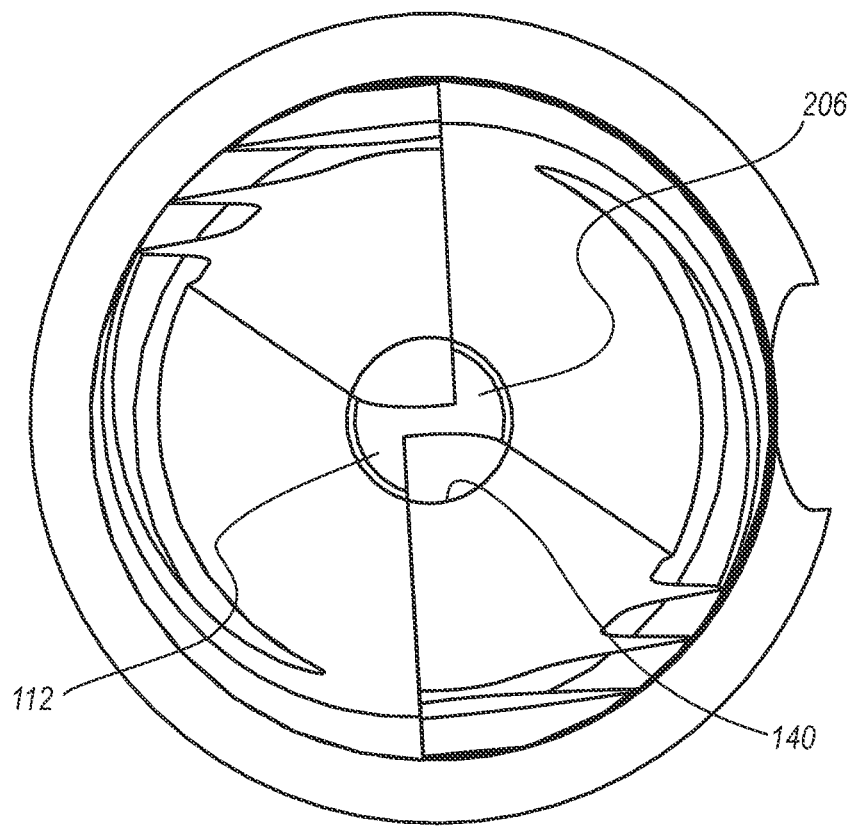
FIG. 7 is a bottom plan view of the assembled screw portion shown in FIG. 3.

Core 112 comprises a head portion 204 at proximal end 200 and a shaft portion 206 at distal end 202. Head portion 204 of core 112 is shaped to be disposed within second passageway 182 of head 110 and shaft portion 206 is shaped to be disposed within first passageway 140 of shaft 108. For example, in the embodiment depicted, shaft portion 206 has a substantially circular cross section (see FIG. 7) to match the circularly shaped first passageway 140, and head portion 204 has a substantially circular cross section with a segment removed to form a straight section 208 so as to match the shape of second passageway 182. In some embodiments, the cross-sectional shapes of head portion 204 and shaft portion 206 comprise the same shape.

Figure 8A:
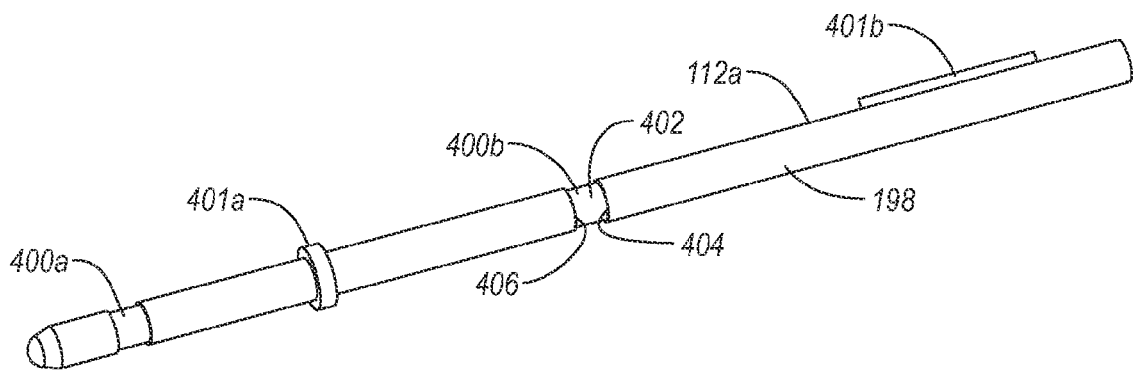
FIGS. 8A-8C are perspective views of alternative embodiments of cores.

Other variations can also be incorporated into the head portion 204 and/or the shaft portion 206 of core 112. For example, one or more channels or projections can be incorporated into core 112 to increase engagement between core 112 and shaft 108 or head 110, thereby minimizing the potential for separation therebetween. In FIG. 8A, a core 112a includes two channels 400a and 400b longitudinally spaced apart from each other. Each channel 400 is bounded by an encircling side wall 402 having a substantially circular cross section with a diameter less than the diameter of outer surface 198. As such, channels 400 are also bounded by a first end face 404 and a second end face 406 that extend between the outer surface 198 and the sidewall 404 at either end of channels 400. The end faces can be substantially orthogonal to the outer surface 198 (as shown), or form some other angle with the outer surface 198. Although FIG. 8A shows two channels 400, it is appreciated that one or three or more channels 400 can alternatively be used.

Furthermore, instead of or in conjunction with channels 400, one or more projections can be formed along core 112a. The projections can comprise a flange 401a that encircles or partially encircles core 112a, one or more ribs 401b that extend along core 112a, knobs, or projections having a variety of other configurations. Instead of having a diameter less than the diameter of outer surface 198, the projections 401 have a diameter greater than the diameter of outer surface 198. As such, the projections extend out from outer surface 198.

The sizes and locations of channels 400 or projections 401 can vary widely. In some embodiments, the locations of the channels or projections are chosen so as to provide a length indicator when the core 112a is viewed on an X-ray. That is, when viewed on an X-ray, the channel or projection can identify to the doctor a predefined length of the core 112a.

Figure 8B:
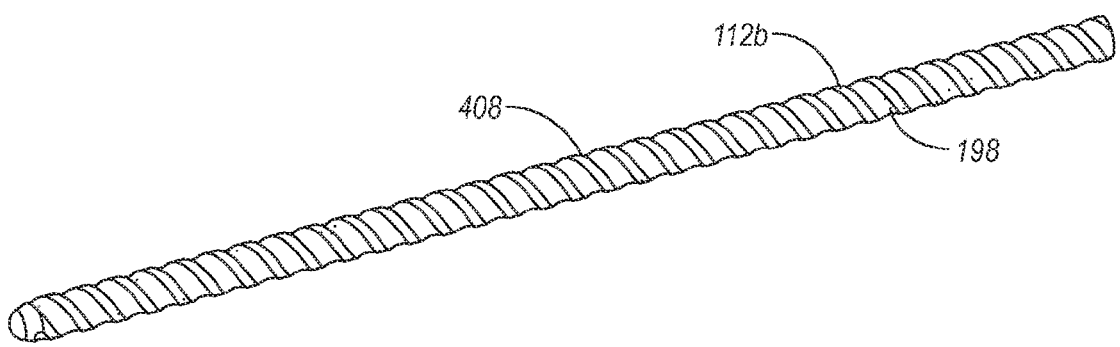

FIG. 8B shows another surface shape variation incorporated into a core 112b to help minimize the potential for separation from shaft 108 or head 110. In FIG. 8B, a helical thread 408 is formed on outer surface 198. If the first and second passageways 140 and 182 are likewise threaded, the shaft 108 and/or the head 110 can be threaded onto the core 112 during manufacturing and assembly, if desired. The size, shape, and pitch of the helical thread can vary.

Figure 8C:
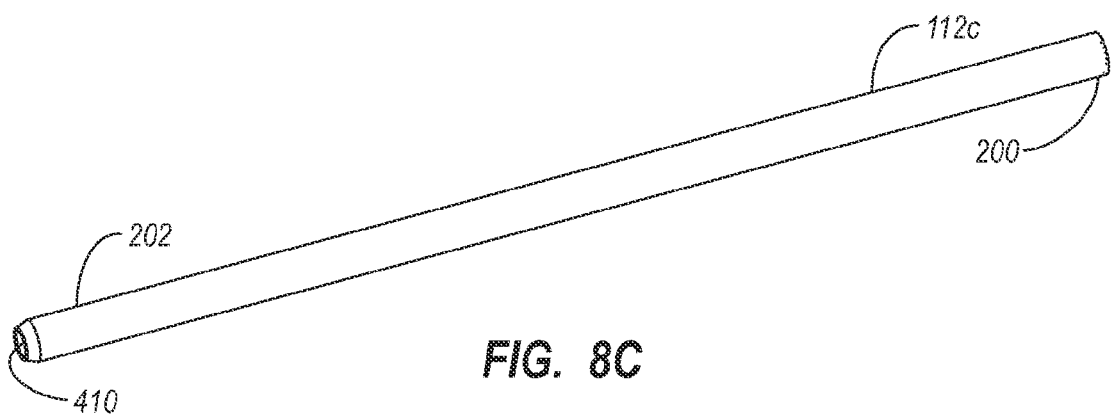

FIG. 8C shows another variation incorporated into a core 112c. In FIG. 8C, core 112c has a cannula 410 that longitudinally extends completely through core 112c between proximal end 200 and distal end 202. Cannula 410 can be used during implantation to pass a guidewire or other surgical device through is assist in positioning bone screw 100 and/or can be used for performing other surgery techniques. The cross sectional size and shape of cannula 410 can vary, depending on the cross-sectional size and shape of core 112c.

It is appreciated that any of the core variations described above can be combined, if desired, in the same core 112. For example, in one embodiment, a cannula and one or more channels or projections could be included in the same core, while in another embodiment a cannula could be included in a threaded core. Other combinations are also possible.

Figure 9A:
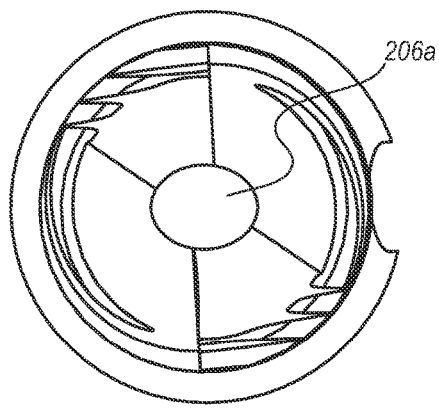
FIGS. 9A-9D are cross-sectional bottom views of alternative embodiments of screw portions of bone screws.
Figure 9B:
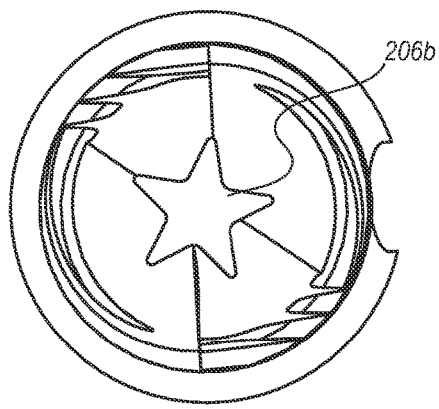
Figure 9C:
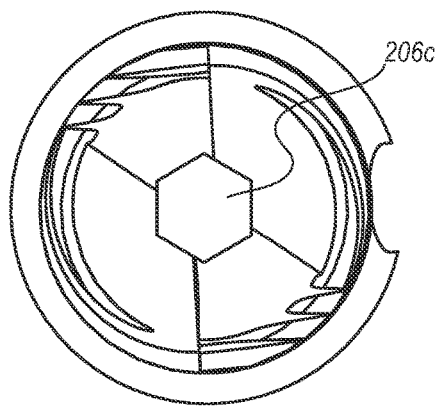
Figure 9D:
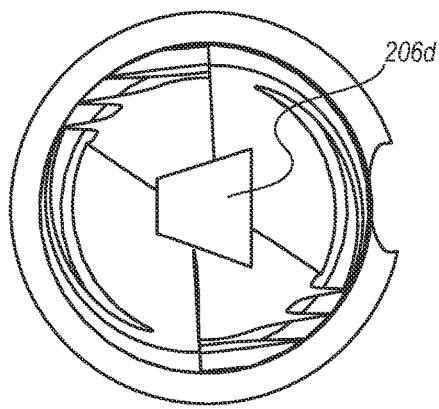

Various geometric cross sectional shapes can alternatively be used for the head portion 204 and/or the shaft portion 206 of core 112. For example, FIGS. 9A-9D disclose various embodiments of shaft portion 206 having different cross sectional shapes. FIG. 9A shows an embodiment in which shaft portion 206a is oval shaped. FIG. 9B shows an embodiment in which shaft portion 206b is generally star shaped. FIG. 9C shows an embodiment in which shaft portion 206c is generally polygonal shaped. In some embodiments head portion 204 and/or shaft portion 206 have a symmetrical cross sectional shape, such as shaft portion 206c shown in FIG. 9C; in other embodiments head portion 204 and/or shaft portion 206 have a non-symmetrical cross sectional shape, such as shaft portion 206d shown in FIG. 9D. Head portion 204 and/or shaft portion 206 can also use a combination of curved and linear segments, such as head portion 204 shown in FIG. 2. It is appreciated that the aforementioned core shapes are exemplary only and that other shapes, that are typically non-circular, can alternatively be used. It is appreciated that the passageways in shaft 108 and head 110 in which core 112 is received can have the same complementary configuration as core 112. One benefit of producing core 112 with a non-circular configuration is that greater engagement can be formed between core 112 and screw portion 102, thereby minimizing the potential for separation therebetween.

Core 112 typically has a maximum outer diameter in a range between about 1 mm to about 3.5 mm, with about 2 mm to about 3 mm being common. In one embodiment, core 112 has a maximum diameter that is less than about 3 millimeters and more commonly less than about 2 millimeters. Other diameters can also be used.

Core 112 is typically comprised of a radiopaque material, such as those previously discussed with regard to head 110. Core 112 can be comprised of the same radiopaque material as head 110 or can be comprised of a different radiopaque material. One advantage of using a radiopaque material in core 112 while using a radiolucent material in shaft 108 is that only the thin core 112 will be seen on an X-ray during and after implantation of screw portion 102. This aids the surgeon in positioning screw portion 102 when implanting screw portion 102, yet allows other internal body structures to be viewed by X-ray during and after screw portion 102 implantation. Where core 112 is comprised of a radiopaque material, core 112 comprises a marker for screw portion 102.

In alternative embodiments, core 112 can be comprised of a radiolucent material, such as those previously discussed with regard to shaft 108. For example, core 112 can comprise an adhesive as discussed with regard to shaft 108 that is free of fibers or that that has elongated or chopped fibers embedded therein. In these embodiments, screw portion 108 can be completely free of any radiopaque markers or, alternatively, one or more radiopaque markers can be added thereto, as discussed below. In some embodiments, core 112 is comprised of the same material as shaft 108. In still other embodiments, core 112 can be comprised of both radiolucent and radiopaque materials. For example, small pieces of radiopaque material, such as small pieces of metal, i.e., metal particles, fibers, and/or spheres, can be embedded within or spaced between a matrix of a radiolucent material such as an epoxy.

In one method of manufacture, the radiolucent fibers and adhesive can be wound around a removable rod. Once shaft portion 108 is formed by the radiolucent material about the rod, the rod is removed leaving passageway 140. Passageway 140 can then be backfilled with a radiolucent material as discussed above or a combination of radiolucent and radiopaque materials. As a result, if desired, radiopaque material can be positioned at a defined location or at select, spaced apart locations along passageway 140 to form one or more defined markers under X-ray.

Based on the foregoing, it is appreciated that inventive screw portion 102 can be comprised of a radiolucent shaft 108 with a radiopaque core 112; a radiolucent shaft 108 with a radiolucent core 112; and/or a radiolucent shaft 108 with a core 112 having both radiolucent and radiopaque sections. Other material combinations can also be used. In combination with each of the above three alternative designs, it is appreciated that radiopaque markers can be formed on or along the radiolucent shaft 108. Such markers can further aid the surgeon in the implantation and positioning of screw portion 102.

Figure 10:
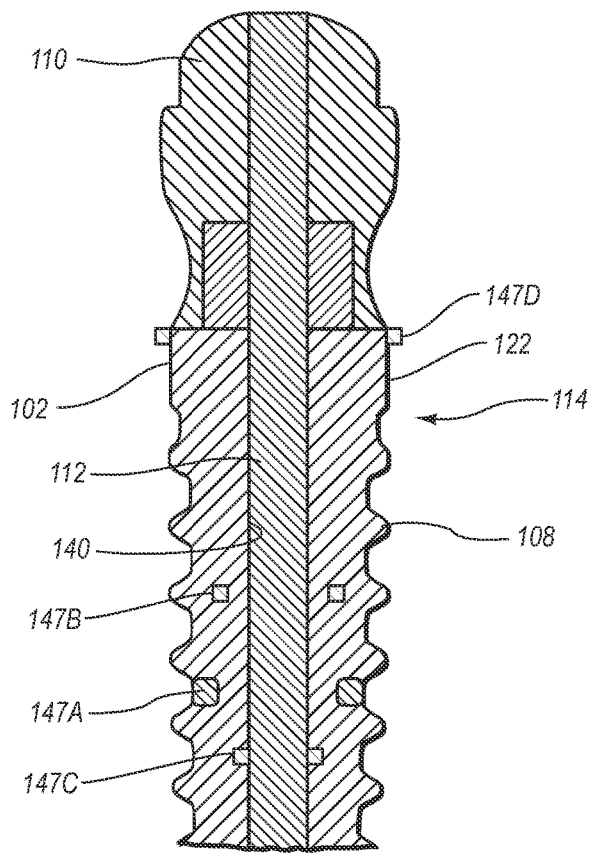
FIG. 10 is a cross sectional side view of an assembled screw portion according to one embodiment having a positioning ring disposed within the shaft.

One example of a radiopaque marker is an encircling marker disposed within or on shaft 108 such that the marker is spaced apart or is disposed directly against core 112. For example, FIG. 10 shows an embodiment of a screw portion 102 in which a biocompatible positioning marker 147A is embedded within shaft 108 between proximal end 114 and distal end 116. In the depicted embodiment, positioning marker 147A can comprise a ring that completely encircles passageway 140 or a partial ring that partially encircles passageway 140. In other embodiments, positioning marker 147A can be linear or any other desired shape. Each positioning marker 147A can be positioned so as to be exposed on the exterior surface of shaft 108 (such as positioning marker 147A), completely embedded within shaft 108 (such as positioning marker 147B), positioned against core 112 (such as positioning marker 147C), or can extend between core 112 and the exterior surface of shaft 108. Furthermore, a positioning marker 147D, such as in the form of a ring or other structure, can be disposed on the exterior surface 122 of shaft 108. This can be accomplished by welding, crimping, adhering, or otherwise securing positioning marker 147D on exterior surface 122. Other configurations and placement of positioning markers 147 can also be used. For example, a positioning marker can form a helix that spirals in one or more partial or complete revolutions about passageway 140 or can form a linear strand that extends along the length of shaft 108.

Positioning markers 147 are comprised of a radiopaque material so as to be viewable on an X-ray photograph. As such, positioning markers 147 can be comprised of the same types of radiopaque materials discussed above with regard to head 110. During implantation and positioning of screw portion 102, the X-ray image of positioning markers 147 can help the physician determine the position and orientation of screw portion 102.

In one embodiment, a positioning marker 147 is positioned about midway between proximal end 114 and distal end 116 of shaft 108. In other embodiments, a positioning marker 178 is positioned substantially closer to proximal end 114 or distal end 116 or at any desired location. In some embodiments, as shown in FIG. 10, it is appreciated that two or more positioning markers 147 can be positioned along shaft 108 at spaced apart locations.

Figure 11:
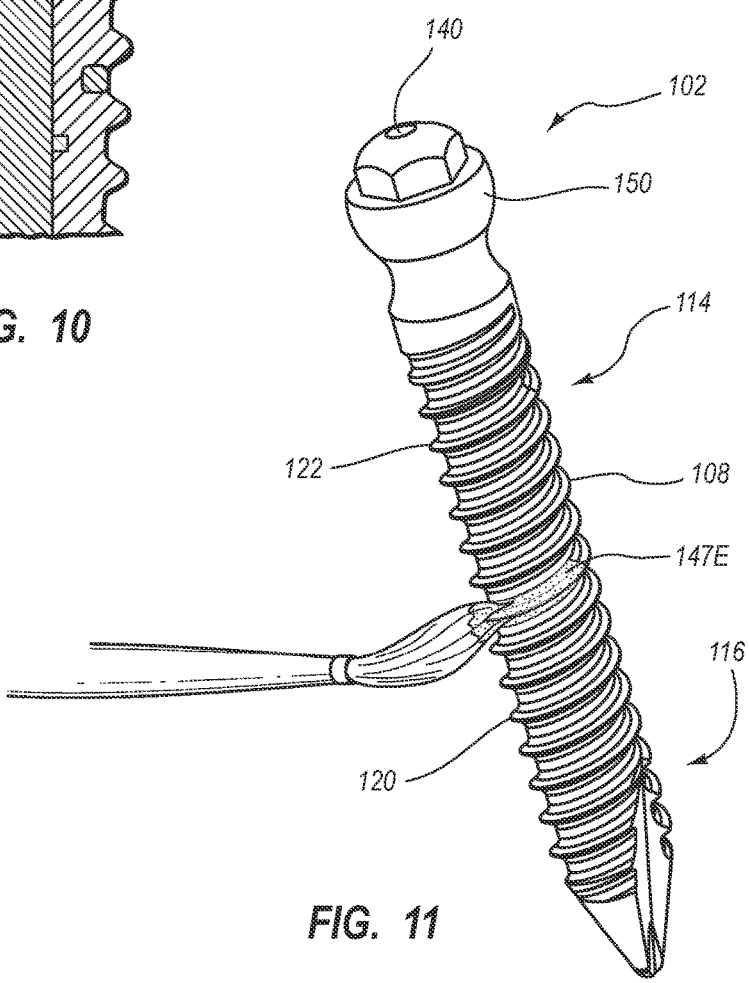
FIG. 11 is a perspective view of an assembled screw portion according to one embodiment having a ring layer painted thereon.

Depicted in FIG. 11 is another embodiment of a positioning marker 147E. Positioning marker 147E is again comprised of a radiopaque material but in this embodiment is in the form of paint or ink that is painted or printed onto exterior surface 122 of shaft 108. Positioning marker 147E can be used in place of or in combination with one or more additional positioning markers as discussed above. Positioning marker 147E can form a continuous ring that encircles shaft 108 or can be any other type of configuration such as linear, semi-circular, helical configuration or the like. For example, positioning marker 147E can be painted on a single helical revolution of threads 120. Furthermore, a single or two or more spaced apart positioning markers 147E can be formed along shaft 108.

It is appreciated that radiopaque markers can be any desired shape and be located at any position or orientation that will produce a desired marking. For example, in other embodiments, pieces of radiopaque material can be embedded within the shaft matrix as radiopaque positioning markers. These pieces can comprise small or large particles that are placed within the shaft matrix during manufacture either randomly or in a particular pattern. Many different shapes and patterns can be used for these radiopaque positioning markers. Also, these pieces of radiopaque material can be used with or without any of the other types of positioning markers discussed above.

Figure 12:
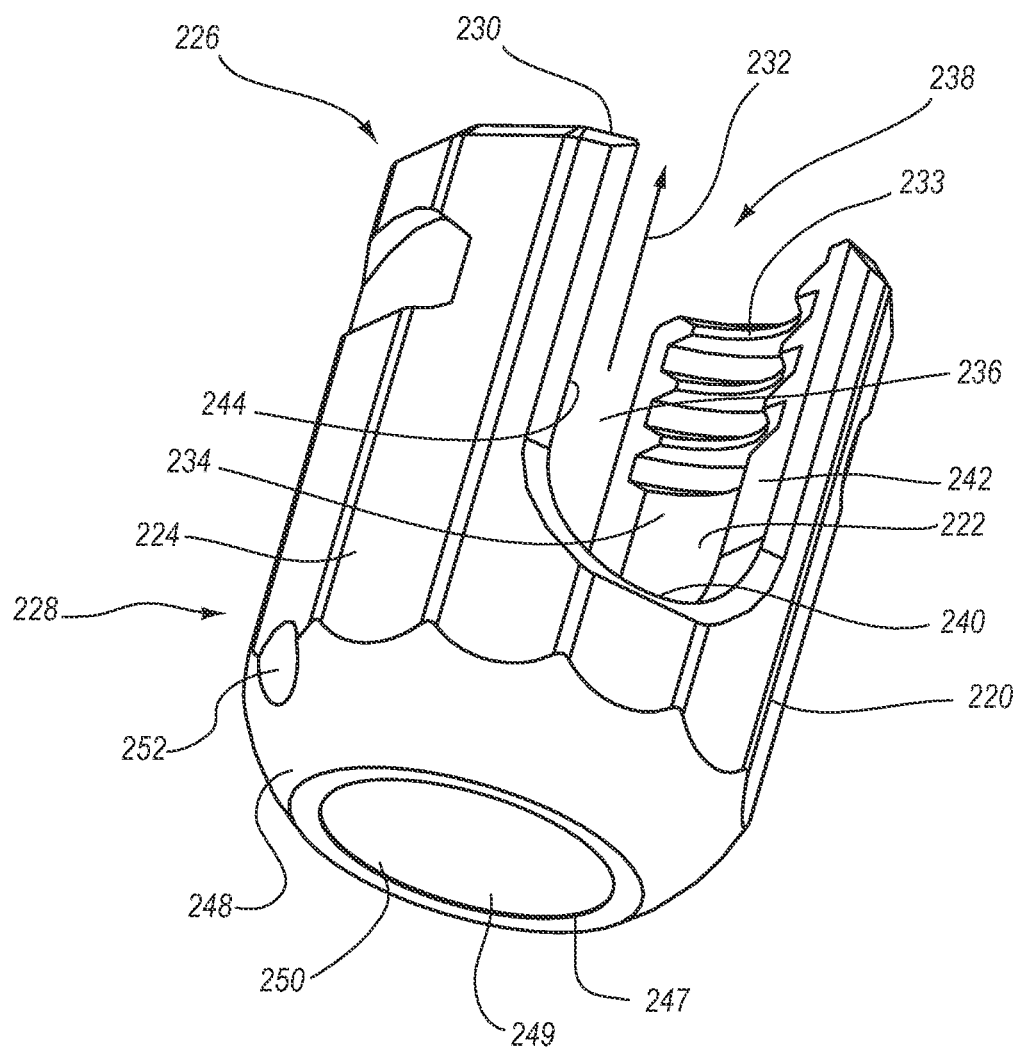
FIG. 12 is a perspective view of the collar shown in FIG. 2.

Turning to FIG. 12, collar 104 comprises a tubular side wall 220 having an interior surface 222 and an exterior surface 224 that each extend between a first end 226 and an opposing second end 228. First end 226 terminates at a terminal end face 230. Interior surface 222 bounds a longitudinal passage 232 that longitudinally extends through collar 104. Internal threads 233 are formed on interior surface 222 at or toward first end 226.

Side wall 220 is formed having a pair of channels 234 and 236 that are disposed on opposing sides of side wall 220 and that transversely extend through side wall 220. In the embodiment depicted, channels 234 and 236 each have a substantially U-shaped configuration. Each channel 234 and 236 has an open mouth 238 that extends through end face 230 and an opposing floor 240 that is rounded. Each channel 234 and 236 is configured so that stabilizing rod 107 (FIG. 1) can be received therein. In alternative embodiments, floor 240 need not be rounded but can be flat, V-shaped, or have other configurations. Each of channels 234 and 236 is also bounded by opposing side surfaces 242 and 244. Although side surfaces 242 and 244 are shown as being in substantially parallel alignment, in alternative embodiments side surfaces 242 and 244 can be designed to diverge or converge as they project away from floor 240. Other configurations can also be used. Channels 234 and 236 form a portion of a transverse passage that transversely extends through collar 104, as identified by arrow 246 (see FIG. 1).

As shown in FIG. 12, collar 104 further comprises a shoulder 248 that downwardly and radially inwardly projects from second end 228 of side wall 220. Shoulder 248 terminates at an inside edge 247 that bounds an opening 249. Opening 249 forms part of a longitudinal passage that also extends through collar 104, as identified by arrow 232, and that orthogonally intersects with transverse passage 246 (FIG. 1).

Figure 13:
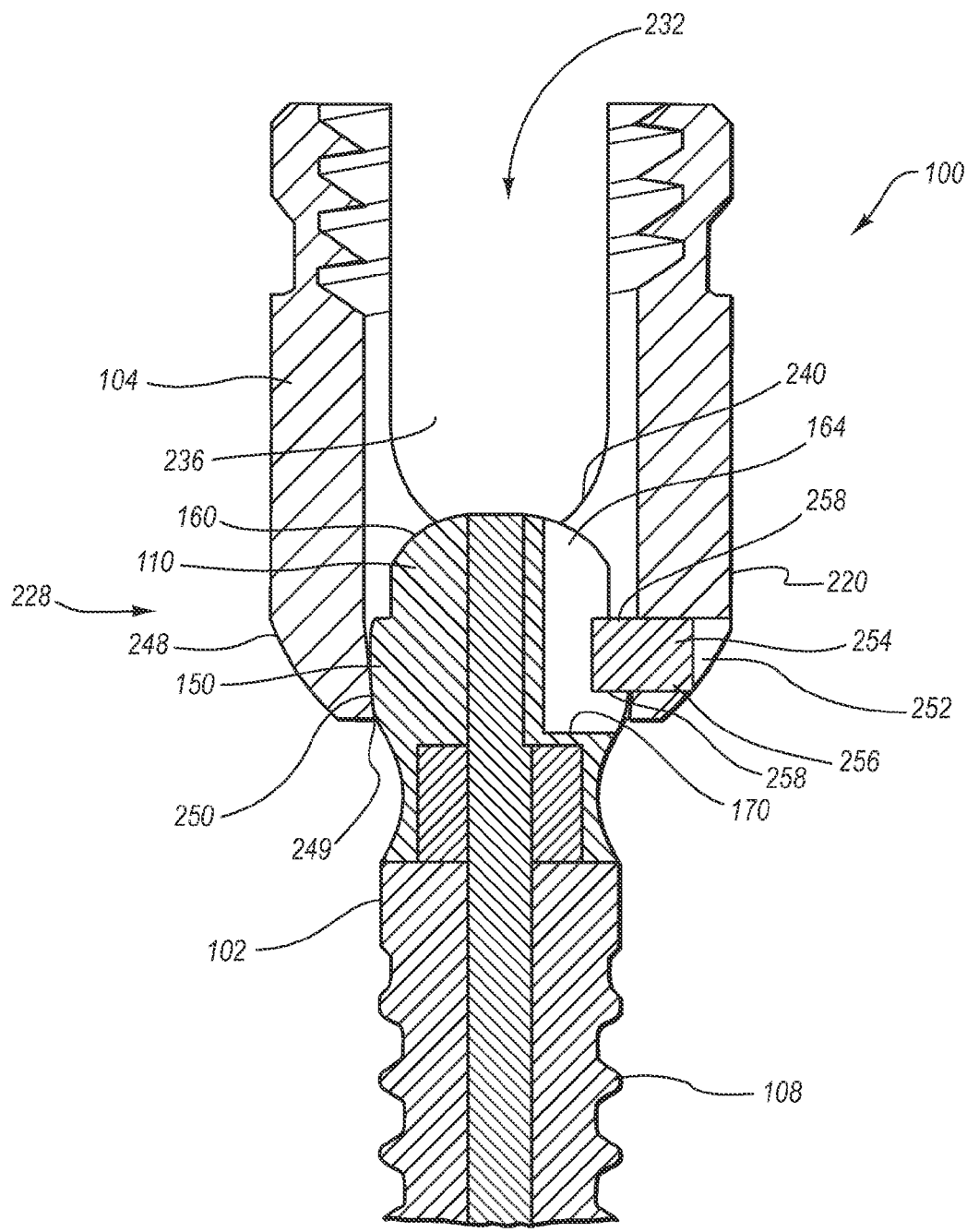
FIG. 13 is a cross sectional side view of a portion of the assembled polyaxial bone screw shown in FIG. 1.

Shoulder 248 has a tapered interior surface that forms an annular seat 250. As discussed below in greater detail, bottom portion 150 of head 110 of screw portion 102 (FIG. 3) rests against seat 250 so that collar 104 can pivot relative to screw portion 102. In this regard, as depicted in FIG. 13, bottom portion 150 of head 110 has a maximum diameter larger than opening 249 of collar 104 so that head 110 cannot pass therethrough. It is also noted that when head 110 is received within opening 249, top surface 160 of head 110 projects slightly above floor 240 of channels 234 and 236 of collar 104. As a result, as discussed further below, when stabilizing rod 170 (FIG. 1) is received within channels 234 and 236, stabilizing rod 170 biases against top surface 160 of head 110 so as to wedge head 110 within opening 249 and thereby lock screw portion 102 relative to collar 104.

As also depicted in FIG. 13, a pin hole 252 transversely extends through side wall 220 and/or shoulder 248 at second end 228 of side wall 220. Although not required, pin hole 252 is typically disposed orthogonal to transverse passage 246. As also discussed below in greater detail, pin hole 252 is adapted to receive a pin 254 which has a first end 256 and an opposing second end 258. Collar 104 and pin 254 are typically comprised of a radiopaque material such as those previously discussed with regard to core 112. In alternative embodiments, however, collar 104 and/or pin 254 can be comprised of a radiolucent material, such as those previously discussed with regard to shaft 108.

Returning to FIG. 1, fastener 106 comprises a locking screw 270 having an encircling side wall 272 that extends between a top end face 274 and an opposing bottom end face 276. Optionally, movably attached to bottom end face 276 of locking screw 270 is an alignment cap 278 having a substantially U-shaped channel 280 extending transversally therethrough. Channel 280 is bounded by two side surfaces 286 and 288. Alignment cap 278 is rotatably attached to locking screw 270 so that as locking screw 270 is rotated, alignment cap 278 can remain rotationally stationary so as to bias against rod 107.

Radially outwardly projecting from side wall 272 of locking screw 270 so as to encircle locking screw 270 are one or more helical threads 282. Threads 282 of locking screw 270 are configured to threadedly engage with internal threads 233 of collar 104 (FIG. 12). Recessed on top surface 274 of locking screw 270 is a polygonal socket 284 adapted to receive a driver. Accordingly, once stabilizing rod 107 is disposed within transverse passage 246 of collar 104, locking screw 270 can be screwed into longitudinal passage 232 of collar 104 so that fastener 106 biases stabilizing rod 107 against head 110 of screw portion 102. If alignment cap 278 is used, surfaces 286 and 288 of the U-shaped channel 280 bias against stabilizing rod 107; otherwise bottom end face 276 of locking screw 270 biases against stabilizing rod 107. In this configuration, stabilizing rod 107 is secured from unwanted movement by being compressed between fastener 106 and head 110 of screw portion 102 and/or between fastener 106 and floor 240 of channels 234 and 236. Furthermore, as stabilizing rod 107 pushes against head 110, head 110 is wedged against seat 250 of collar 104, thereby also locking collar 104 relative to screw portion 102.

Collar 104 and fastener 106 are simply one example of a collar and fastener that can be used with screw portion 102 described herein. Other collars and associated fasteners can alternatively be used, such as the collars and fasteners described in U.S. patent application Ser. No. 11/863,133, filed Sep. 27, 2007, the entirety of which reference is incorporated herein by specific reference.

Methods of manufacturing and assembling the screw portion 102 and bone screw 100 will now be discussed. It is appreciated that while reference is made to screw portion 102 and its corresponding components, the methods of manufacturing and assembly given below can also be used with the other embodiments disclosed herein or otherwise encompassed by the invention. To manufacture screw portion 102, core 112 is formed from a radiopaque material, a radiolucent material, or a combination of such materials. Examples of such materials are discussed above. Core 112 can be formed by any conventional method known in the art.

Shaft 108 is then formed about shaft portion 206 of core 112 to produce a blank 292, as shown in FIGS. 14-16. Blank 292 can be formed in a number of ways. For example, blank 292 can be formed by winding a fiber and adhesive mixture about core 112 to produce a fiber and adhesive matrix. For example, in the embodiment depicted in FIG. 14, a filament winding process is used as is known in the art. In this process, filaments or fibers 294 are wound under tension over the shaft portion 206 of core 112. Core 112 rotates while a carriage (not shown) moves back and forth along the longitudinal direction of core 112, laying down fibers 294 in a desired pattern. Fibers 294 are coated with an adhesive as the fibers 294 are wound about core 112. Many types of biocompatible fibers and adhesives can be used, as discussed above. If positioning marker 147 (such as marker 147A-C in FIG. 10) is used, the positioning marker 147 can be positioned in its desired location during the filament winding process so that positioning marker 147 becomes enveloped by the outer layers of fibers 294. The marker can also be positioned before or after the winding process. The winding process continues until the diameter of the blank 292 is equal to or greater than the desired diameter of the finished shaft 108 of screw portion 102. Blank 292 is then allowed to cure or harden. If required, blank 292 can be placed in an oven during the curing process.

In an alternative embodiment, blank 292 is formed using a roll wrap or table wrap process, as depicted in FIG. 15. In this process, one or more sheets 296 of fiber are coated with the adhesive. Many types of biocompatible fibers and adhesives can be used, as discussed above. If required, the coated sheet or sheets 296 are then allowed to partially cure. Once the desired amount of partial curing has been obtained, the sheet or sheets 296 are then wrapped about the shaft portion 206 of core 112 to produce a fiber and adhesive matrix. Again, if a positioning marker 147 (FIG. 11) is used, it can be positioned in its desired location during the wrapping process so that positioning marker 147 becomes enveloped by the outer layers of sheets 296. That is, multiple different layers can be wrapped on top of each other. The marker can also be positioned before or after the wrapping. The wrapping continues until the diameter of the blank 292 is greater than or equal to the desired diameter of the finished shaft 108 of screw portion 102. Blank 292 is then allowed to cure in a similar manner to the filament winding process, described previously.

It is also appreciated that non-winding methods can also be used for forming blank 292 about core 112. For example, compression, injection, rotational and other molding processes can be used to mold an adhesive, a fiber/adhesive mixture, or a mixture of an adhesive and other types of fillers about core 112. In this embodiment, the fibers can be short or chopped fiber pieces that are distributed throughout the adhesive. As another alternative, shaft 108 can be formed about core 112 by a direct or indirect extrusion process, where the fiber/adhesive matrix or other adhesive matrix is extruded about core 112. Other known methods can alternatively be used to form blank 292.

As the fibers 294 or sheets 296 are only wound around shaft portion 206 of core 112, the head portion 204 of core 112 remains open and uncovered, as shown in FIG. 16. To allow for a better bond between core 112 and the wound fiber and adhesive matrix, the surface of core 112 can be etched or otherwise abraded before the fibers 294 or sheets 296 are wound thereon. This can be accomplished by sand blasting, rubbing with sandpaper, chemical etching, or other known roughening process, if desired.

Once the blank 292 has been formed and allowed to cure, a grinder or other finishing process can be used, if desired, to smooth out or cut down any sharp edges remaining on the exterior surface 298 of the blank 292 to form the exterior surface 122 of shaft 108. Attachment member 126 and helical threads 120 (FIG. 4) are then formed on the exterior surface 298 of the blank 292 to further form shaft 108. This can be accomplished by removing a portion of the exterior surface 298 of the blank 292 by using a grinder, lathe, or other cutting tool as is known in the art. Other methods of forming attachment member 126 and threads 120 can alternatively be used. If positioning marker 147D or 147E is used (FIGS. 10 and 11), it is positioned or painted on the exterior surface 122 of shaft 108 after blank 292 has been processed.

Tapered tip 124 (FIG. 4) can also be formed at the distal end of the shaft 108, if desired. In one embodiment, tapered tip 124 is formed by removing a portion of the exterior surface 298 of the blank 292. Any other features, such as those needed for self tapping, can also be formed if desired.

In an alternative method of manufacturing stabilizing screw portion 102, shaft 108 can initially be formed by winding a radiolucent fiber/adhesive matrix about a removable core. In contrast to prior embodiments, however, removable core is then slid out of shaft 108. The remaining passageway 140 can then be backfilled by injecting a radiolucent material, such as an epoxy or other adhesive, or a combined radiolucent and radiopaque material into passageway 140. Alternatively, a radiolucent core can be slid into the passageway and secured in place by an adhesive or other method of securing. As a result, the entire shaft and core are radiolucent. Again, any number or type of radiopaque positioning marker can be used.

Figure 17:
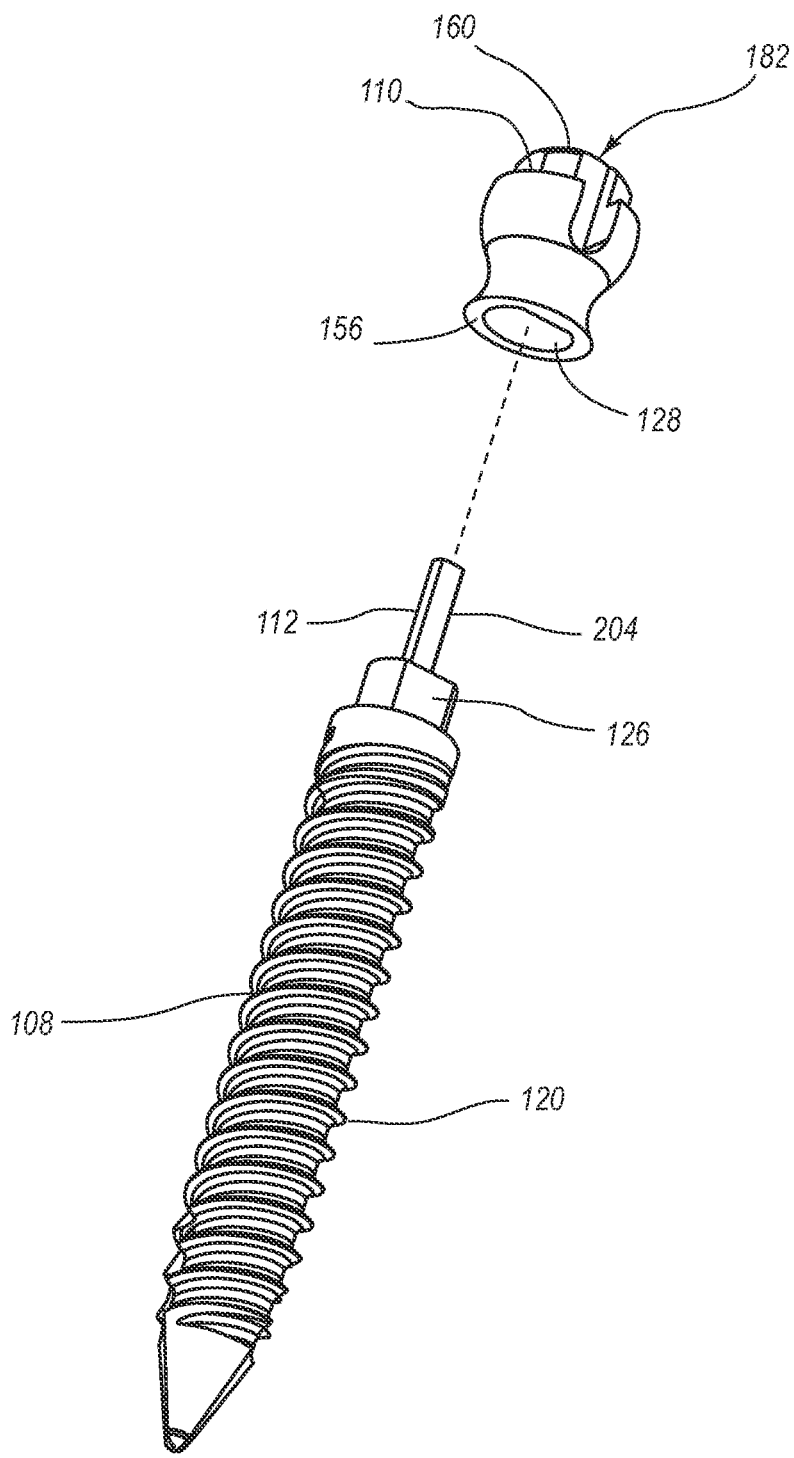
FIG. 17 is a perspective view of the screw portion shown in FIG. 3 in a partially assembled state.

Turning to FIG. 17, once attachment member 126 and threads 120 have been formed on the shaft 108, head 110, which has been previously formed, is then attached to the threaded shaft 108. To do this, bottom surface 156 of head 110 is positioned adjacent head portion 204 of core 112 so that second passageway 182 of head 110 aligns with core 112. Head 110 is then advanced toward shaft 108 so that head portion 204 of core 112 is received within second passageway 182. Head 110 is further advanced along core 112 until attachment member 126 is received within attachment recess 128. Head 110 is then rigidly secured to core 112 and to shaft 108 by a securing method known in the art, such as by adhesive, laser welding, and/or other known method. For example, in addition to using an adhesive between head 110 and shaft 108 and between head 110 and core 112, if desired, the exposed end of core 112 can be directly welded to head 110. Any portion of core 112 that extends out of second passageway 182 and past top surface 160 of head 110 can be cut off, if desired.

Figure 18:
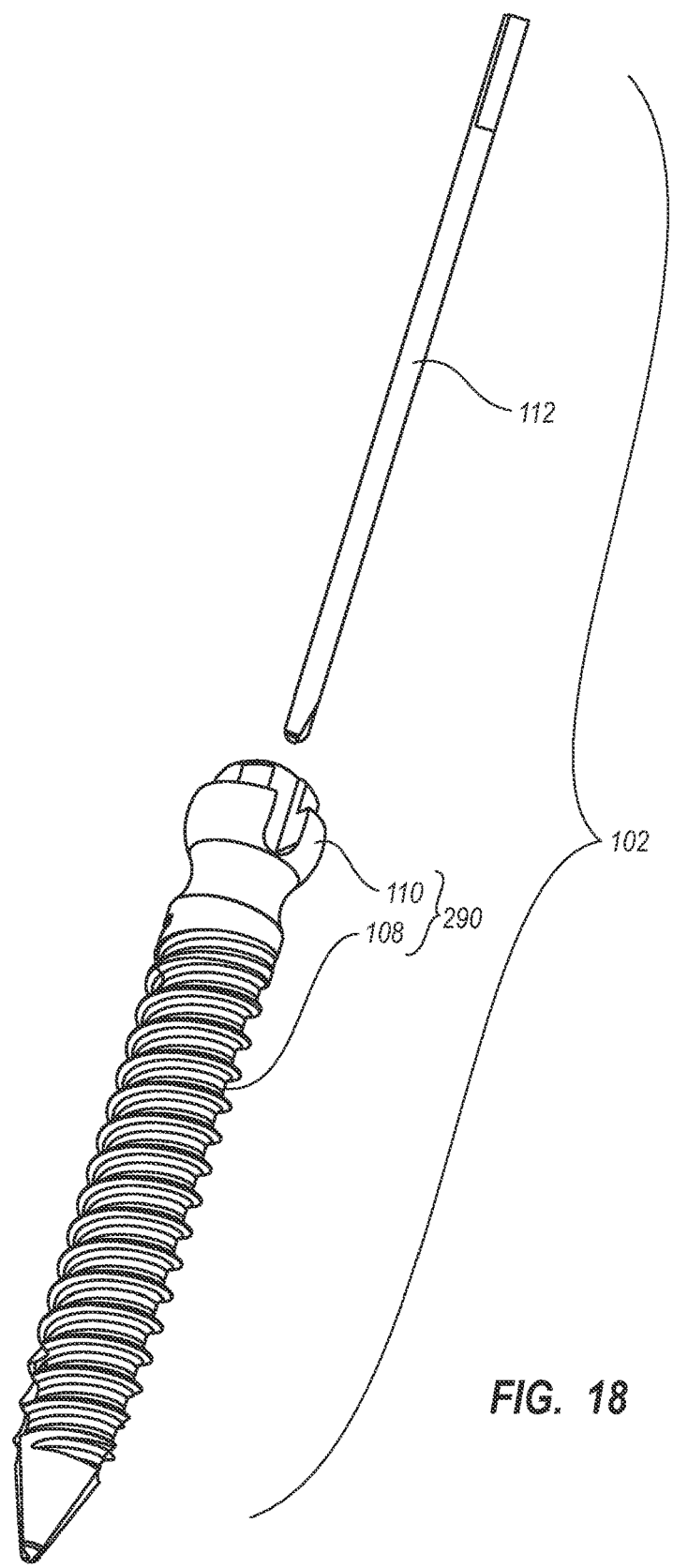
FIG. 18 is an exploded perspective view of an alternative embodiment of the screw portion shown in FIG. 17 wherein the head and the shaft of the screw portion are integrally formed as a unitary member.

In an alternative method of manufacturing screw portion 102, after core 112 has been formed, blank 292 is configured so that both head portion 204 and shaft portion 206 can be formed therefrom. Specifically, depicted in FIG. 18, screw portion 102 is shown as being comprised of a body 290 and core 112 that is positioned therein. Body 290 comprises shaft 108 and head 110. However, in contrast to the prior embodiment where head 110 is attached to shaft 108, in this embodiment shaft 108 and head 110 are integrally formed as a single, unitary structure. That is, both shaft 108 and head 110 are milled, cut or otherwise formed from a single blank that is formed about core 112. As such, in this embodiment the entire body 290 is comprised of a radiolucent material, such as those previously discussed with regard to shaft 108, while core 112 is typically comprised of a radiopaque material but can also be comprised of a radiolucent material or combination. As with other embodiments, the positioning markers 147 (FIGS. 10 and 11) can also be used with body 290.

In one similar method of manufacture, body 290 can initially be formed by winding a radiolucent fiber/adhesive matrix about a removable core as discussed above. The removable core can then be slid out of body 290. The remaining passageway can then be backfilled by injecting a radiolucent material such as an epoxy or other adhesive within the passageway. Alternatively, a radiolucent or radiopaque core can be slid into the passageway and secured in place by an adhesive, welding or other method of securing. As a result, the entire body and core can be radiolucent. Again, to help facilitate placement, positioning marks 147 (FIGS. 10 and 11) can be used with the radiolucent body.

Once screw portion 102 has been manufactured and assembled as described above, the polyaxial bone screw 100 can be assembled with screw portion 102 as one of its components. For example, turning to FIG. 13, to assemble polyaxial bone screw 100, shaft 108 of assembled screw portion 102 is passed down through longitudinal passage 232 and opening 249 of collar 104. Head 110 of screw portion 102, however, has a maximum diameter that is greater than the minimum diameter of opening 249 extending through seat 250 of collar 104. As such, head 110 of screw portion 102 rests on seat 250 of collar 104 and is prevented from passing through opening 249. As a result of the rounded configuration of bottom portion 150 of head 110 and the tapered sloping of seat 150, head 110 can freely slide on seat 250 such that screw portion 102 and collar 104 can freely pivot relative to each other.

Once screw portion 102 is seated within collar 104, pin 254 is advanced into pin hole 252. First end 256 of pin 254 is secured within pin hole 252 such as by welding, adhesive, press fit, or other mechanical engagement, such as threaded engagement. In this position, second end 258 of pin 254 projects into engagement slot 164 of screw portion 102. It is noted that pin 254 is spaced apart above floor 170 of engagement slot 164. As a result, screw portion 102 and collar 104 can continue to freely pivot relative to each other. However, because pin 254 extends over floor 170, head 110 is prevented from passing back up through collar 104. Pin 254 also functions to couple screw portion 102 and collar 104 together so that rotation of collar 104 or screw portion 102 also facilitates rotation of the other of the collar 104 or screw portion 102. As such, screw portion 102 can be implanted or removed simply by rotating collar 104. In alternative embodiments, it is appreciated that pin 62 can come in a variety of different configurations and can be mounted at a variety of different orientations and locations. Pin 62 can also be comprised of a radiolucent or radiopaque material.

In an alternative embodiment, head 110 is mounted on the collar 104 using pin 254, as described above, before head 110 is attached and secured to core 112 and shaft 108.

Figure 19:
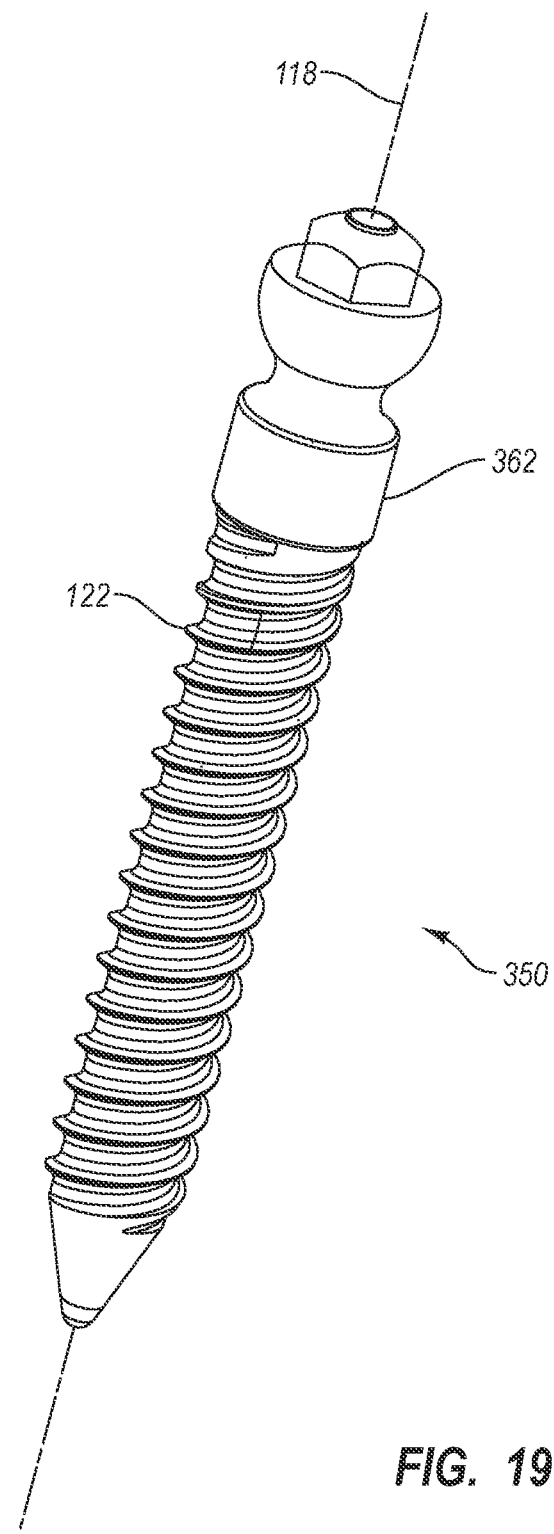
FIG. 19 is a perspective view of an alternative embodiment of an assembled screw portion of a bone screw according to the present invention.

Depicted in FIG. 19 is an alternative embodiment of a screw portion 350 incorporating features of the present invention that can be used with polyaxial bone screw 100. Like elements between screw portion 350 and other screw portions described herein are identified by like reference characters.

Figure 20:
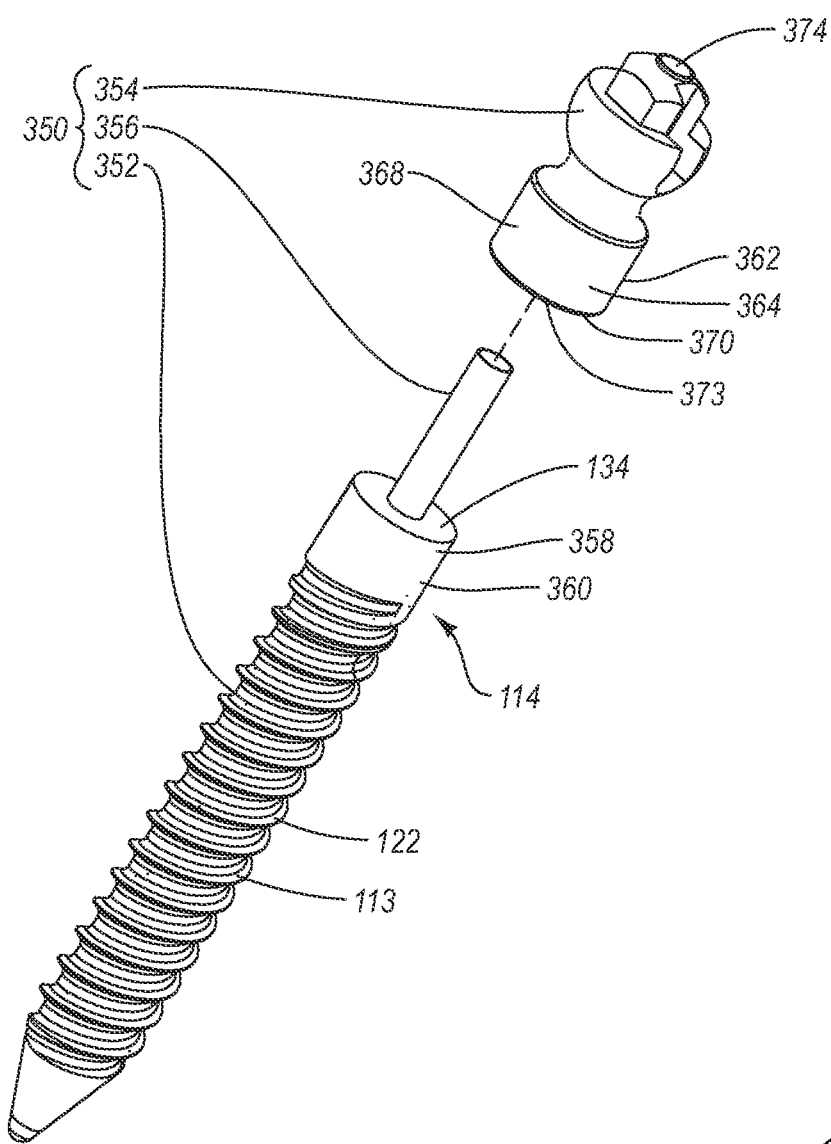
FIG. 20 is a perspective view of the screw portion shown in FIG. 19 in a partially assembled state.

As depicted in FIG. 20 and similar to screw portion 102, screw portion 350 comprises an elongated shaft 352 having a head 354 disposed thereon with a core 356 extending longitudinally through shaft 352 and head 354.

Screw portion 350 is similar to screw portion 102 except for the attachment structure between shaft 352 and head 354. For example, instead of attachment member 126 of shaft 108 having a flat 136 and projecting from an end face 132 of shaft body 113, attachment member 358 of shaft 352 is simply an extension of shaft body 113 having the same diameter as shaft body 113. That is, attachment member 358 projects from shaft body 113 in such a manner that no end face 132 is formed. In other words, attachment member 358 has an encircling exterior surface 360 that is aligned with exterior surface 122 of shaft body 113 at proximal end 114. Exterior surface 360 extends to terminal end face 134.

Figure 21:
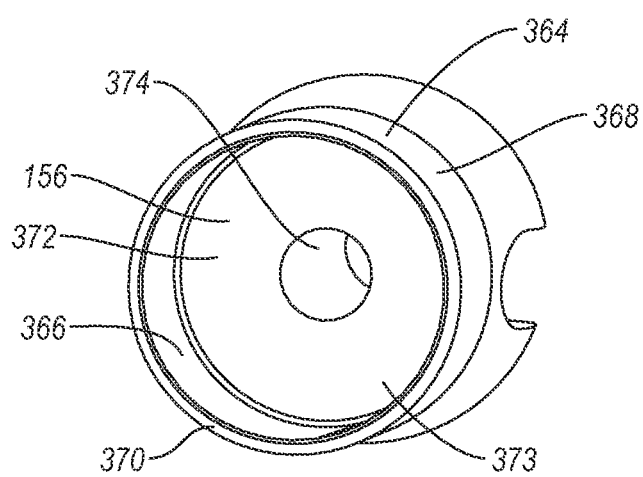
FIG. 21 is a bottom perspective view of the head of the screw portion shown in FIG. 20.

Correspondingly, head 354 is similar to head 110 except that head 354 further comprises a shoulder 362 extending from the outer perimeter of bottom surface 156. As shown in FIG. 21 in conjunction with FIG. 20, shoulder 362 comprises an encircling perimeter wall 364 having an inner surface 366 and an opposing outer surface 368 extending from bottom surface 156 to a terminal end face 370. Inner surface 366 of perimeter wall 364 bounds an attachment recess 372 that is sized and shaped so as to snugly fit over attachment member 358. As such, attachment recess 372 is substantially cylindrical in shape in the depicted embodiment, having a mouth 373 defined by terminal end face 370. Because of attachment recess 364, no attachment recess is necessary within bottom surface 156, although attachment recess 364 could also extend into bottom surface 156 if so desired.

Because of the size and shape of attachment member 358 and attachment recess 372, the amount of surface area that can be used for bonding the two together is increased over other embodiments. This can allow for a stronger bond that can withstand more torque.

Similar to head 110, head 354 also includes a second passageway 374. Second passageway 374 is similar to second passageway 182 except second passageway 374 has a substantially circular cross-sectional shape without a straight portion 184.

Core 356 is similar to core 112, except that head portion 204 remains substantially circular in cross section to match the shape of second passageway 364. However, any of the cores described herein or contemplated by the invention can be used with screw portion 350, and first and second passageways will reflect this. Furthermore, flats or other surface structures can be formed on attachment member 358 and inner surface 366 of head 354.

As with screw portion 102, shaft 352, head 354, and core 356 can respectively be comprised of the same materials as discussed above regarding shaft 108, head 110, and core 112. Also, screw portion 350 can be manufactured and assembled similar to that described above with regard to screw portion 102. One small difference from assembled screw portion 102 is that, as shown in FIG. 19, when screw portion 350 is assembled, shoulder 362 extends slightly further away from the longitudinal axis 118 then exterior surface 122 as extension 362 fits over attachment member 358.

Furthermore, it is appreciated that many of the alternative design features as previously discussed with regard to screw portion 102 are also applicable to screw portion 350. For example, to aid in the implantation of screw portion 350, positioning markers 147 (FIGS. 10 and 11), as previously discussed, can again be formed on or within shaft 352. Likewise, as with screw portion 102, by forming shaft 352 out of a radiolucent material while core 356 is formed from a radiopaque material, screw portion 350 can be properly positioned while limiting unwanted obstructions. Specifically, the thin core 356 can be easily viewed by X-ray to determine proper positioning of the screw portion 350 but the larger shaft 352 is radiolucent so as to not obstruct surrounding structure.

Figure 22:
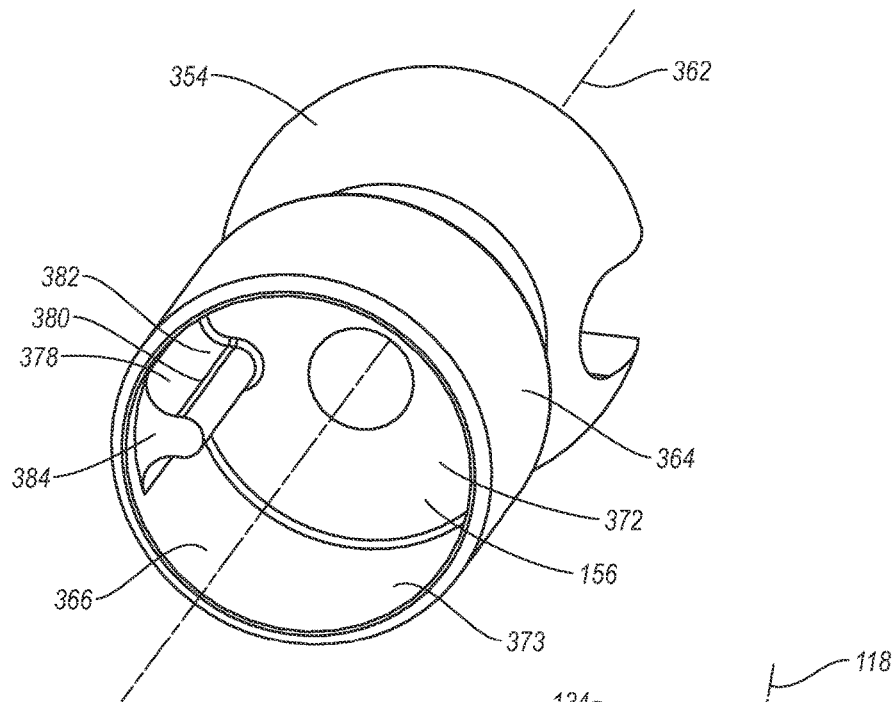
FIG. 22 is a bottom perspective view of an alternative embodiment of the head of the screw portion shown in FIG. 20.

To increase the bonding strength and ability to transfer torque, one or more keyed splines and corresponding grooves can be disposed within attachment recess 372 and attachment member 358. For example, FIG. 22 shows a spline 378 projecting into attachment recess 372 from the inner surface 366 of perimeter wall 364. Spline 378 comprises a sidewall 380 that extends longitudinally from a first end 382 disposed at or near bottom surface 156 to a spaced apart second end 384 disposed at or near the mouth 373 of the attachment recess 372.

Figure 23:
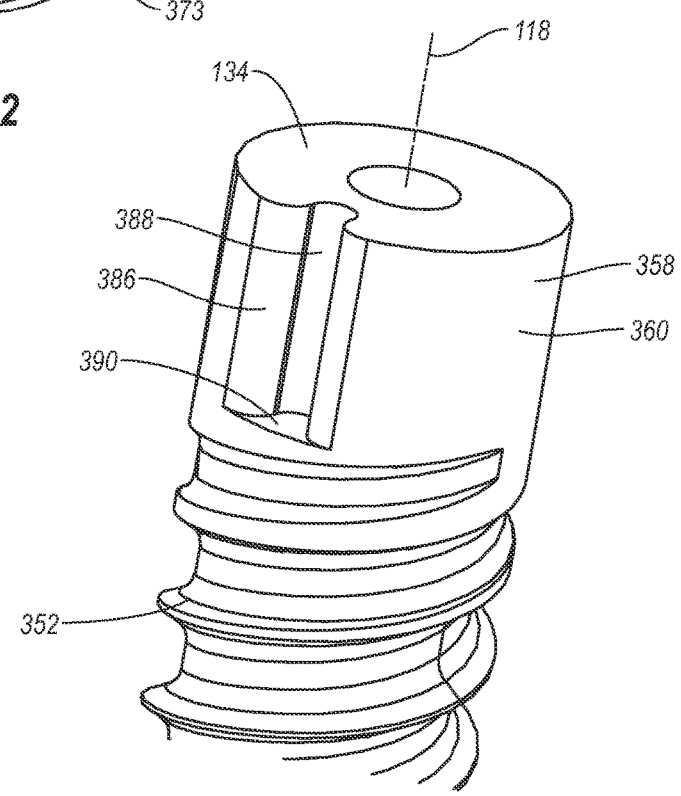
FIG. 23 is a partial top perspective view of an alternative embodiment of the shaft of the screw portion shown in FIG. 20.

Turning to FIG. 23, a corresponding groove 386 is formed in exterior surface 360 of attachment member 358. Groove 386 is bounded by a sidewall 388 that extends longitudinally from terminal end face 134 to a spaced apart end wall 390. Groove 386 is sized and shaped so as to snugly receive spline 380 when attachment member 358 is received within attachment recess 372. As shown in the depicted embodiment, spline 380 is substantially parallel to longitudinal axis 162 of head 354 and groove 386 is substantially parallel to longitudinal axis 118 of shaft 352 so as to be aligned when assembled. Other matching shapes can alternatively be used. For example, spline 380 and groove 386 can be helical in nature, if desired. In that case, head 354 would be screwed onto shaft 352 during assembly. Other mating shapes are also possible. For example, attachment member 358 can be formed with one more flats or can be formed into a polygonal, oval, irregular or other non-circular shape. Attachment recess 372 would have a complementary configuration.

Figure 24:
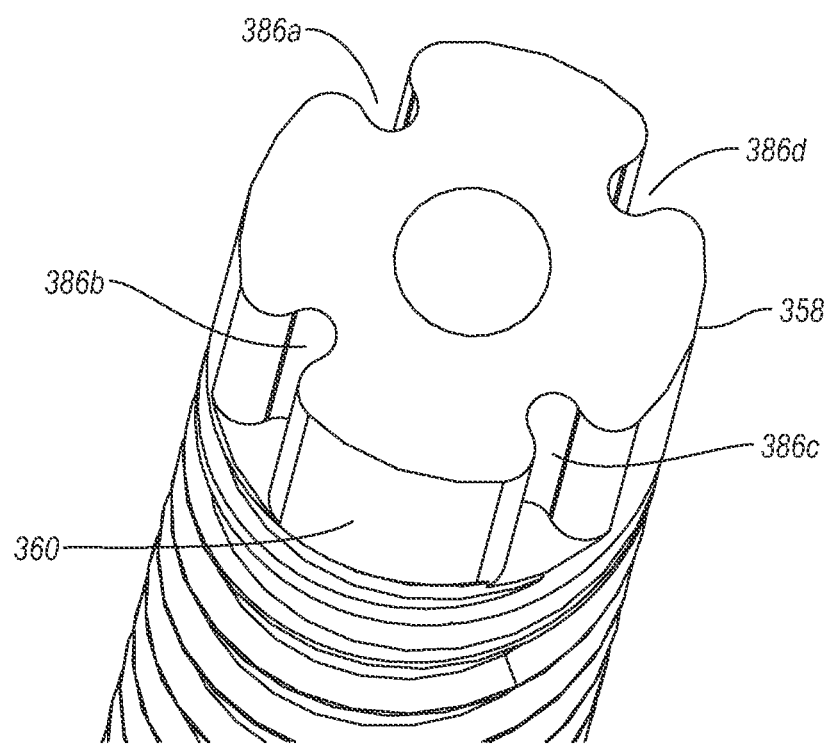
FIG. 24 is a top perspective view of a portion of another alternative embodiment of the shaft of the screw portion shown in FIG. 20.

It is appreciated that more than one spline and groove can be used in the present invention. For example, in FIG. 24, four grooves 386a-d are formed in exterior surface 360 of attachment member 358. Although not shown, it is appreciated that a head 354 incorporating four splines 378 that mate with grooves 386a-d would correspondingly be used. In the depicted embodiment, the grooves 386a-d are similar to each other and equidistant from each other, although this is not necessary. Grooves 386 and splines 378 can alternatively be spaced with respect to each other so as to form a sort of key. In this manner heads 354 will only attach to certain shafts 352 in a particular orientation depending on the keyed fit. Alternatively, one or more of the grooves 386 can be shaped differently than the other grooves so as to also form a key. Of course, head 354 will incorporate splines 378 that match the keyed grooves 386, so as to attach to shaft 352 in the particular orientation.

It is appreciated that more or less splines and grooves can be used with the present invention. For example, screw portion 350 can comprise two or three or more splines and grooves.

Figure 25:
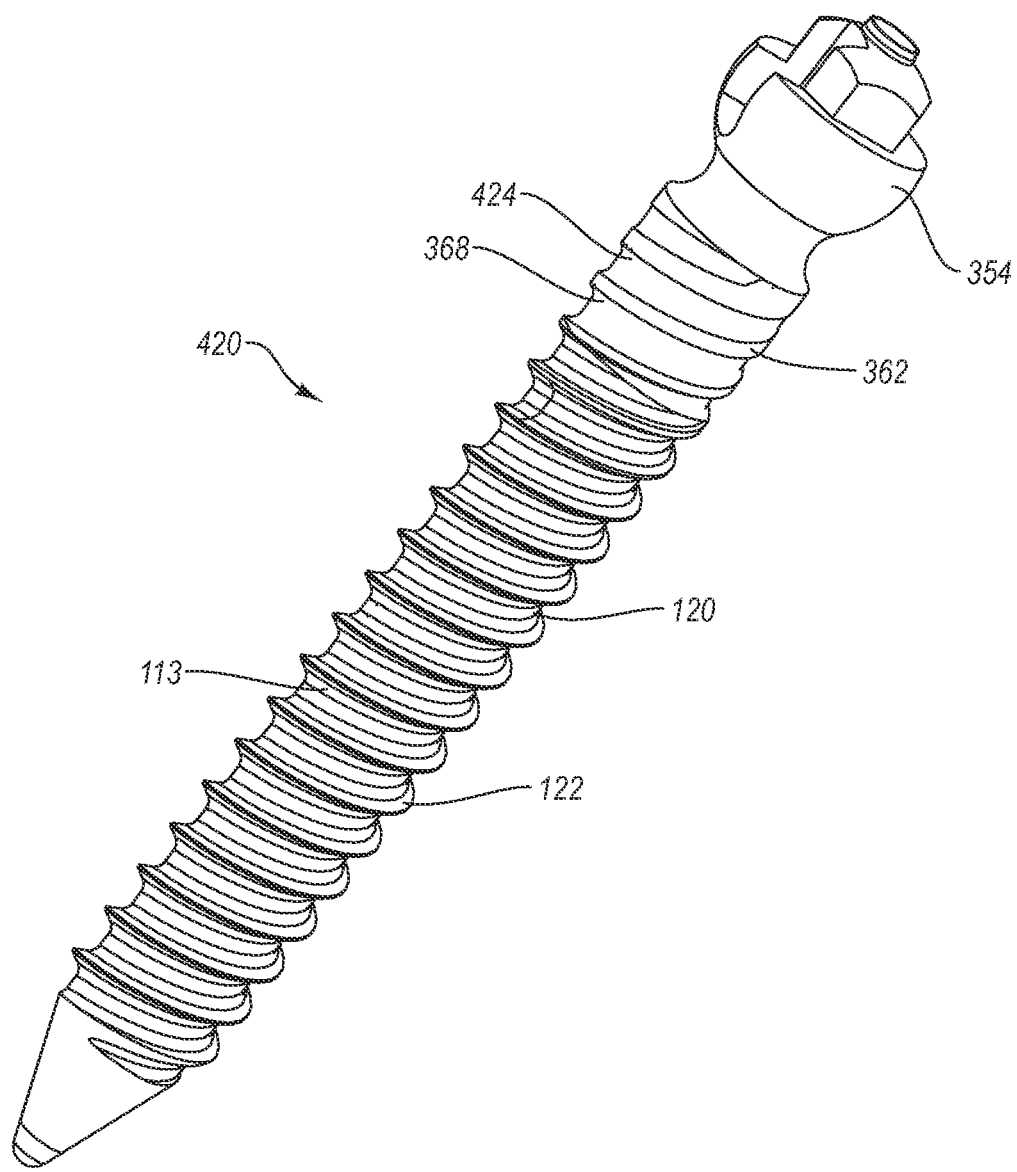
FIG. 25 is a perspective view of an alternative embodiment of an assembled screw portion of a bone screw according to the present invention.

Depicted in FIG. 25 is another alternative embodiment of a screw portion 420 incorporating features of the present invention that can be used with polyaxial bone screw 100. Like elements between screw portion 420 and other screw portions described herein are identified by like reference characters.

Screw portion 420 is similar to screw portion 350 (FIG. 20) except that the shoulder 362 of head 354 includes an extension of the threads 120 that are formed on the exterior surface 122 of shaft body 113.

Figure 26:
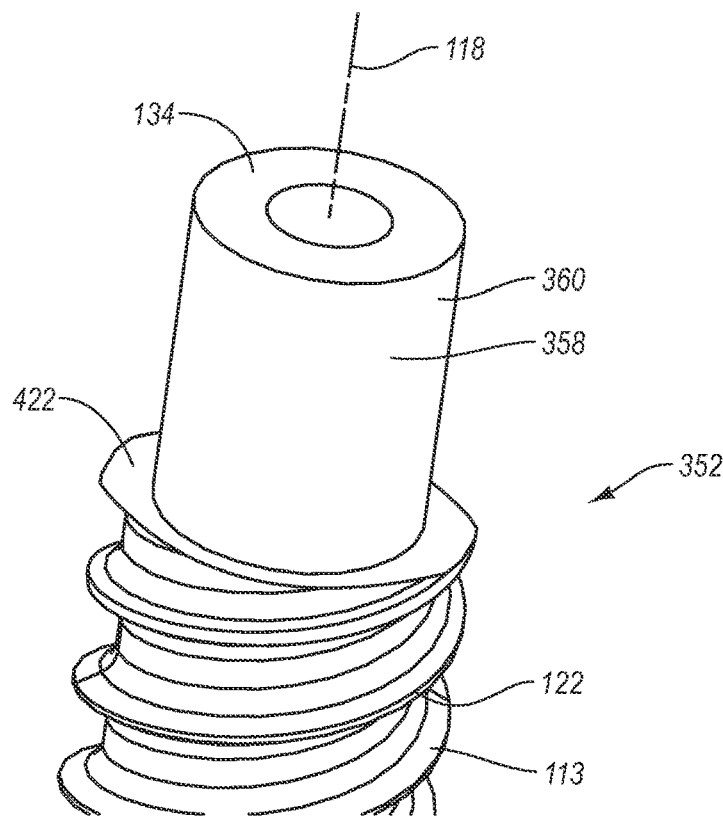
FIG. 26 is a perspective view of a portion of the screw portion shown in FIG. 25.

As shown in FIG. 26, attachment member 358 of shaft 352 is sized so as to have a smaller diameter than the exterior surface 122 of shaft body 113. As a result, similar to end face 132, an end face 422 is formed on shaft body 113 between the exterior surface 360 of attachment member 358 and exterior surface 122 of shaft body 113. End face 422 is generally planar and orthogonal to longitudinal axis 118 of shaft 352, but this is not required. Attachment member 358 centrally projects from this end face 422 to terminal end face 134. Because of the smaller diameter of attachment member 358, shoulder 362 can correspondingly have a smaller diameter. Again, if desired one or more flats, grooves, splines, threads, or other structures can be formed on attachment member 358 with a complementary structure being formed on head 354.

Figure 27:
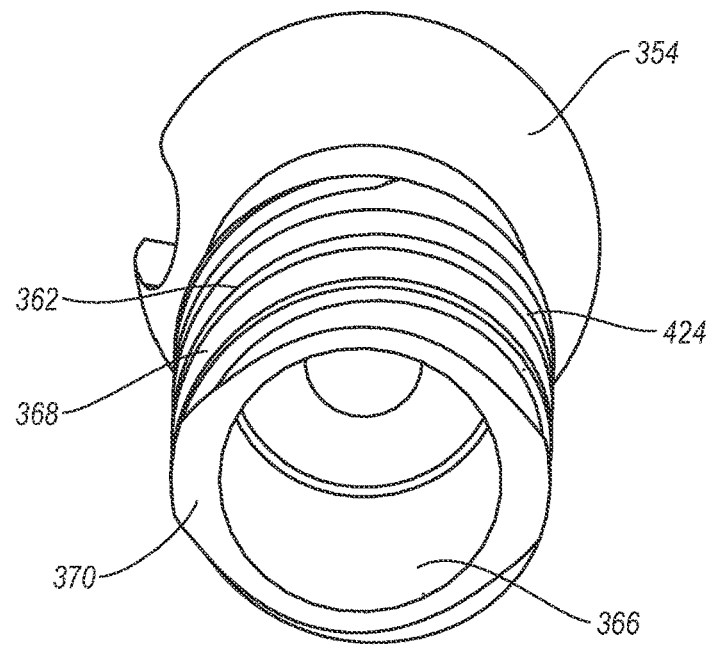
FIG. 27 is a bottom perspective view of the head of the screw portion shown in FIG. 25.

As shown in FIG. 27, the end face 370 of shoulder 362 of head 354 is shaped so as to match the shape of end face 422 and inner surface 366 is dimensioned with a smaller diameter so as to snugly receive the smaller diameter attachment member 358. Due to the smaller dimensions, when assembled the outer surface 368 of shoulder 362 and the exterior surface 122 of shaft body 113 are aligned, as shown in FIG. 25. Also as shown in FIG. 25, one or more threads 424 helically encircle and radially outwardly project from outer surface 368 of shoulder 362. The threads 424 are configured to align with the threads 120 of shaft body 113 so that as the screw portion 420 is threaded into the bone, the threads 424 will also engage the bone.

Because the threads extend onto the shoulder 362, the shaft body 113 can be shorter so that the attachment member 358 and the shoulder 362 can be longer than in screw portion 350, thereby providing even more surface area for bonding between the head 354 and shaft 352. This results in a stronger bond. Furthermore, the threads 424 on the shoulder 362 cause a better bone-to-screw connection when threads 424 are threaded into cortical bone.

Figure 28:
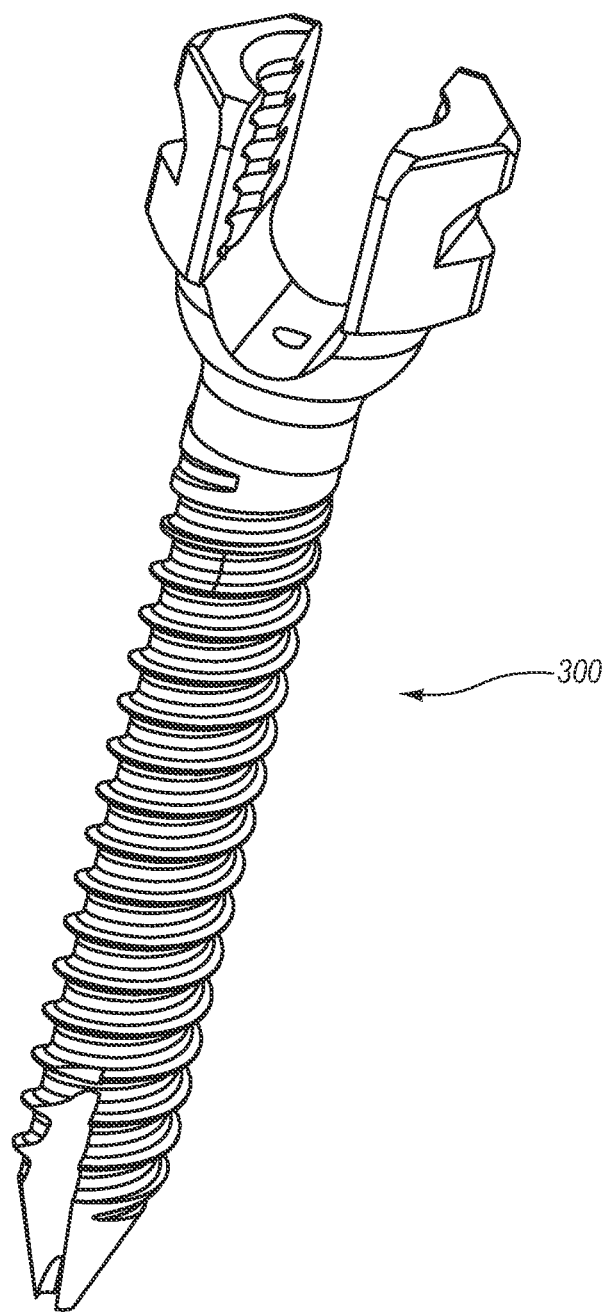
FIG. 28 is one embodiment of a fixed bone screw wherein a collar is rigidly secured to the end of the shaft.

Depicted in FIG. 28 is one embodiment of a fixed bone screw 300 incorporating features of the present invention. In general, fixed bone screw 300 comprises a collar rigidly secured to or formed on the end of a threaded shaft so that the collar cannot pivot relative to the shaft. Like elements between bone screw 300 and the prior discussed embodiments are identified by like reference characters.

Figure 29:
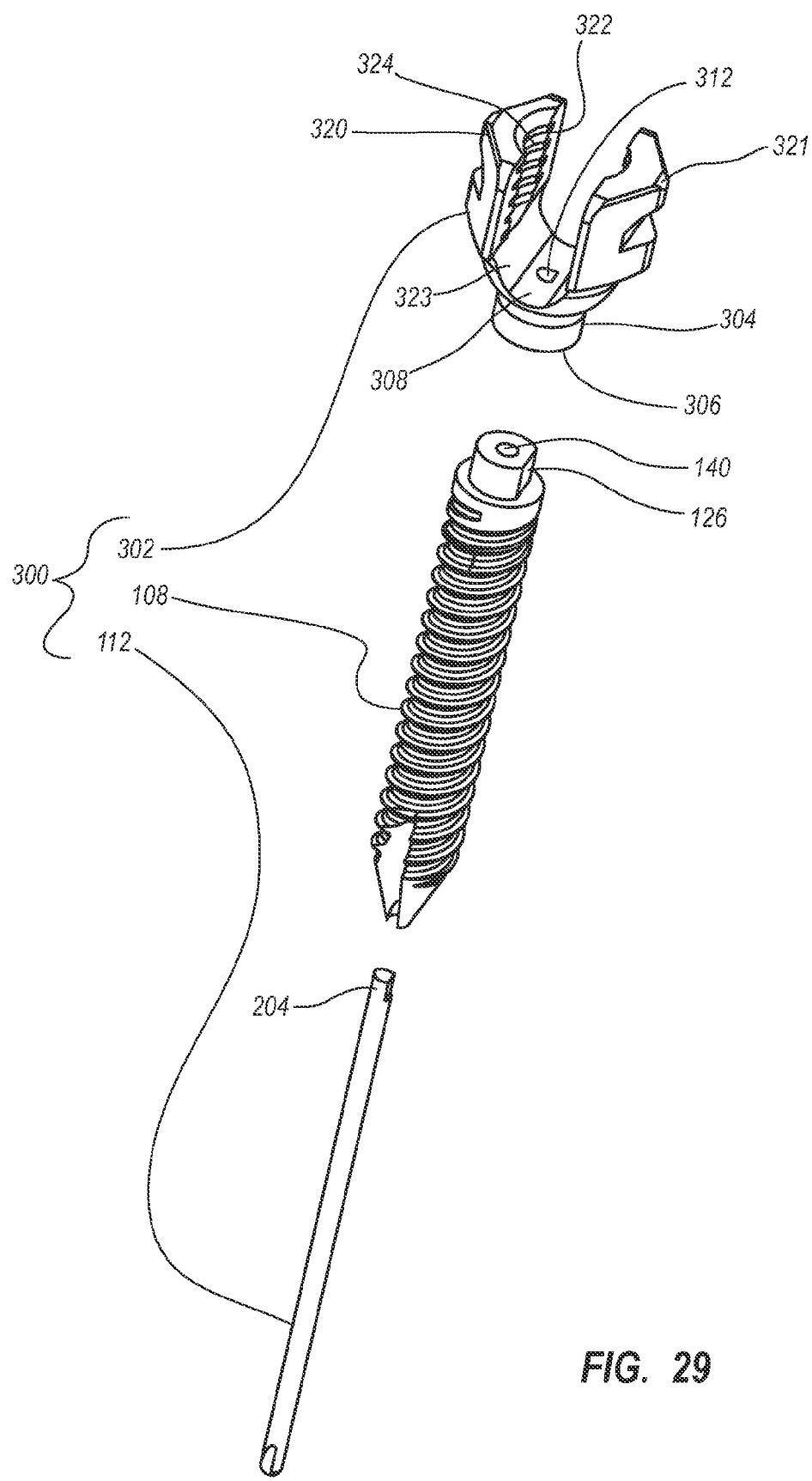
FIG. 29 is an exploded view of the bone screw shown in FIG. 28.

As depicted in FIG. 29, in one embodiment bone screw 300 comprises shaft 108, core 112, and a collar 302. Core 112 is secured within first passageway 140 of shaft 108. The previously discussed materials, configurations, methods of manufacture and alternatives thereof of shaft 109 and core 112 are also applicable to bone screw 300.

Figure 30:
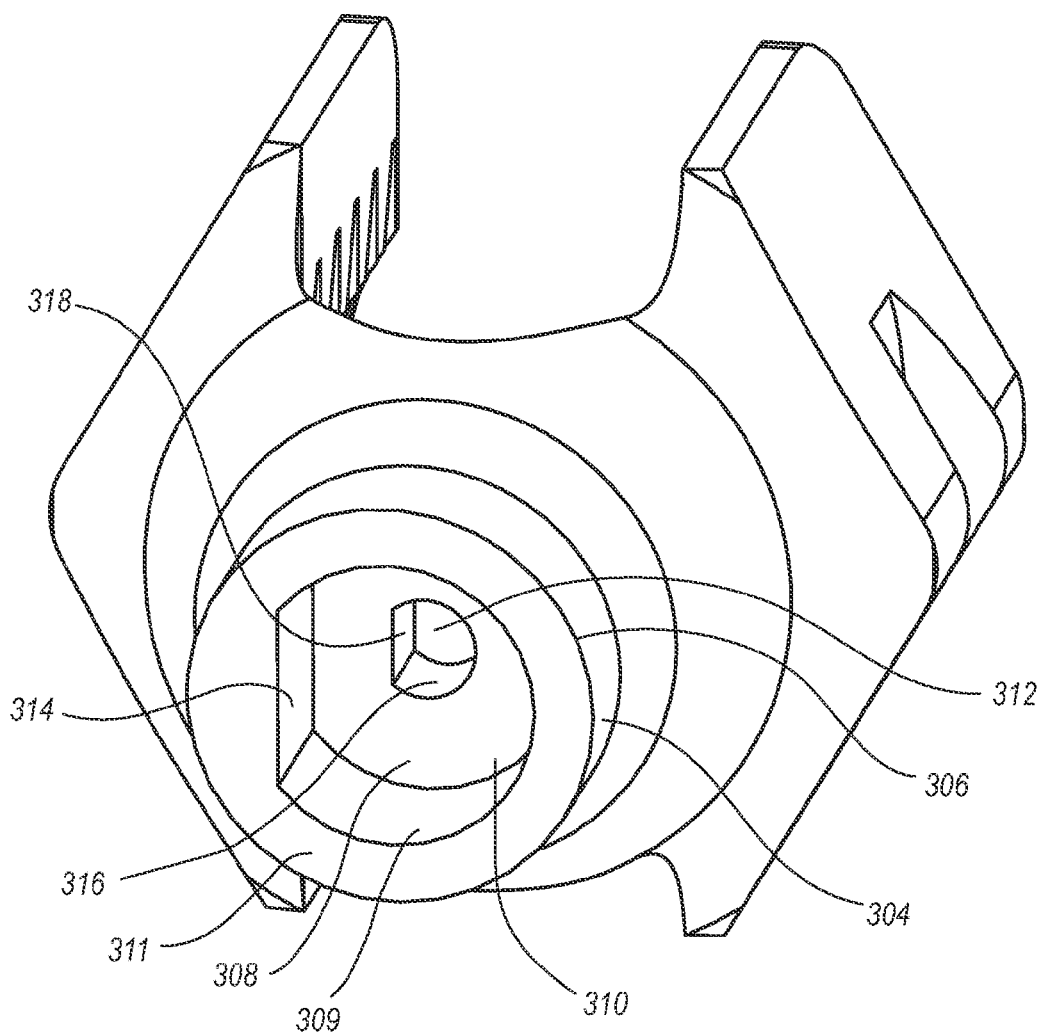
FIG. 30 is a perspective bottom view of the collar shown in FIG. 29.

As depicted in FIGS. 29 and 30, collar 302 comprises a base 304 that extends from a first end 306 to a floor 308. Base 304 has an interior surface 309 that bounds an attachment recess 310 extending from floor 308 to a first end face 311 at first end 306. Attachment recess 310 thus has the configuration of a blind socket. Interior surface 309 has a substantially circular transverse cross section with a flat 314 formed thereon. Attachment recess 310 has a configuration complementarily to and is configured to receive and secure to attachment member 126 of shaft 108 in the same manner that attachment member 126 is received and secured within attachment recess 128 of head 110 (FIG. 6).

Floor 308 also has an interior surface 316 that bounds a second passageway 312 that extends through floor 308 so as to communicate with attachment recess 310. Interior surface 316 also has a substantially circular transverse cross section with a flat 318 formed thereon.

Second passageway 312 is positioned so that when attachment member 126 is secured within attachment recess 310, first passageway 140 of shaft 108 is aligned with second passageway 312. It is also appreciated that second passageway 312 is also configured to receive and secure to head portion 204 of core 112 in the same manner that head portion 204 is received and secured within second passageway 182 of head 110 (FIG. 6).

A pair of spaced apart arms 320 and 321 project from opposing sides of base 304 in substantially parallel alignment. Each arm 320 and 321 has an interior surface 322. The opposing interior surfaces bound a substantially U-shaped channel 323 in which stabilizing rod 107 (FIG. 1) can be received. Furthermore, each interior surface 322 has a thread portion 324 formed thereon. Thread portions 324 enable locking screw 270 (FIG. 1) or an alternative embodiment thereof to threadedly engage with arms 320 and 321 so as to secure stabilizing rod 107 within channel 323. It is appreciated that many of the alternative design features as previously discussed with regard to collar 104 are also applicable to collar 302. Likewise, collar 302 can be comprised of the same materials as previously discussed with regard to collar 104.

To aid in the implantation of bone screw 300, positioning markers 147 (FIGS. 10 and 11), as previously discussed, can again be formed on or within shaft 108. Likewise, as with screw portion 102, by forming shaft 108 out of a radiolucent material while core 112 and collar 302 are formed from a radiopaque material, bone screw 300 can be properly positioned while limiting unwanted obstructions. Specifically, the thin core 112 can be easily viewed by X-ray to determine proper positioning of the bone screw but the larger shaft 108 is radiolucent so as to not obstruct surrounding structure.

Figure 31:
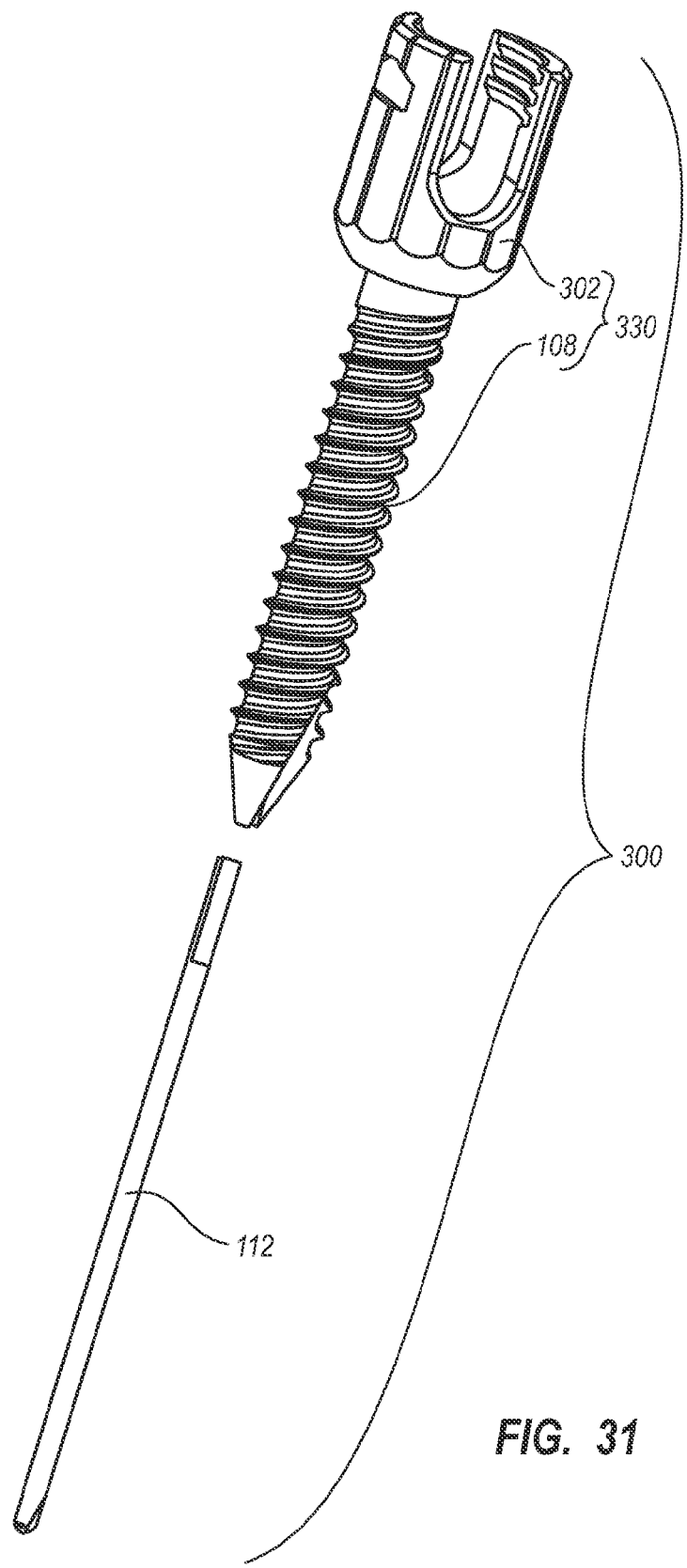
FIG. 31 is an exploded perspective view of an alternative embodiment of the fixed bone screw shown in FIG. 28 wherein the collar and the shaft of the bone screw are integrally formed as a unitary member.

Depicted in FIG. 31 is an alternative embodiment of bone screw 300 incorporating features of the present invention wherein like element are identified by like reference characters. In this embodiment, bone screw 300 is shown as being comprised of a body 330 and core 112 that is positioned therein. Body 330 comprises shaft 108 and collar 302. However, in contrast to the prior embodiment where collar 302 is secured to shaft 108, in this embodiment shaft 108 and collar 302 are integrally formed as a single unitary structure. That is, both shaft 108 and collar 302 are milled, cut or otherwise formed from a single blank that is formed about core 112. As such, in this embodiment the entire body 330 is comprised of a radiolucent material, such as those previously discussed with regard to shaft 108, while core 112 is typically comprised of a radiopaque material but can also be comprised of a radiolucent material. As with other embodiments, one or more positioning markers 147 (FIGS. 10 and 11) can also be used with body 330. Furthermore, as discussed in prior embodiments, core 112 can be removed and replaced with an adhesive or an alternative core.

Figure 32:
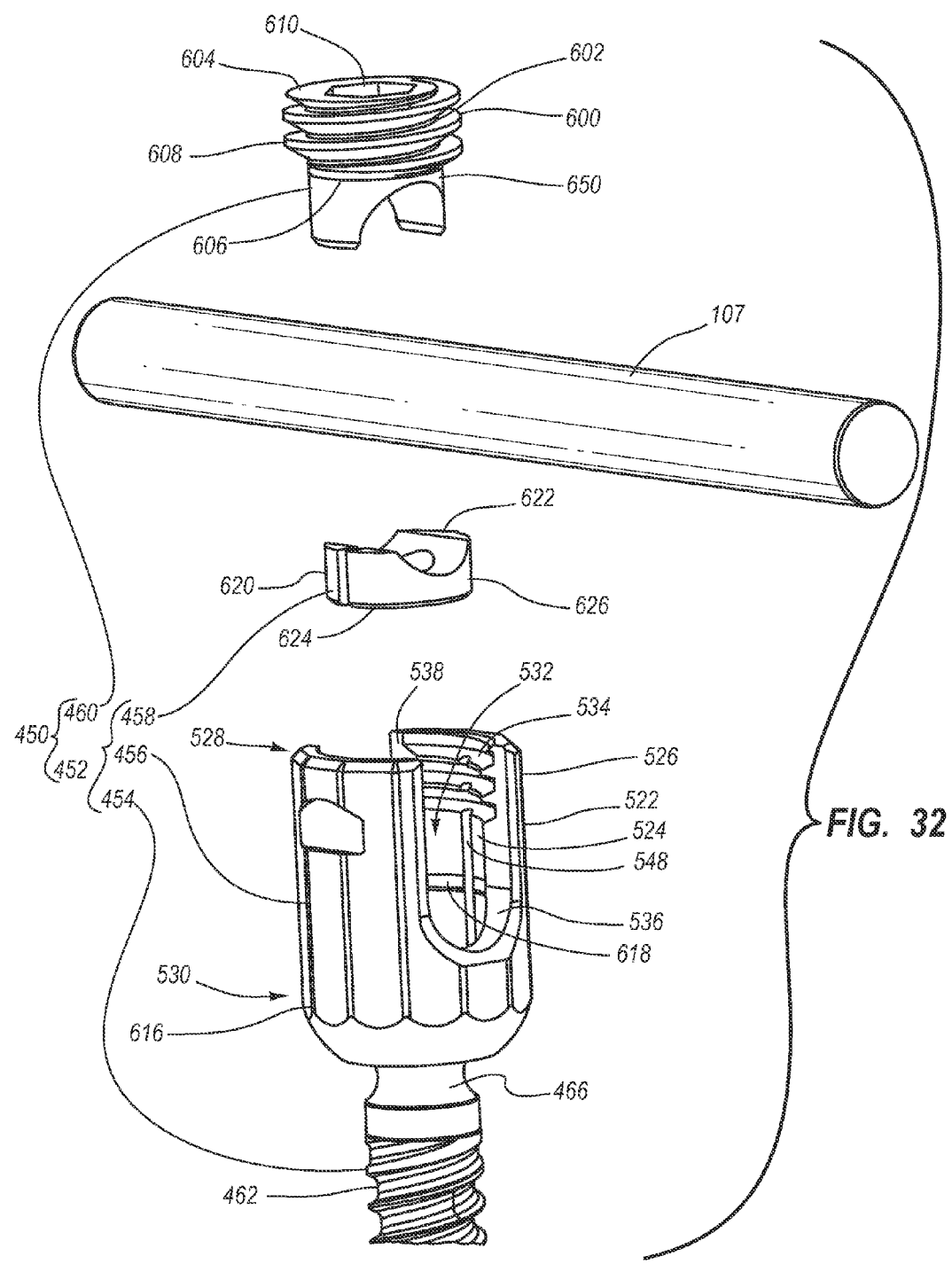
FIG. 32 is a exploded perspective view of an alternative embodiment of a spinal stabilizing system.

Depicted in FIG. 32 is another alternative embodiment of a spinal stabilizing system 450 wherein like elements are identified by like reference characters. Stabilizing system 450 includes a polyaxial bone screw 452 comprising an elongated screw portion 454, a collar 456 pivotally mounted thereon and a saddle 458 that is disposed within collar 456. Stabilizing system 450 also includes a fastener 460 that is selectively engageable with collar 456 to secure polyaxial bone screw 452 to stabilizing rod 107.

Figure 33:
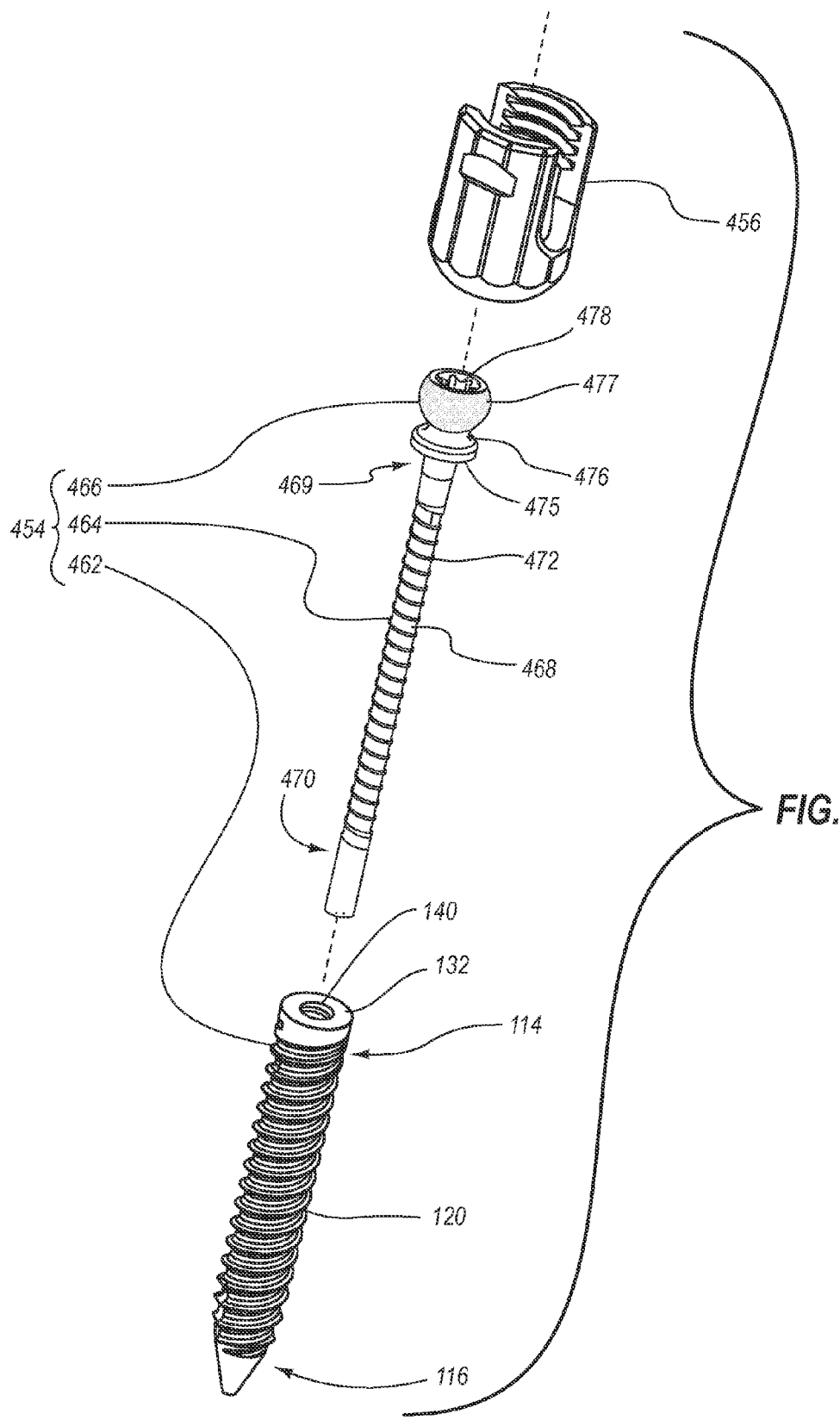
FIG. 33 is an exploded perspective view of the screw portion of the spinal stabilizing system shown in FIG. 32.

As depicted in FIG. 33, screw portion 454 of bone screw 452 comprises a shaft 462, an elongated core 464 that extends within shaft 462, and a head 466 formed on an end of core 464. Shaft 462 is substantially identical to shaft body 113 discussed with regard to FIGS. 3 and 4 and thus like reference characters reference like elements. Shaft 462 can be made from the same radiolucent materials and with the same methods and alternatives as discussed with regard to shaft body 113. Furthermore, the various markers as discussed herein can be used in association with shaft 462.

In contrast to the embodiment shown in FIG. 2 wherein head 110 and core 112 are formed as separate discrete elements, in the present embodiment head 466 and core are integrally formed as a single, unitary structure. In other embodiments, head 466 and core 464 can be rigidly fixed together such as by welding, press fit, or other connection techniques. Core 464 has an exterior surface 468 extending between a proximal end 469 and an opposing distal end 470. Core 464 is secured within passageway 140 of shaft 462 using the methods previously discussed. In this embodiment, however, a helical thread 472 is formed on exterior surface 468 and extends along a length of core 464. Helical thread 472 has a thread orientation opposite that of thread 120 on shaft 462. As a result, core 464 further engages shaft 462 when bone screw 452 is being backed out of a bone, thereby helping to prevent separation between core 464 and shaft 462. In alternative embodiments, core 464 can have the other shapes and/or protrusions as discussed with regard to the other cores herein.

Figure 34:
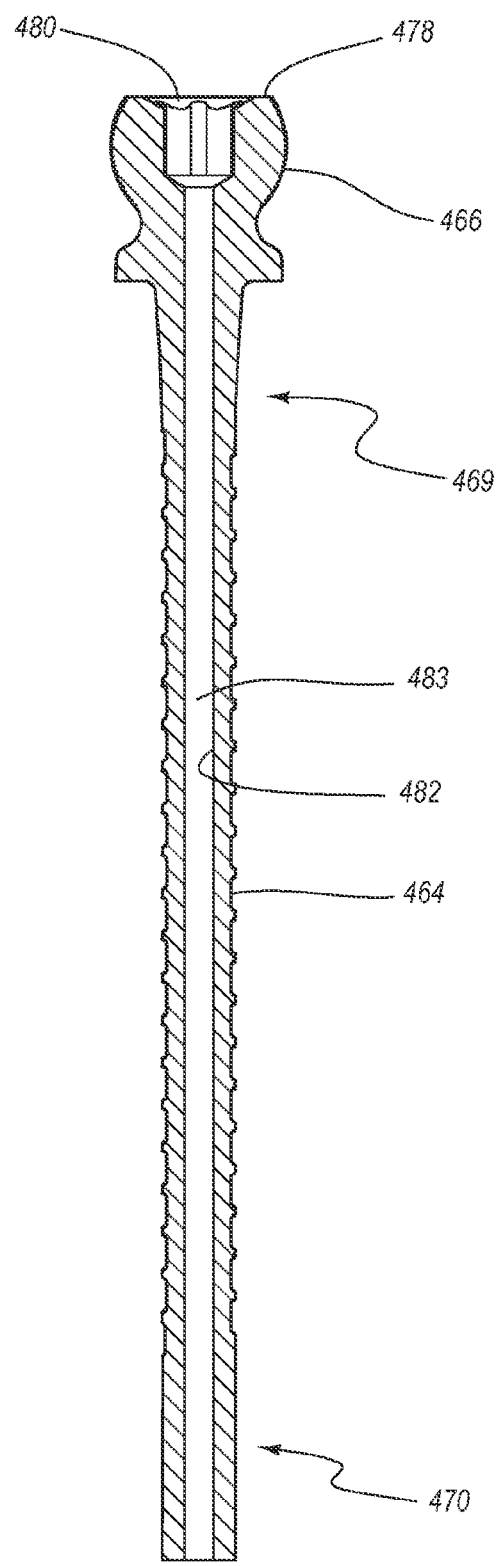
FIG. 34 is a cross sectional side view of the core and integral head of the screw portion shown in FIG. 33.

Head 466 comprises an annular shoulder 474 that extends between a flat bottom end face 475 and a recessed annular neck 476. Core 464 extends from bottom end face 475. Upwardly and outwardly extending from neck 476 is an annular, rounded head portion 477 that terminates a flat top face 478. If desired, texture, such as micro grooves or other patterns can be formed on the exterior surface of head portion 477 to facilitate locking between head 466 and collar 456 as discussed below in greater detail. As depicted in FIG. 34, an engagement socket 480 is recessed on top face 478. Engagement socket 480 is bounded by an encircling sidewall and typically has a polygonal or other non-circular transverse cross section so that a driver can engage with socket 480 for rotating bone screw 452. As also shown in FIG. 34, core 464 and head 466 each have an interior surface 482 that bounds a cannula 483 extending from engagement socket 480 through distal end 470 of core 464. Again, cannula 483 can be used to receive a guide wire for implanting bone screw 452 and/or can be used for other surgical techniques. In other embodiments, cannula 483 can be eliminated. Head 466 and core 464 can be made from the same radiopaque materials, such as radiopaque metals, as discussed with regard to the other heads and cores disclosed herein. During manufacture, shaft 462 is formed on or otherwise secured to core 464 so that shaft 462 is disposed against bottom face 475 of head 466.

Returning to FIG. 32, collar 456 comprises a tubular side wall 522 having an interior surface 524 and an exterior surface 526 that each extend between a first end 528 and an opposing second end 530. Interior surface 524 bounds a longitudinal passage 532 that longitudinally extends through collar 456. Internal threads 534 are formed on interior surface 524 at or toward first end 528.

Side wall 522 is formed having a pair of channels 536 and 538 that are disposed on opposing sides of side wall 522 and that transversely extend through side wall 522. In the embodiment depicted, channels 536 and 538 each have a substantially U-shaped configuration. Other channel shapes can also be used. Channels 536 and 538 form a portion of a transverse passage that transversely extends through collar 456 so as to intersect with the longitudinal passage 532 that also extends through collar 456. Each channel 536 and 538 is configured so that stabilizing rod 107 can be received therein as stabilizing rod 107 is placed within the transverse passage.

Figure 37:
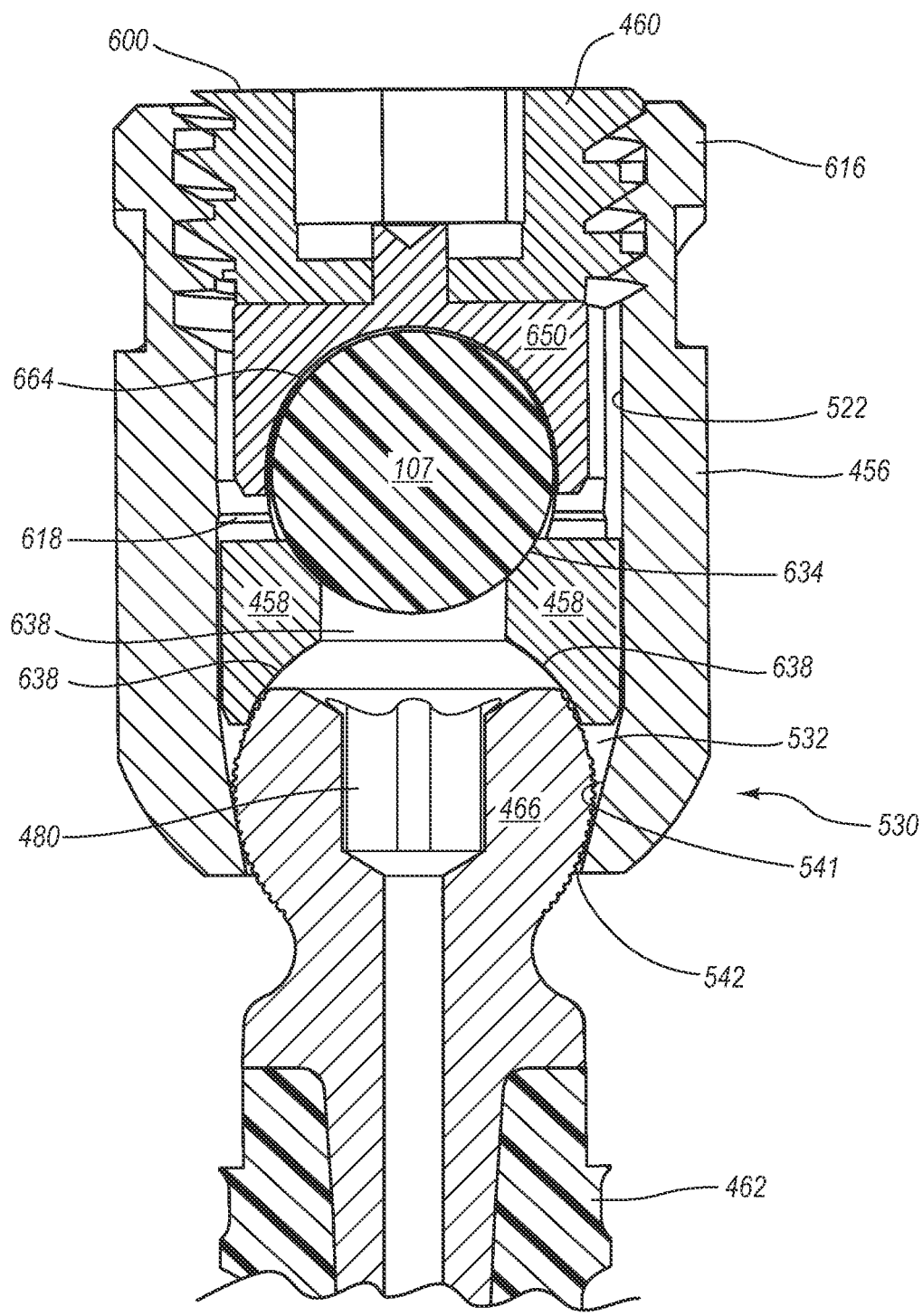
FIG. 37 is a cross sectional side view of the assembled spinal stabilizing system shown in FIG. 32.

As depicted in FIG. 37, collar 456 further comprises a shoulder 541 that radially inwardly projects from second end 530 of side wall 522 so as to encircle longitudinal passage 532. Shoulder 541 has a tapered interior surface that forms an annular seat 542. In alternative embodiments, seat 542 need not completely encircle passage 532. Seat 542 can also comprise two or more spaced apart portions.

During assembly of bone screw 452, shaft 462 is passed down through longitudinal passage 532 of collar 456. Head 466, however, has a maximum diameter that is greater than the minimum diameter of longitudinal passage 132 extending through seat 542 of collar 456. As such, head 466 rests on seat 542 of collar 456 and is prevented from passing through collar 456 as shown in FIG. 37. As a result of the spherical configuration of head 466 and the tapered sloping of seat 542, head 466 can freely slide on seat 542 such that shaft 462 and collar 456 can freely pivot relative to each other.

As shown in FIG. 32, fastener 460 can be used to secure stabilizing rod 107 to bone screw 452. Fastener 460 comprises a locking screw 600 having an encircling side wall 602 that extends between a top end face 604 and an opposing bottom end face 606. Radially outwardly projecting from side wall 602 of locking screw 600 so as to encircle locking screw 600 are one or more helical threads 608. Threads 608 of locking screw 600 are configured to threadedly engage with internal threads 534 of collar 456. A socket 610 or other type of engaging member or recess adapted to receive a driver can be disposed on top surface 604 of locking screw 600.

Fastener 460 is threaded into threads 534 formed on interior surface 524 of collar 456 to secure stabilizing rod 107 to bone screw 452 within channels 536 and 538 of collar 456. That is, once stabilizing rod 107 is disposed within the transverse passage of collar 456, locking screw 600 is screwed into collar 456 so that bottom end face 606 of locking screw 200 presses against stabilizing rod 107, which in turn causes stabilizing rod 107 to press against head 466. As a result, head 466 is pressed within seat 542 of collar 456 which locks screw portion 454 relative to collar 456.

Although not required, saddle 458 can be used to provide a seat for stabilizing rod 107 so as to reduce localized stress points. More specifically, without saddle 458, stabilizing rod 107 sits directly over engagement socket 480 on head 466 (FIG. 34). The perimeter edge of engagement socket 480 produces localized stress points on stabilizing rod 107 which can damage stabilizing rod 107 and/or distort engagement socket 480. Saddle 458 separates stabilizing rod 107 from the perimeter edge of engagement socket 480 and more uniformly distributes the clamping forces around stabilizing rod 107. For example, as depicted in FIG. 37, saddle 458 can be positioned between head 466 and stabilizing rod 107 such that when fastener 460 is threaded into collar 456, stabilizing rod 107 presses against saddle 458, which in turn presses against head 466. Again, as a result, head 466 is pressed within seat 542 of collar 456 which locks screw portion 454 relative to collar 456.

To be able to retain saddle 458 within passage 532 in a particular positioning arrangement, collar 456 can also include one or more channels or lips. For example, the embodiment depicted in FIG. 32 includes collar 456 having a channel 548 formed on interior surface 524. Channel 548 is generally aligned with longitudinal passage 532 and is designed to receive a key formed on saddle 458, as discussed in more detail below. Furthermore, collar 456 can also includes an inwardly projecting annular lip 618 formed on interior surface 524 that at least partially encircles longitudinal passage 532. Lip 618 is sized so as to have a slightly smaller diameter than the general diameter of interior surface 524.

Figure 35A:
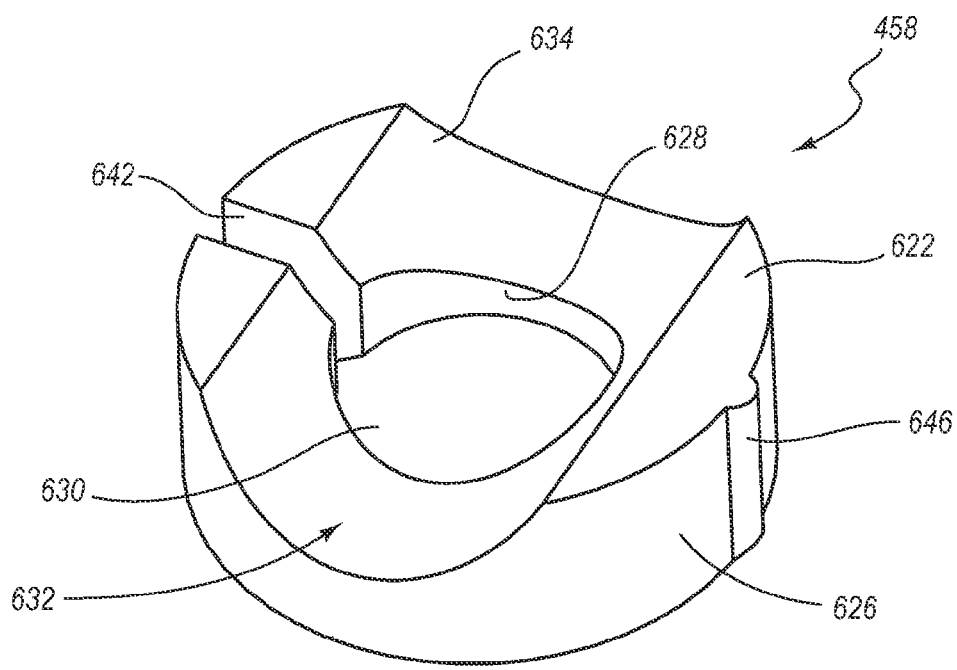
FIG. 35A is a top perspective view of the saddle shown in FIG. 32.
Figure 35B:
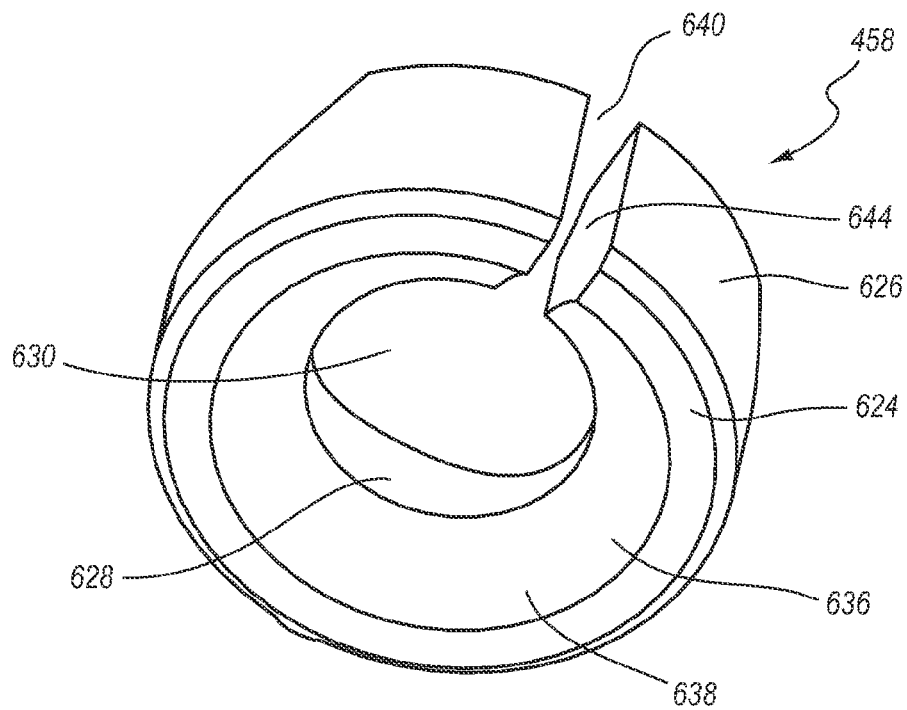
FIG. 35B is a bottom perspective view of the saddle shown in FIG. 35A.

Turning to FIGS. 35A and 35B, saddle 458 has a top surface 622 and an opposing bottom surface 624 with an encircling outer side wall 626 extending therebetween. An internal side wall 628 also extends between top and bottom surfaces 622 and 624 so as to bound a central opening 630 that extends all the way through saddle 458. Opening 630 is generally circular and is sized so as to allow a driver tool to access the socket 480 on the head 466 (FIG. 37) when saddle 458 is disposed against head 466. The opening 630 causes saddle 458 to be generally ring shaped when viewed from a direction generally normal to the top and bottom surfaces 622 and 624.

A substantially U-shaped channel 632 is formed on top surface 622 that extends transversally through saddle 458 so as to intersect the opening 630. Channel 632 is bounded by a curved side surface 634 sized so as to snugly receive stabilizing rod 107. As discussed in more detail below, when locking screw 600 is screwed into collar 456 (see FIG. 37), surface 634 of the U-shaped channel 632 presses against stabilizing rod 107. Although depicted as being substantially smooth, the channel surface 634 can be textured for improved gripping. Examples of the types of texture that can be used on channel surface 634 include: ribs, grooves, a waffle pattern, and an abrasive pattern. Other types of textures can also be used. See, e.g., the waffle-like texture shown in FIG. 38.

A generally concave cavity 636 is formed on bottom surface 624 of saddle 458 so as to encircle opening 630. Cavity 636 is bounded by an annular curved side surface 638 sized so as to snugly receive head 466 (see FIG. 37). As such, when locking screw 600 is screwed into collar 456, side surface 638 presses against head 466. As noted above, however, opening 630 in saddle 458 still allows access to socket 480 of head 466 when saddle 458 presses against head 466.

Saddle 458 has an outside diameter that is generally the same as the inner diameter of longitudinal passage 532 extending through collar 456. In some embodiments, a slit is formed in saddle 458 to allow saddle 458 to be able to be flexed for insertion into collar 456. For example, as shown in the depicted embodiment, a slit 640 is formed in saddle 458 that extends all the way between top and bottom surfaces 622 and 624 and between outer and internal side walls 626 and 628.

Slit 240 is bounded by side surfaces 642 and 644 that face each other across the slit 640. The slit 640 causes the saddle 620 to be generally "C" shaped, with the slit 640 being the mouth of the "C." As a result of the slit 640, the portions of saddle 458 on either side of slit 640 can be flexed toward each other, causing the diameter of saddle 458 to slightly decrease, thereby allowing saddle 458 to be inserted into longitudinal passage 132 of collar 456 and past lip 618 during assembly (see FIG. 37). Once positioned therein, the saddle 458 resiliently springs back to its original diameter and is retained within the passage 532 by the lip 618, which has a diameter that is slightly less then that of saddle 458.

To help keep saddle 458 oriented in a desired position within collar 456, a key 646 is also positioned thereon. Key 646 comprises a spline projecting out from outer side wall 626 and extending generally orthogonally between top and bottom surfaces 622 and 624. In the depicted embodiment, key 646 is positioned on the opposite side of saddle 458 as slit 640, although this is not required; key 646 can be positioned anywhere along the outer side wall 626. As noted above, key 646 is designed to fit within corresponding channel 648 formed on interior surface 524 of collar 456 (see FIG. 32). Other types of keys can alternatively be used, or, if desired, saddle 458 can be formed without a key. In some alternative embodiments the key 646 outwardly projects from the interior surface 524 of collar 456 and the corresponding channel 648 is formed on the outer side wall 626 of saddle 458. Saddle 458 is typically comprised of a radiopaque material such as those previously discussed with regard to head 110. However, other high strength, biocompatible materials can also be used.

Figure 36:
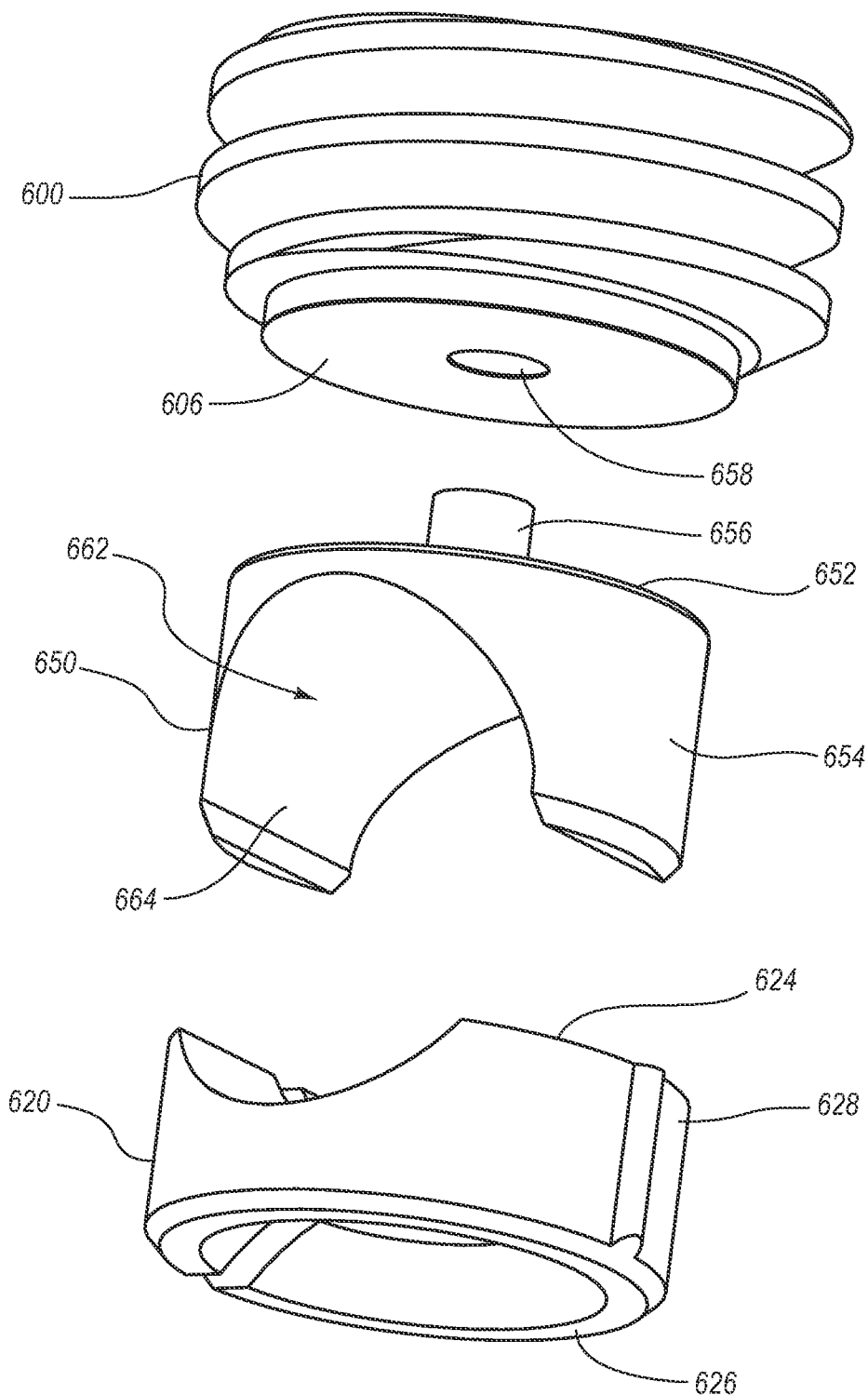
FIG. 36 is an exploded perspective view of the fastener shown in FIG. 32.

Returning to FIG. 32, fastener 460 can also include an alignment cap 650 movably attached to bottom end face 606 of locking screw 600 to further distribute the clamping forces around stabilizing rod 107. More specifically, as shown in FIG. 36, alignment cap 650 has a generally planar, circular top surface 652 with an encircling perimeter sidewall 654 extending downward therefrom. A post 656 extends upward from the center of top surface 652. Post 656 is designed to fit within a corresponding hole 658 on bottom end face 606 of locking screw 600. Alternatively, post 656 can be positioned on locking screw 600 and hole 658 can be formed on alignment cap 650

Similar to saddle 458, alignment cap 650 has a substantially U-shaped channel 662 extending transversally therethrough. Channel 662 is bounded by a curved side surface 664 sized so as to snugly receive stabilizing rod 107. Alignment cap 650 is rotatably attached to locking screw 600 by inserting post 656 into hole 658 so that as locking screw 600 is rotated, alignment cap 650 can remain rotationally stationary so as to press against stabilizing rod 107. Once inserted through hole 658, the end of post 656 can be splayed or otherwise spread apart so as to prevent the post 656 from being pulled back through hole 658, while still allowing locking screw 600 to rotate with respect to alignment cap 650. When locking screw 600 is screwed into collar 456, surface 664 of the U-shaped channel 662 presses against stabilizing rod 107. Similar to channel surface 634 of saddle 458, the channel surface 664 of alignment cap 650 can be substantially smooth or textured for improved gripping. Examples of some of the types of textures that can be used on channel surface 664 are as listed above regarding saddle 458.

Alignment cap 650 can be comprised of the same type of materials discussed above regarding saddle 458. Furthermore, alignment cap 650 can be comprised of the same material as saddle 458 or a different material.

FIG. 37 shows how the saddle 458 and alignment cap 650 combine to secure stabilizing rod 107 within collar 456. As discussed above, when locking screw 600 is screwed into collar 456 while stabilizing rod 107 is disposed within channels 536 and 538 (FIG. 32), surface 664 of alignment cap 650 presses against stabilizing rod 107. This pressure causes stabilizing rod 107 to, in turn, press against surface 634 of saddle 458, which causes surface 638 of saddle 458 to press against head 466. As a result, stabilizing rod 107 is rigidly attached to bone screw 452 while the clamping forces are distributed around stabilizing rod 107 by saddle 458 and alignment cap 650.

As can be appreciated, saddle 458 and alignment cap 650 can be used together, as shown in FIG. 37 or separately. That is, saddle 458 and alignment cap 650 are not reliant on each other and thus can be used with or without the other, as desired. Furthermore, the surfaces 634, 654, and 656 of channels 632 and 648 can be textured the same or have different textures from each other. Alternatively, a texture may be used on only one or more of the surfaces or, of course, all of the surfaces can be free of any texturing.

Figure 38:
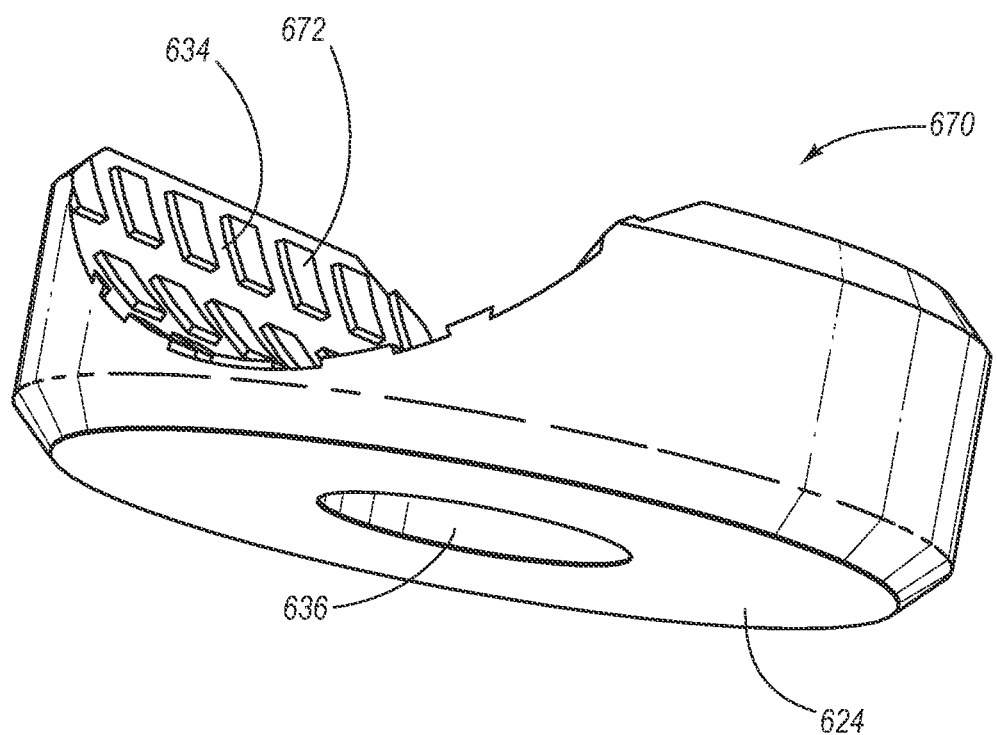
FIG. 38 is a perspective view of an alternative embodiment of the saddle shown in FIG. 35A.

FIG. 38 shows an alternative embodiment of a saddle 670 that can be used in the current invention. Saddle 670 is similar to saddle 458, except that there is no opening or slit extending through the saddle. Instead, a closed end cavity 636 is formed on bottom surface 624 that is configured to receive head 466 (FIG. 37). Saddle 670 also includes a waffle-like texture 672 on side surface 634. Of course, as discussed above, other types of textures can also be used.

Figure 39:
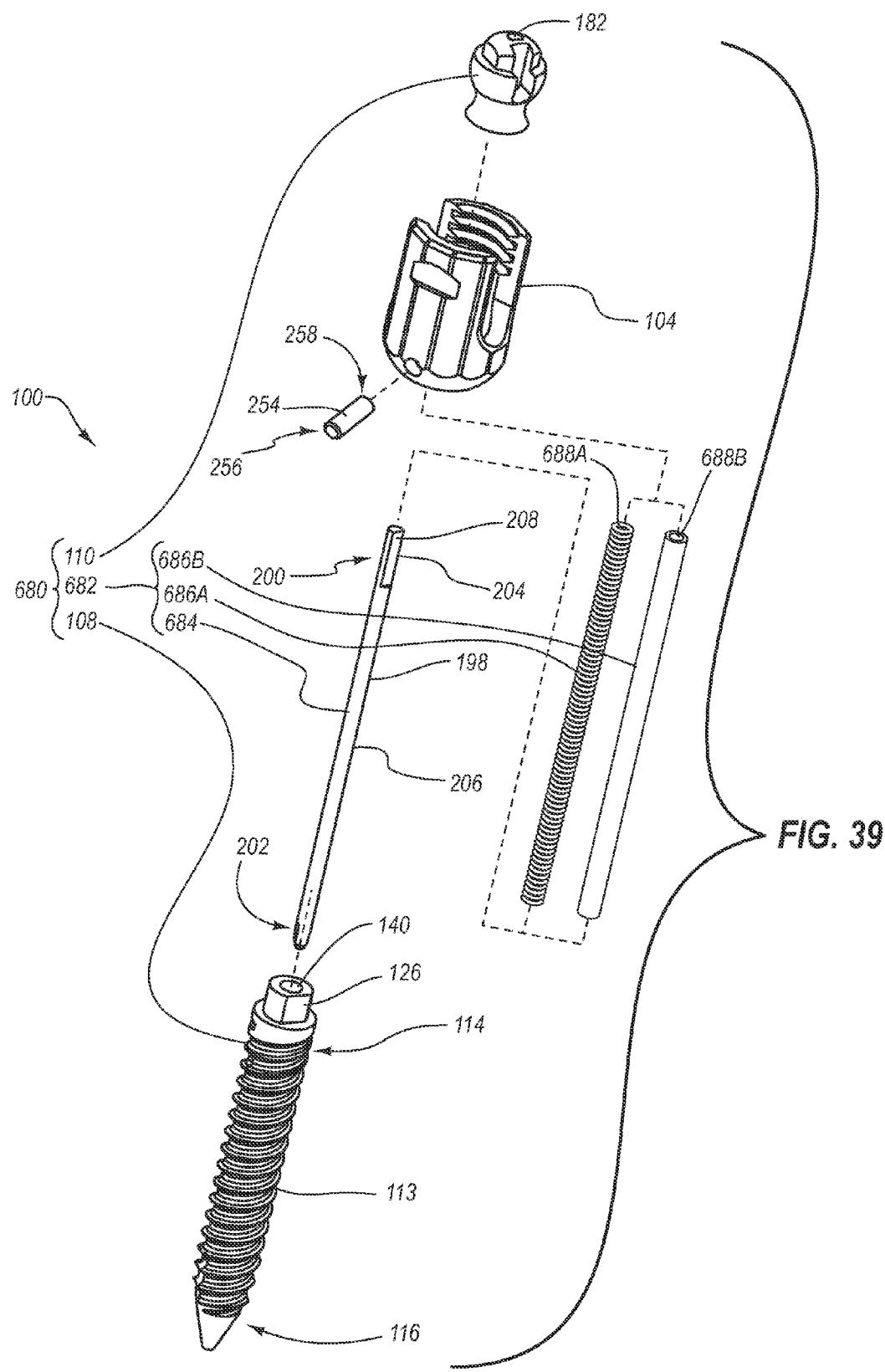
FIG. 39 is an exploded perspective view of an alternative embodiment of a screw portion having a modified core.

Depicted in FIG. 39 is another alternative embodiment of a screw portion 680 that can be used as part of a polyaxial bone screw. Screw portion 680 is similar to screw portion 102 shown in FIG. 2 and thus like elements are identified by like reference characters. Screw portion 680 includes shaft 108 and head 110 as previously discussed. However, in contrast to core 112, screw portion 680 includes a core 682. Core 682 comprises an elongated solid, inner core 684 in the form of a pin. Inner core 684 can have substantially the same configuration as core 112 previously discussed but can be made of a radiolucent material, such as those previously discussed with regard to shaft 108 or can be made of a radiopaque material, such as those previously discussed with regard to head 110.

Core 682 also includes an outer core that extends over at least a portion of inner core 684. In one embodiment an elongated, tubular outer core 686A is provided. Outer core 686A is comprised of a metal wire or ribbon that is coiled into the tubular configuration so as to bound a passage 688A longitudinally extending therethrough. The material for outer core 686A is selected so that outer core 686A is resiliently flexible like a coiled spring. For example, in one embodiment the wire or ribbon of outer core 686A is comprised of Nitinol and is heat treated when in the coiled configuration so that it obtains a coiled memory. Other metals can also be used. The wire or ribbon can be coiled directly around inner core 684 or can be separately coiled and then placed over inner core 684. Alternatively, an elongated, tubular outer core 686B can positioned over inner core 684. Outer core 686B comprises a solid tubular sleeve that bound a passage 688B longitudinally extending therethrough. Outer cores 686A and B can be comprised of a radiolucent material such as the radiolucent metals previously discussed with regard to head 110. It is appreciated that inner core 684 can be fabricated and then the outer core secured thereto. Alternatively, the outer core can first be formed and then inner core 684 can be formed by back filling, such as by injection, a material into the passage extending through inner core 684.

Outer cores 686A and B can be secured to inner core 684 by an epoxy, other adhesives or by other fastening techniques. Outer cores 686A and B can cover all or substantially all of inner core 684 so that the outer core is received within and is secured to head 110. Alternatively, the outer core can be sized to cover only a portion inner core 684. For example, the outer core can be sized to cover the portion of the inner core 684 within shaft 108 but not cover the portion of inner core 684 within head 110. To that end, the outer core can cover not more than 75% and more commonly not more than 85% of the length of inner core 684. It is appreciated that the physical properties of the bone screw can be adjusted by forming the core from different materials and elements.

Figure 40:
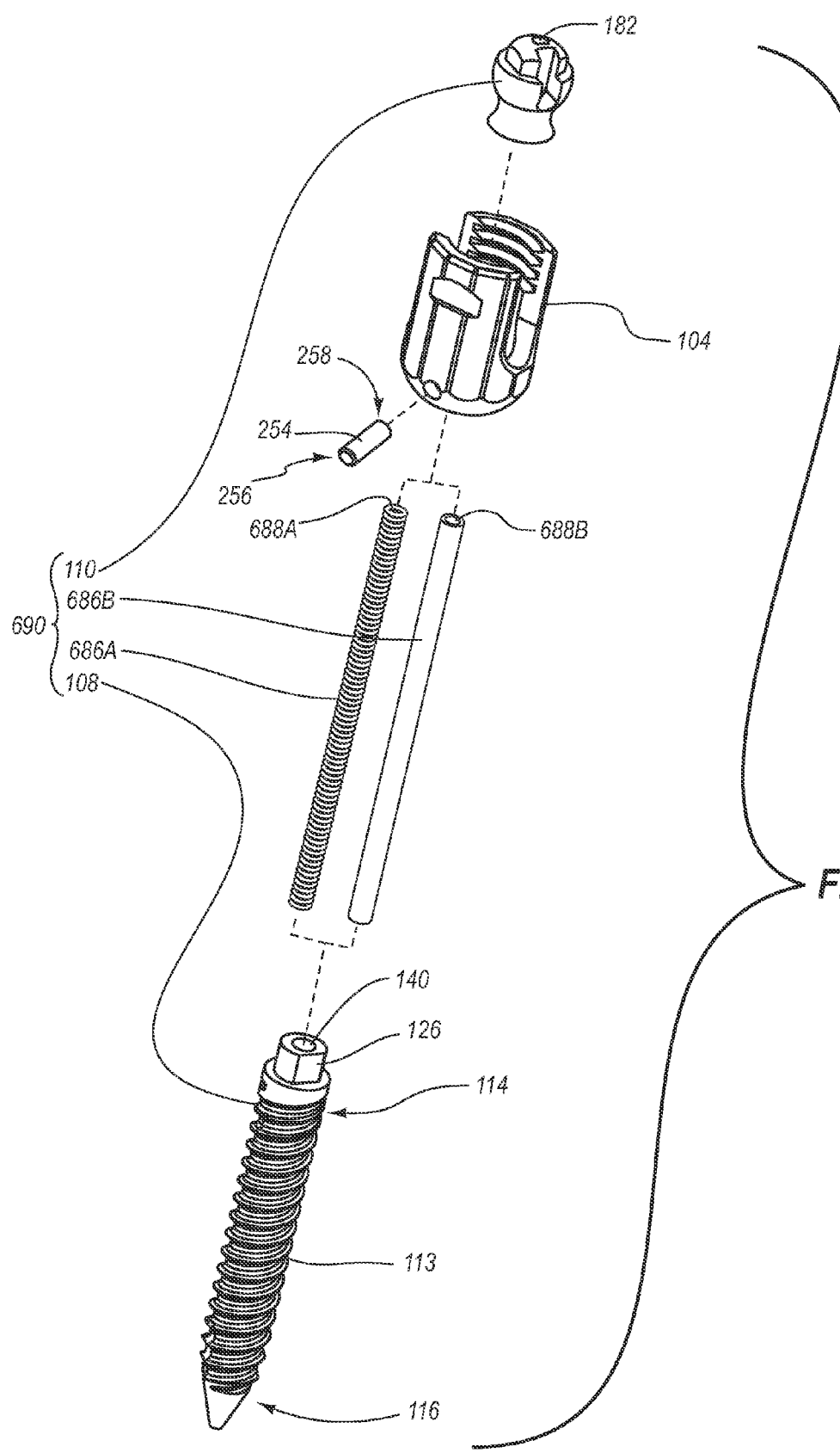
FIG. 40 is an exploded perspective view of another alternative embodiment of a screw portion having a modified core.

Depicted in FIG. 40 is another alternative embodiment of a screw portion 690 that can be used as part of a polyaxial bone screw. Screw portion 690 is similar to screw portion 680 except that inner core 682 has been eliminated. Thus, screw portion 690 comprises a core which is either outer core 686A or outer core 686B as discussed above. The cores are secured to shaft 108 and head 110 in the same manner that core 112 is secured to these elements as previously discussed. By having the core formed from a coiled and/or tubular member, flexible properties of the bone screw can be adjusted.

The bone screws previously disclosed herein have primarily been designed as polyaxial or fixed bone screws for use with spinal stabilization systems. It is appreciated, however, that the bone screws of the present invention need not be designed as a polyaxial or fixed bone screw for use with spinal stabilization systems but can be configured like any number of conventional bone screws that are used for applications such as securing bone plates over a facture, attaching cranial plates, securing joint or other implants to bone, fixing ligaments and other soft tissue to bone, and the like.

Figure 41:
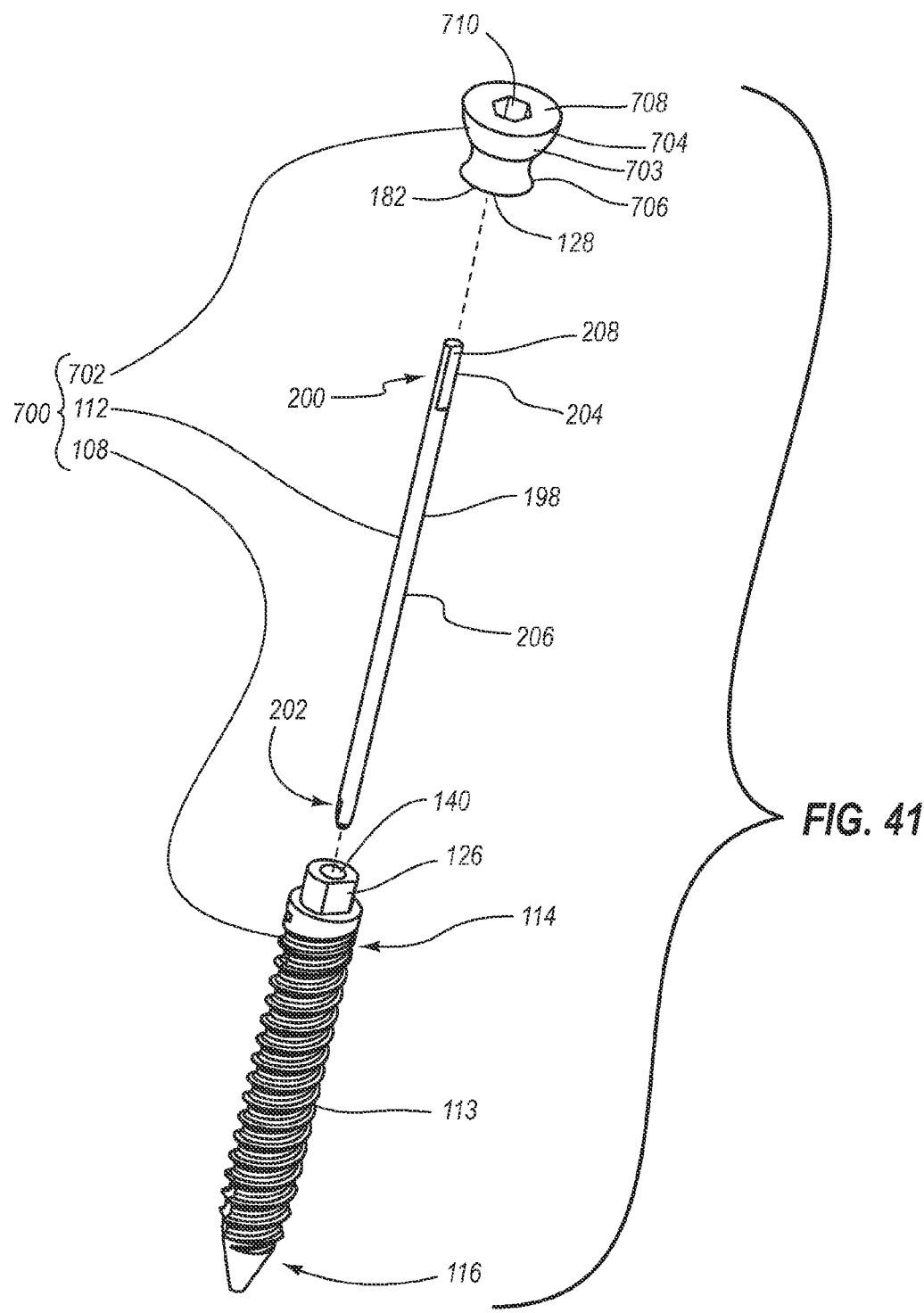
FIG. 41 is an exploded perspective view of a bone screw having a modified head.

By way of example and not by limitation, depicted in FIG. 41 is an exploded bone screw 700 incorporating features of the present invention wherein like elements are identified by like reference characters. Bone screw 700 comprises shaft 108, core 112 and a head 702. Head 702 is configured similar to a conventional screw head. Specifically, head 702 has a side wall 703 that extends between a proximal end 704 and an opposing distal end 706. Distal end 706 terminates at a bottom end face on which attachment recess 128 (FIG. 6) is formed. Attachment recess 128 permits head 702 to engage with attachment member 126 of shaft 108 in the manner previously discussed.

Side wall 703 flares outwardly as it extends from distal end 706 to proximal end 704. Proximal end 706 terminates at a substantially flat top end face 708. In one embodiment of the present invention, means are provided for engaging a driver to the inventive bone screws. The drivers can then be used for rotating the bone screws for implanting of the bone screws. By way of example and not by limitation, an engagement socket 710 is formed on top end face 708. Engagement socket 710 can be of any desired configuration such as polygonal, irregular or other non-circular configuration that permits a driver to engage engagement socket 710 for rotating bone screw 700. Engagement socket 710 can also be in the form of one or more slots such as are commonly used for engaging a driver such as a screw driver. In other embodiments, the means for engaging a driver can comprise top portion 152 as shown in FIG. 3 or other forms of projections to which a driver having a complementary socket can engage. Other locking structures commonly used for engaging a driver can also be used. It is appreciated that each of the different bone screws as disclosed herein can include such means for engaging a driver.

Second passageway 183 (FIG. 6) can be formed on the floor of attachment recess 128 and extend to or toward engagement socket 710. Second passageway 183 permits head 702 to engage with core 112 in the manner previously discussed. It is appreciated that the alternative materials, methods of manufacture, use of markers and other alternatives as previously discussed with regard to the shaft, core and head of screw portion 102 are also applicable to the shaft, core and head of bone screw 700.

It is appreciated that head 702 can have a variety of different configurations and that it can be integrally formed with the core. By way of example, depicted in FIG. 42 is an exploded view of a bone screw 720 incorporating features of the present invention wherein like elements are identified by like reference characters. Similar to screw portion 454 shown in FIG. 33, bone screw 700 comprises shaft 462, core 464 and a head 722. Core 464 and head 722 are integrally formed as a single, unitary structure or can be rigidly fixed together such as by welding, press fit or other securing techniques. Head 722 comprises a cylindrical stem 724 that terminates at a bottom end face 726. Bottom end face 726 is designed to position against top end face 132 of shaft 462. Formed on the opposing end of stem 724 is a substantially semi-spherical head portion 728. Head portion 728 has a flat bottom surface that radially outwardly projects from stem 724 and has a top crown on which engagement socket 710 is formed. Again, engagement socket 710 can also be in the form of one or more slots for engaging a driver such as a screw driver. It is appreciated that the alternative materials, methods of manufacture, use of markers and other alternatives as previously discussed with regard to the shaft, core and head of screw portion 454 are also applicable to the shaft, core and head of bone screw 720.

In many of the foregoing embodiments, it is discussed that the core can be comprised of a radiopaque material while the shaft is comprised of a radiolucent material. In each of the embodiments, however, it is also appreciated that that both the core and the shaft can be comprised of a radiolucent material. For example, in each of the embodiments, the core can be comprised of a ceramic or rigid thermoplastic that may include fibers or other fillers while the shaft is comprised of an epoxy fiber matrix. Thus, in some embodiments, the core and the shaft can be comprised of different radiolucent materials. In still other embodiments, the core and shaft can be made of the same radiolucent material. In each embodiment, however, the various makers discussed herein can be used with the core and/or shaft.

A number of different methods and embodiments are disclosed herein. It is appreciated that the different methods and components from the different embodiments can be mixed and matched to produce a variety of still other different embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone screw comprising:
   an elongate shaft extending longitudinally between a proximal end and an opposing distal end, the shaft bounding a first passageway at least partially extending between the proximal end and the distal end, the shaft being comprised of a radiolucent material;
   a core disposed within the first passageway of the shaft, the core comprising a tubular outer core having an interior surface that bounds a passage extending therethrough and an inner core disposed within the outer core, the shaft being comprised of a pre-fabricated sheet comprised of the one or more radiolucent fibers and an adhesive that encircles a radiopaque core so that the one or more radiolucent fibers radially encircling the core;
   an enlarged head disposed at an end of the core, the enlarged head having a maximum diameter that is larger than a maximum diameter of the core; and
   a helical thread recessed into the pre-fabricated sheet encircling the radiopaque core.

2. The bone screw as recited in claim 1, wherein the head is secured to the proximal end of the shaft.

3. The bone screw as recited in claim 1, wherein the first passageway extends completely through the shaft.

4. The bone screw as recited in claim 1, further comprising a marker disposed on or within the shaft and spaced apart from the core, the marker being comprised of a radiopaque material.

5. The bone screw as recited in claim 4, wherein the marker comprises a ring disposed within the shaft so as to substantially encircle the core or a ring layer disposed on an external surface of the shaft so as to substantially encircle the core.

6. The bone screw as recited in claim 1, wherein the core has an outer surface with a projection projecting therefrom.

7. The bone screw as recited in claim 1, further comprising a collar pivotably mounted on the head.

8. The bone screw as recited in claim 1, wherein the head comprises an annular shoulder, an annular head portion, and a neck formed therebetween, the neck inwardly constricting relative to the annular shoulder and the annular head.

9. The bone screw as recited in claim 1, wherein the shaft encircles the core but does not encircle the head.

10. The bone screw as recited in claim 1, wherein the core extends the entire length of the shaft.

11. The bone screw as recited in claim 1, wherein the one or more radiolucent fibers radially encircle the core in a helical pattern that extends along a length of the core.

12. The bone screw as recited in claim 1, wherein the radiopaque material of the core is comprised of titanium, stainless steel, tungsten, cobalt based alloys, cobalt chrome alloys, nickel titanium alloys, platinum, iridium, gold, barium and alloys thereof.

13. The bone screw as recited in claim 1, wherein the outer core is comprised of a radiopaque material and the inner core is comprised of a radiolucent material.

14. The bone screw as recited in claim 1, wherein the outer core comprises a metal wire or ribbon that is coiled into a tubular configuration.

15. A method of manufacturing a bone screw, the method comprising:
   forming an elongated shaft about a core, an enlarged head being formed on an end of the core, the shaft having a longitudinal axis extending between a proximal end and an opposing distal end with a first passageway that extends completely through the shaft along the longitudinal axis, the core being disposed within the first passageway and extending along the longitudinal axis, the shaft being comprised of a radiolucent material that includes one or more radiolucent fibers that radially encircles the core, the core comprising a tubular outer core having an interior surface that bounds a passage extending therethrough and an inner core disposed within the outer core, wherein the shaft is formed by:
      winding the one or more radiolucent fibers having an adhesive thereon about a radiopaque core; or
      winding a sheet comprised of the one or more radiolucent fibers and an adhesive about the radiopaque core; and forming a helical thread on an exterior surface of the shaft by removing a portion of the exterior surface of the shaft.

16. The method as recited in claim 15, wherein the step of removing a portion of the exterior surface of the shaft is accomplished through the use of a grinder, lathe or cutting tool.

17. The method as recited in claim 15, wherein the one or more radiolucent fibers radially encircle the core in a helical pattern that extends along a length of the core.

18. The method as recited in claim 15, wherein the core and the head are comprised of a metal.

* * * * *